United States Patent [19]

Tanida et al.

[11] Patent Number: 5,478,809
[45] Date of Patent: Dec. 26, 1995

[54] TAN-1511, ITS DERIVATIVES, PRODUCTION AND USE THEREOF

[75] Inventors: Seiichi Tanida, Kyoto; Tsuneaki Hida, Hyogo; Mitsuhiro Wakimasu, Ibaraki, all of Japan

[73] Assignee: Takeda Chemical Industries, Ltd., Osaka, Japan

[21] Appl. No.: 174,365

[22] Filed: Dec. 28, 1993

[30] Foreign Application Priority Data

Dec. 28, 1992 [JP] Japan .................................. 4-349062
Aug. 9, 1993 [JP] Japan .................................. 5-197579

[51] Int. Cl.$^6$ ............................ A61K 38/00; C07K 5/00; C07K 7/00; C07K 17/00
[52] U.S. Cl. ................................ 514/16; 514/17; 514/18; 530/329; 530/330; 530/331
[58] Field of Search ................. 514/16–18; 530/329–331

[56] References Cited

U.S. PATENT DOCUMENTS 4,666,886  5/1987  Baschang et al. .................. 514/17

FOREIGN PATENT DOCUMENTS 0000330  1/1979  European Pat. Off. .
0210412  2/1987  European Pat. Off. .
4-46194  2/1992  Japan .
4-99796  3/1992  Japan .

OTHER PUBLICATIONS

Chem. Pharm. Bull., "Synthesis of Optically Active Lipopeptide Analogs from the Outer Membrane of *Escherichia coli*" Kurimura et al., 39 (10), pp. 2590–2596 (1991).
Chem. Pharm. Bull., "Synthesis and Mitogenic Activity of Chiral Lipopeptide WS1279 and Its Derivatives" Kurimura et al., 41(11), pp. 1965–1970 (1993).
Chem. Pharm. Bull., "Synthesis of Biologically Active Pentapeptide Analogs of the N–Terminal Part of Lipoprotein From the Outer Membrane of *Escherichia coli*" Kurimura et al., 38 (4), pp. 1110–1112 (1990).
Peptide Chemistry 1990: Y. Shimonishi (Ed.), Protein Research Foundation, Osaka, Japan (1990), "Synthesis and Mitogenic Activity of Lipopeptide and Its Analogs" Kurimura et al., pp. 37–42.
Peptide Chemistry 1991: A. Suzuki (Ed.) Protein Research Foundation, Osaka, Japan (1991), "Stereospecific Synthesis and Mitogenic Activity of Lipopeptide WS 1279 and Its Derivatives" Kurimura et al., pp. 361–366.
Int. J. Peptide Protein Res., "Synthesis of Novel Immunologically Active Tripalmitoyl–S–Glycerylcysteinyl Lipopeptides as Useful Intermediates for Immunogen Preparations" Metzger et al., 37, 1991, pp. 46–57.

Primary Examiner—Jill Warden
Assistant Examiner—Sheela J. Huff
Attorney, Agent, or Firm—Wenderoth, Lind & Ponack

[57] ABSTRACT

A compound of the formula:

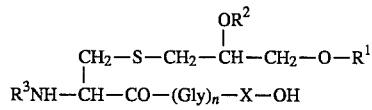

wherein each $R^1$, $R^2$ and $R^3$ is an aliphatic acyl group, X is an amino acid sequence consisting of 1 to 5 amino acid residues which contain at least one acidic amino acid residue, n is an integer of 0 to 4, provided that when n is 0, X has glutamyl-glycyl at its N-terminal and when n is 1 or 2, the acidic amino acid residue is an acidic amino acid residue other than D-glutamyl, or a salt thereof has an activity of remarkably improving anhematopoiesis and is useful as an immuno-stimulating agent having a leukocyte-increasing activity.

7 Claims, 5 Drawing Sheets

TAN-1511, ITS DERIVATIVES, PRODUCTION AND USE THEREOF

BACKGROUND OF THE INVENTION

1. Field of the Invention

This invention relates to a microbial metabolite TAN-1511 and its related compounds, which are useful as therapeutic agents in the treatment of leukocytopenia resulting from various causes, such as diseases due to a decrease of leukocytes, or diseases requiring, from the therapeutic viewpoint, an increase of bone marrow cells or leukocytes.

2. Description of Related Art

In Hoppe-Seyler's Zeitschrift für Physiologiche Chemie 364, pp 593–606 (1983), a synthetic peptide derived from lipoprotein produced by *E. coli*, which is shown by the formula:

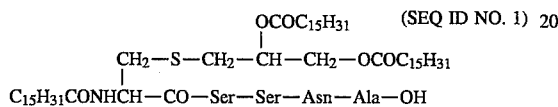
(SEQ ID NO. 1)

is disclosed.

And, in JPA H4(1992)-046194, WS 1279A substance shown by the formula:

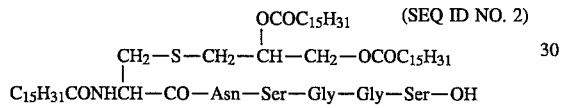
(SEQ ID NO. 2)

is disclosed.

Achiwa et al. synthesized these compounds as optical active compounds. [cf. JPA H4(1992)-099796, chem. Pharm. Bull. 39, p 2590 (1991) and Peptide Chemistry, p. 361 (1991)].

However, the compounds of this invention are not described in these references.

Incidentally, abbreviations of amino acid, peptide or the like used in the present invention are based on those in accordance with IUPAC-IUB Commission on Biochemical Nomenclature or those conventionally used in the relevant fields, and, possible optical isomers of amino acid are, unless otherwise specified, L-isomers.

Chemotherapy or radiotherapy of cancers causes serious leukocytopenia, which induces a lowering of resistance against infections or other various diseases so that sufficient therapeutic effects are not expected. This is being taken up as a grave concern in the field of cancer therapy. Under such circumstances, the development of drugs, which mitigate the suppression of hematopoietic function caused by these therapeutic methods and are capable of promoting the recovery of leukocyte number, has been ardently desired. And, in the therapy by bone marrow transplantation, drugs capable of promoting the proliferation of bone marrow cells then to be transplanted and capable of recovering the number of leukocyte promptly are desired.

While taking the present circumstances mentioned above into consideration, the present inventors pursued their studies, from a fresh viewpoint, on compounds having the action of increasing the number of leukocytes. As the result, the present inventors found that, among a great number of microbes isolated from soil, some microbes produce a novel substance, that these microbes belong to the genus Streptosporangium and that, by incubating these microbes in an appropriate culture medium, the compound capable of promoting the proliferation of bone marrow cells of mice and increasing the number of peripheral leukocyte can be accumulated in the culture medium. The present inventors then isolated this compound and, on the basis of its physicochemical and biological properties, the compound was confirmed as a novel substance and called physiologically active substance TAN-1511 and named each component thereof TAN-1511A, B and C. And, since these compounds are respectively composed of different fatty acid moieties, the present inventors conducted also the study of synthesizing them as a single compound, respectively. Based on these findings, the present inventors made further studies to complete the present invention.

SUMMARY OF THE INVENTION

This invention is to provides

1) A compound of the formula:

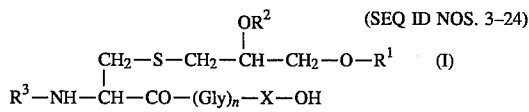
(SEQ ID NOS. 3–24)
(I)

wherein each $R^1$, $R^2$ and $R^3$ is an aliphatic acyl group, X is an amino acid sequence consisting of 1 to 5 amino acid residues which contain at least one acidic amino acid residue, n is an integer of 0 to 4, provided that when n is 0, X has glutamyl-glycyl at its N-terminal and when n is 1 or 2, the acidic amino acid residue is an acidic amino acid residue other than D-glutamyl, or a salt thereof.

2) A compound according to (1), wherein n is 3 or 4.

3) A compound according to (1), wherein n is 3.

4) A compound according to (1), wherein X is an amino acid sequence consisting of 1 to 4 amino acid residues, the N-terminal of said amino acid sequence being an acidic amino acid residue and the remaining amino acid residue being selected from the group consisting of glycyl, alanyl, prolyl, leucyl and threonyl; and n is 3.

5) A compound according to (1), wherein the aliphatic acyl group is $C_{7-23}$ aliphatic acyl group.

6) A compound according to (1), wherein the acidic amino acid residue has one amino group and two or more carboxyl groups.

7) A compound according to (1), wherein the compound is (2R,6R)-2-tetradecanoylamino-6,7-bis(hexadecanoyloxy)- 4-thiaheptanoyl-glycyl-glycyl-glycyl-glutamyl-threonyl-threonine (SEQ ID No. 25).

8) A compound according to (1), wherein the compound is (2R,6R)-2-tetradecanoylamino-6,7-bis(hexadecanoyloxy)- 4-thiaheptanoyl-glycyl-glycyl-glycyl-glutamic acid (SEQ ID No. 26).

9) A compound according to (1), wherein the compound is (2R,6R)-2-tetradecanoylamino-6,7-bis(hexadecanoyloxy)- 4-thiaheptanoyl-glycyl-glycyl-glutamic acid (SEQ ID No. 27).

10) A compound according to (1), wherein the compound is (2R,6R)-2-tetradecanoylamino-6,7-bis(hexadecanoyloxy)- 4-thiaheptanoyl-glycyl-glutamyl-glutamic acid (SEQ ID No. 28).

11) A compound according to (1), wherein the compound is (2R,6R)-2-tetradecanoylamino-6,7-bis(hexadecanoyloxy)- 4-thiaheptanoyl-glutamyl-glycyl-glutamic acid SEQ ID. No. 29).

12) A compound according to (1), wherein the compound is (2R,6R)-2-tetradecanoylamino-6,7-bis(hexadecanoyloxy)- 4-thiaheptanoyl-glutamyl-glycyl-D-glutamic acid (SEQ ID No. 30).

13) A method of producing TAN-1511A of the formula (II):

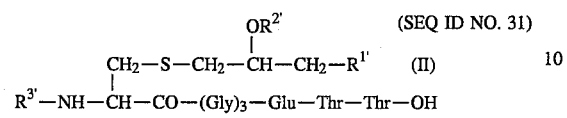

wherein each $R^{1'}$, $R^{2'}$ and $R^{3'}$ is a mixed higher fatty acid residue; TAN-1511B of the formula (III):

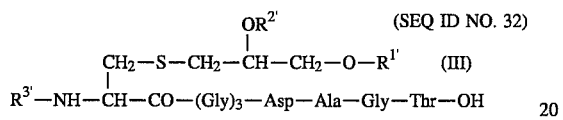

wherein each $R^{1'}$, $R^{2'}$ and $R^{3'}$ is a mixed higher fatty acid residue; TAN-1511C of the formula (IV):

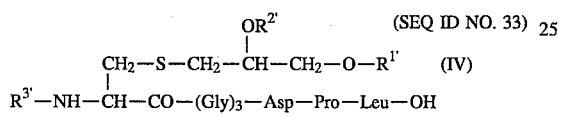

wherein each $R^{1'}$, $R^{2'}$ and $R^{3'}$ is a mixed higher fatty acid residue; or salts thereof, which comprises cultivating a microorganism belonging to the genus Streptosporangium capable of producing TAN-1511A, B or C in a culture medium, allowing said compounds to be produced and accumulated, and then, recovering the accumulated compounds.

14) A method of producing the compound or its salt as defined in (1), which comprises subjecting a compound of the formula (V):

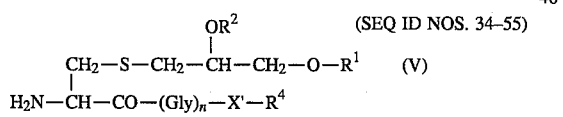

wherein each $R^1$ and $R^2$ is an aliphatic acyl group, $R^4$ is an hydroxyl group which may be protected, X' is an amino acid sequence consisting of 1 to 5 optionally protected amino acid residues which contain at least one optionally protected acidic amino acid residue, n is an integer of 0 to 4, provided that when n is 0, X' has optionally protected glutamyl-glycyl at its N-terminal and when n is 1 or 2, the optionally protected acidic amino acid residue is an optionally protected acidic amino acid residue other than optionally protected D-glutamyl, or a salt thereof to acylation, then, where desired, subjecting the thus acylated compound to deprotection reaction.

15) An immuno-stimulating composition having a leukocyte-increasing action, which comprises a compound or its salt as defined in (1).

16) A compound (2R,6R)-2-tetradecanoylamino-6,7-bis(hexadecanoyloxy)- 4-thiaheptanoyl-glycyl-D-glutamic acid or its salt (SEQ ID No. 56).

17) A compound (2R,6R)-2-tetradecanoylamino-6,7-bis(hexadecanoyloxy)- 4-thiaheptanoic acid or its salt (SEQ ID No. 57).

18) A compound (2R,6R)-2-tetradecanoylamino-6,7-bis(hexadecanoyloxy)- 4-thiaheptanoyl-glycyl-glutamyl-D-glutamic acid or its salt (SEQ ID No. 58).

19) A compound (2R,6R)-2-tetradecanoylamino-6,7-bis(hexadecanoyloxy)- 4-thiaheptanoyl-glutamyl-glutamic acid or its salt (SEQ ID No. 59).

20) A compound (2R,6R)-2-tetradecanoylamino-6,7-bis(hexadecanoyloxy)- 4-thiaheptanoyl-glutamyl-D-glutamic acid or its salt (SEQ ID No. 60).

21) A compound (2R,6R)-2-tetradecanoylamino-6,7-bis(hexadecanoyloxy)- 4-thiaheptanoyl-glutamyl-glutamyl-glutamic acid or its salt (SEQ ID No. 61).

22) A compound (2R,6R)-2-tetradecanoylamino-6,7-bis(hexadecanoyloxy)- 4-thiaheptanoyl-glutamyl-glutamyl-D-glutamic acid or its salt (SEQ ID No. 62).

23) A compound (2R,6R)-$N^\delta$-[2-hexadecanoylamino-6,7-bis(hexadecanoyloxy)- 4-thiaheptanoyl]-ornithyl-glycyl-glycyl-glutamic acid or its salt (SEQ ID No. 63).

DETAILED DESCRIPTION OF THE INVENTION

Figure 1:
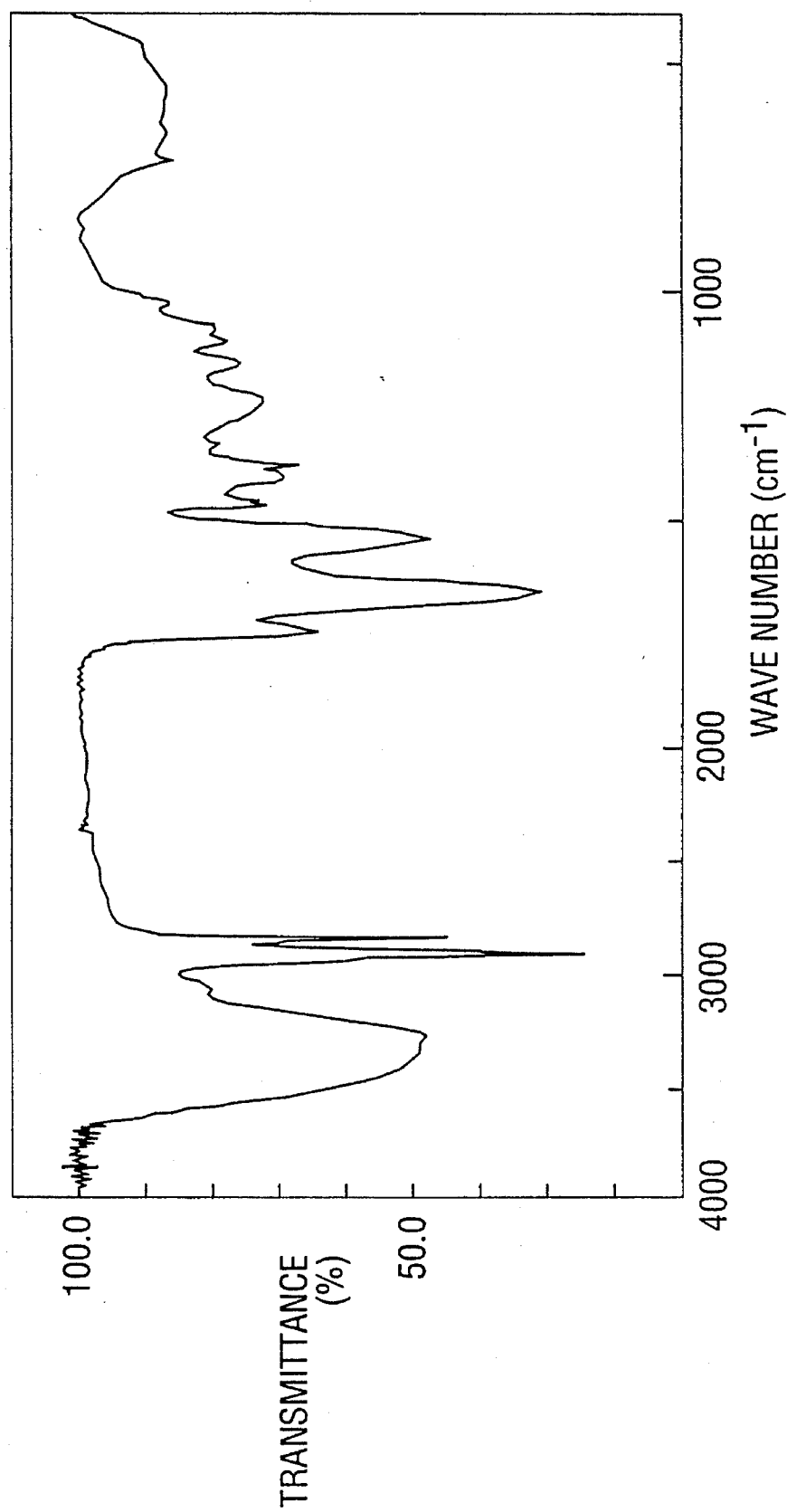
FIG. 1 is an IR spectrum of TAN-1511 A.

Referring to the above-mentioned formulae (I) and (V) examples of the aliphatic acyl group shown by $R^1$, $R^2$ or $R^3$ include aliphatic acyl groups derived from aliphatic carboxylic acid. Examples of the aliphatic acyl groups include $C_{7-30}$ saturated or unsaturated aliphatic acyl groups (e.g. heptanoyl, octanoyl, decanoyl, dodecanoyl, tridecanoyl, tetradecanoyl, pentadecanoyl, hexadecanoyl, heptadecanoyl, octadecanoyl, nonadecanoyl, tetracosanoyl, hexacosanoyl, eicosanoyl, heneicosanoyl, docosanoyl, tetracosanoyl, hexacosanoyl, ethyldodecanoyl, methyltridecanoyl, ethyltridecanoyl, methyltetradecanoyl, ethyltetradecanoyl, methylpentadecanoyl, ethylpentadecanoyl, methylhexadecanoyl, ethylhexadecanoyl, methylheptadecanoyl, ethylheptadecanoyl, methyloctadecanoyl, ethyloctadecanoyl, octacosanoyl, triacontanoyl, myristoleoyl, oleoyl, palmitoleoyl, elaidoyl, cis, cis-9,12-octadecatrienoyl, 9,12,15-octadecatrienoyl, 9,11,13-octadecatrienoyl, 5,8,11,14-icosatetraenoyl, cis-15-tetracosaenoyl, etc.).

Preferable examples of aliphatic acyl groups include $C_{7-23}$ saturated or unsaturated higher aliphatic acyl groups (e.g. heptanoyl, octanoyl, decanoyl, dodecanoyl, tridecanoyl, tetradecanoyl, pentadecanoyl, hexadecanoyl, heptadecanoyl, octadecanoyl, nonadecanoyl, eicosanoyl, heneicosanoyl, docosanoyl, ethyldodecanoyl, methyltridecanoyl, ethyltridecanoyl, methyltetradecanoyl, ethyltetradecanoyl, methylpentadecanoyl, ethylpentadecanoyl, methylhexadecanoyl, ethylhexadecanoyl, methylheptadecanoyl, ethylheptadecanoyl, methyloctadecanoyl, ethylocatadecanoyl myristoleoyl, oleoyl, palmitoleoyl, elaidoyl, cis, cis-9,12-octadecatrienoyl, 9,12,15-octadecatrienoyl, 9,11,13-octadecatrienoyl, 5,8,11,14-icosatetraenoyl, etc.).

Especially preferable examples of the aliphatic acyl groups shown by $R^1$ or $R^2$ include $C_{12-22}$ saturated or unsaturated higher aliphatic acyl groups (e.g. dodecanoyl, tridecanoyl, tetradecanoyl, pentadecanoyl, hexadecanoyl, heptadecanoyl, octadecanoyl, nonadecanoyl, eicosanoyl, heneicosanoyl, docosanoyl, ethyldodecanoyl, methyltridecanoyl, ethyltridecanoyl, methyltetradecanoyl, ethyltetradecanoyl, methylpentadecanoyl, ethylpentadecanoyl, methylhexadecanoyl, ethylhexadecanoyl, methylheptadecanoyl, ethylheptadecanoyl, methyloctadecanoyl, ethyloctadecanoyl, myristoleoyl, oleoyl, palmitoleoyl, elaidoyl, cis, cis-9,12-octadecatrienoyl, 9,12,15-octadecatrienoyl, 9,11, 13-octadecatrienoyl, 5,8,11,14-icosatetraenoyl, etc.).

Especially preferable examples of the aliphatic acyl groups shown by $R^3$ include $C_{7-17}$ saturated or unsaturated higher aliphatic acyl groups (e.g. heptanoyl, octanoyl, decanoyl, dodecanoyl, tridecanoyl, tetradecanoyl, pentadecanoyl, hexadecanoyl, heptadecanoyl, ethyldodecanoyl, methyltridecanoyl, ethyltridecanoyl, methyltetradecanoyl, ethyltetradecanoyl, methylpentadecanoyl, ethylpentadecanoyl, methylhexadecanoyl, myristoleoyl, palmitoleoyl, etc.).

Referring to the above-mentioned formulae (II), (III) and (IV), examples of the mixed higher fatty acid residues shown by $R^{1'}$, $R^{2'}$ or $R^{3'}$ include a mixture of the above-mentioned $C_{7-30}$ saturated or unsaturated higher aliphatic acyl groups, more preferably, a mixture of the above-mentioned $C_{7-23}$ saturated or unsaturated higher aliphatic acyl groups.

Especially preferable examples of the mixed higher fatty acid residues shown by $R^{1'}$ or $R^{2'}$ include a mixture of the above-mentioned $C_{12-22}$ saturated or unsaturated higher aliphatic acyl groups. And, especially preferable examples of the mixed higher fatty acid residues shown by $R^{3'}$ include a mixture of the above-mentioned $C_{12-22}$ saturated or unsaturated higher aliphatic acyl groups.

In the above-mentioned formula (I), the amino acid in the amino acid sequence shown by X means a compound having in its molecule an amino group and an acidic group (e.g. carboxyl group, sulfonic acid group). Preferable examples of the amino acid include those described in Dai Yuhki Kagaku (Encyclopedia of Organic Chemistry) Vol. 21 "Natural Polymers III" compiled under the supervision of Dr. Munio Kotake, Published by Asakura Shoten, 1960, in Japan and "Amino acids and peptides" by Chapman and Hall, compiled by J. S. Davies, 1985 in U.S.A.

To state more concretely, there may be mentioned, for example, amino acid constituting protein [e.g. aliphatic monoamino monocarboxylic acid such as glycine, alanine, valine, leucine, isoleucine or the like, aliphatic hydroxyamino acid such as serine, threonine or the like, acidic amino acid such as aspartic acid, glutamic acid or the like, acidic amino acid amide such as asparagine, glutamine or the like, aromatic amino acid such as phenylalanine, tyrosine, tryptophane or the like, iminocarboxylic acid such as proline, hydroxyproline or the like, basic amino acid such as arginine, lysine, histidine or the like, and sulfur-containing amino acid such as methionine, cystine, cysteine or the like], amino acid obtained from natural sources as, for example, metabolites of microorganisms or components of animals and plants [e.g. aliphatic monoamino monocarboxylic acid such as L-α-aminobutyric acid, γ-aminobutyric acid, β-aminoisobutyric acid, β-alanine, homoserine, α-methyl-D-serine, O-carbamyl-D-serine, δ-hydroxy-γ-oxo-norvaline, or the like, monoamino dicarboxylic acid such as L-α-aminoadipic acid, L-β-aminoadipic acid, L-theanine, L-γ-methylene glutamic acid, L-γ-methyl glutamic acid or the like, diaminomonocarboxylic acid such as L-ornithine, β-lysine, α,β-diaminopropionic acid, L-α,γ-diaminobutyric acid, or the like, diaminodicarboxylic acid such as diaminopimelic acid or the like, sulfonic acid-containing monoaminomonocarboxylic acid such as cysteic acid, sulfonic acid-containing amino acid such as taurine or the like, aromatic amino acid such as kynurenine, 3,4-dioxyphenyl-L-alanine or the like, heterocyclic amino acid such as 2,3-dicarboxyaziridine, [S]-2-amino-3-(isoxazolin- 5-one-4-yl)-propionic acid, anticapsin or the like, basic amino acid such as L-4-oxalysine, L-4-oxolysine, [3R,5R]-3,6-diamino-5-hydroxyhexanoic acid, or the like, sulfur-containing amino acid such as lanthionine, S-methyl-L-cysteine or the like, cyclic amino acid such as pipecolic acid, azetidine-2-carboxylic acid, [1R, 2S]-2-aminocyclopentane-1-carboxylic acid, or the like, amino acid substituted with a specific functional group such as citrulline, alanosine, L-azaserine, or the like], and amino acids having various substituents obtained by organic synthesis (e.g. 6-aminohexanoic acid, 8-aminooctanoic acid, 12-aminododecanoic acid, 4-aminobenzoic acid, 4-(aminomethyl)benzoic acid, 4-(N-(carboxymethyl)aminomethyl)benzoic acid, or the like].

The residue means a divalent group having bonds to the amino group and acidic group, respectively.

In the case where the amino acid residue is possibly an optically active isomer, it can take any of L-, D- and DL-form.

Referring to the above-mentioned general formula (I), examples of the acidic amino acid in the amino acid sequence consisting of 1 to 5 amino acid residues which contain at least one acidic amino acid residue shown by X or Y include the above-mentioned acidic amino acid. To state more concretely, there may be mentioned, a compound one or more acidic functional groups (e.g. carboxyl group, sulfonic acid group, etc.) in addition to one carboxyl group and one amino group. Preferable examples of the acidic amino acid include a compound having one amino group and two or more carboxyl group [e.g. amino dicarboxylic acid (e.g. aspartic acid, glutamic acid, L-α-aminoadipic acid, L-β-aminoadipic acid, 2,3-dicarboxyaziridine, etc.) or the like], more preferably, α-aminodicarboxylic acid (e.g. aspartic acid, glutamic acid, 2-aminoadipic acid, etc.), and, among them, aspartic acid and glutamic acid are especially preferable.

Preferable examples of the compound of the formula (I), or a salt thereof include;

(1) the compound (I), wherein n is 0, X is glutamyl-glycyl-glutamyl;

(2) the compound (I), wherein n is 1, X is L-glutamyl or glutamyl-glutamyl;

(3) the compound (I), wherein n is 2, X is L-glutamyl; or (4) the compound (I), wherein n is 3, X is an amino acid sequence consisting of 1 to 3 amino acid residues selected from the group consisting of an acidic amino acid residue and threonyl, the N-terminal of X is an acidic amino acid residue, preferably the compound (I), wherein n is 3, X is an amino acid sequence consisting of 1 to 3 amino acid residues selected from the group consisting of glutamyl, aspartyl and threonyl, the N-terminal of X is glutamyl or aspartyl, more preferably the compound (I), wherein n is 3, X is an amino acid sequence consisting of 1 to 3 amino acid residues selected from the group consisting of glutamyl and threonyl, the N-terminal of X is glutamyl.

Preferred concrete examples of the compound (I) or a salt thereof include;

(2R,6R)-2-tetradecanoylamino-6,7-bis(hexadecanoyloxy)-4-thiaheptanoyl-glycyl-glycyl-glycyl-glutamyl-threonylthreonine (SEQ ID No: 64), (2R,6R)-2-tetradecanoylamino-6,7-bis(hexadecanoyloxy)-4-thiaheptanoyl-glycyl-glycyl-glycyl-glutamic acid (SEQ ID No: 65), (2R,6R)-2-tetradecanoylamino-6,7-bis(hexadecanoyloxy)-4-thiaheptanoyl-glycyl-glycyl-glutamic acid (SEQ ID No: 66), (2R,6R)-2-tetradecanoylamino-6,7-bis(hexadecanoyloxy)-4-thiaheptanoyl-glycyl-glutamyl-glutamic acid (SEQ ID No: 67), (2R,6R)-2-tetradecanoylamino-6,7-bis(hexadecanoyloxy)-4-thiaheptanoyl-glutamyl-glycyl-glutamic acid (SEQ ID No: 68), (2R,6R)-2-tetradecanoylamino-6,7-bis(hexadecanoyloxy)-4-thiaheptanoyl-glutamyl-glycyl-D-glutamic acid or (SEQ ID No. 69) salts thereof.

In the formula (V), as a protecting group in the optionally protected hydroxyl group shown by $R^4$, use is preferably made of protecting groups of carboxyl group described later.

In the formula (V), the amino acid in the optionally protected amino acid residue in the amino acid sequence shown by X' has the same meaning as that in the amino acid residue in the afore-mentioned amino acid sequence shown by X.

In the formula (V), as the protecting group in the optionally protected amino acid residue, mention is made of known protecting groups employed for protecting amino group, carboxyl group or hydroxyl group in peptide synthesis. These are protecting groups which can be removed by, for example, hydrolysis, hydrogenolysis, reduction, aminolysis or hydrazinolysis.

Examples of the amino-protecting groups include urethane-type protecting groups (e.g. benzyloxycarbonyl, t-butoxycarbonyl, allyloxycarbonyl, t-amyloxycarbonyl, isobornyloxycarbonyl, 4-methoxybenzyloxycarbonyl, 2-chlorobenzyloxycarbonyl, adamantyloxycarbonyl, 9-fluorenylmethyloxycarbonyl, 2,2,2-trichloroethyloxycarbonyl, or the like), acyl-type protecting groups (e.g. $C_{1-6}$ lower fatty acid residues optionally having such a substituent as halogen, e.g. formyl, acetyl, propyl, trifluoroacetyl, chloroacetyl, or the like, phthalyl, tosyl, 2-nitrosulfenyl, 4-methoxy-2-nitrosulfenyl, benzoyl, or the like), and alkyl-type protecting groups (e.g. trityl, benzyl or the like).

Among these, urethane-type protecting groups are especially preferable.

Carboxyl groups are protected by converting them into, for example, an amido group, a hydrazido group or ester. Preferable amido groups or hydrazido groups are those substituted with a suitable substituent. Preferable amido groups are those substituted with a $C_{7-19}$ aralkyl group optionally substituted with, for example, an alkoxy group (e.g. 3,4-dimethoxybenzyl or bis-(p-methoxyphenyl)-methyl). Preferable hydrazido groups are those substituted with, for example, a $C_{1-6}$ alkyloxycarbonyl group optionally substituted with $C_{6-12}$ aryl group (e.g. phenyl, p-biphenylyl, etc.) or halogen (e.g. fluorine, chlorine, bromine, etc.) (e.g. benzyloxycarbonyl, trichloroethyloxycarbonyl, tert-butyloxycarbonyl group, 2-(p-biphenylyl)-isopropyloxycarbonyl, etc.), a halogenated $C_{2-6}$ alkanoyl group (e.g. trifluoroacetyl group, etc.) and a $C_{7-19}$ aralkyl group (e.g. trityl, etc.), among others. Further, the carboxyl groups may be protected as esters with an optionally substituted lower alcohol (e.g. methanol, ethanol, cyanomethyl alcohol, benzoylmethyl alcohol, tert-butanol, etc.), aralkanol [e.g. benzyl alcohol or benzhydrols (e.g. benzhydrol, p-nitrobenzyl alcohol, p-methoxybenzyl alcohol, 2,4,6-trimethylbenzyl alcohol, etc.) optionally substituted with, for example, a lower alkyl group, a lower alkoxy group or a halogen atom], phenol and thiophenol optionally substituted with an electron withdrawing group (e.g. thiophenol, thiocresol, p-nitrothiophenol, 2,4,5- and 2,4,6-trichlorophenol, p-cyanophenol, p-methanesulfonyl phenol, etc.), and further, with N-hydroxyimide (e.g. N-hydroxysuccinimide, N-hydroxyphthalimide, etc.), N-hydroxypiperidine, 8-hydroxyquinoline or the like.

As the special protecting group of a carboxyl group, which can be removed under neutral reaction conditions, mention is made of hydrocarbyl-silyl-ethyl, for example, 2-(trimethylsilyl)-ethyl (described in German Patent Application Laid-Open No. 2,706,490).

A hydroxyl group can be protected with, for example, acylation or etherification.

The especially preferable acyl group in the case of acylation is a group derived from carbonic acid (e.g. benzyloxycarbonyl group or ethyloxycarbonyl group). For etherfication, benzyl group, tetrahydropyranyl or tert-butyl, for example, is preferable. And, for the protection of a hydroxyl group, 2,2,2-trifluoro-1-tert-butyloxycarbonylamino-ethyl or 2,2,2-trifluoro-1-benzyloxycarbonylamino-ethyl [Weygand, Chem. Ber., Vol. 100 (1967), pp 3838–3849] is preferably employed.

TAN-1511A, TAN-1511B and TAN-1511C of the present invention can be produced by cultivating a microorganism capable of producing TAN-1511A, TAN-1511B or TAN-1511C in a culture medium to produce and accumulate these compounds in the culture broth, then by recovering them.

As a microorganism producing TAN-1511A, B or C employed in the production method of this invention, mention is made of any microorganism belonging to the genus Streptosporangium which is capable of producing TAN-1511A, B or C. As a practical example of them, mention is made of Streptosporamgium AL-23456 strain isolated from soils collected in Fukui Prefecture. Taxonomical properties of this strain investigated in accordance with the method described in "International Journal of Systematic Bacteriology" Vol. 16, pp 313–340 (1966) are as follows. Incidentally, observations on various culture media are conducted in a conventional manner by incubating at 28° C. for 14 days, unless otherwise specified.

(I) Morphological characteristics

Aerial mycelia are of branched type. While the formation of aerial mycelia is not observed until the end of the second week, it is slightly observed at the fourth week presenting while color. At the top of aerial mycelia, globular sporangium ($\phi$6–8 μm) are often observed. Sporangiospores are ovoid ($\phi$0.5–0.8×0.8–1.0 μm). On the aerial mycelia are observed a number of purple needle-like crystals.

(II) Growth states on various culture media

The extent of growth on various culture media (G), growth and color of aerial mycelia (AM), color of reverse (R) and soluble pigment and color tone (SP) are set forth in Table 1. Standard color signs in parenthesis are based on The Color Harmony Manual, 4th edition (Container Corporation of America, 1958).

TABLE 1

| | | |
|---|---|---|
| (a) Sucrose · nitrate agar | G | Scant, light ivory(2ca) |
| | AM | None |
| | R | Ivory(2ea) |
| | SP | None |
| (b) Glucose · asparagine agar | G | Poor, ivory(2ea) restricted |
| | AM | None |
| | R | Ivory(2ea) |
| | SP | None |
| (c) Glycerol · asparagine agar | G | Poor, ivory(2ea) restricted |
| | AM | None |
| | R | Ivory(2ea) |

TABLE 1-continued

| | | |
|---|---|---|
| (d) Starch · inorganic salts agar | SP | None |
| | G | Rather poor, ivory(2ea) restricted |
| | AM | None |
| | R | Pale yellowish gray(2ge) |
| (e) Tyrosine agar | SP | None |
| | G | Rather poor, pale yellowish brown(2ga) |
| | AM | None |
| | R | Ivory(2ea) |
| (f) Nutrient agar | SP | None |
| | G | Moderate, pale yellowish brown(2ga)-(2ic) |
| | AM | None |
| | R | pale yellowish(2ga)-pale brown(2ic) |
| (g) Yeast · malt agar | SP | None |
| | G | Good, yellowish gray (21e)-brown(2ne) restricted |
| | AM | None |
| | R | Pale yellow(2ic)-darkbrown(2ng) |
| (h) Oatmeal agar | SP | None |
| | G | Good, pale yellowish gray(2gc) restricted |
| | AM | None |
| | R | Pale yellowish gray (2gc)-pale brown(2ic) |
| (i) Peptone · yeast · iron agar | SP | None |
| | G | Scant, pale brown(2ic) restricted |
| | AM | None |
| | R | Pale brown(2ic) |
| | SP | None |

(III) Physiological properties
 (a) Growth temperature range: 12°–38° C.
  Optimal growth temperature range: 19°–32° C.
 (b) Reduction of nitrates: Negative
 (c) Liquefaction of gelatin: Negative
  (Glucose.peptone.gelatin medium)
 (d) Starch hydrolysis: Positive
 (e) Coagulation of skimmed milk: Negative
  Peptonization of skimmed milk: Negative
 (f) Production of melanoid pigment
  Tyrosine agar: Negative
  Peptone.yeast.iron agar: Negative
 (g) Assimilation of carbon sources (Pridham.Gottlieb agar medium)
  L-arabinose: ± D-xylose: ± D-glucose: +
  D-fructose: ± sucrose: – inositol: –
  L-rhamnose: ± Raffinose: – D-Mannitol: ±
  Control: ±–
   (Note) ++: relatively good growth
   +: growth is observed
   ±: difficult in judging + or –
   –: no growth
 (h) Others
  No motility was observed in sporangiospore
(IV) Chemical taxonomical properties
 Employing a medium (pH 7.0) containing glucose (1%), trypton (1%) and yeast extract (0.6%), AL-23456 strain was incubated at 28° C. for 3 days. Then, in accordance with the method described in "Housenkin No Douteizikken Hou" compiled by The Society for Actinomycetes Japan (1988), living mycelia and cell wall fractions were prepared.

The following analysis was conducted in accordance with the method described in the above-mentioned literature reference.
a) Amino acid analysis
 The cell wall fraction was subjected to hydrolysis with 6N HCl at 105° C. for 18 hours. The hydrolyzate was subjected to analysis by the high performance liquid chromatography method (Takahashi, Y. et al: J. General and Applied Microbiology 35:27–32, 1989). As the result, muramic acid, glucosamine, alanine and glutamic acid were observed, while no glycine was recognized. The diaminopimelic acid was meso-compound.
b) Analysis of reducing sugar
 Whole cell body and cell wall of cell body were respectively subjected to hydrolysis with 2N hydrochloric acid at 105° C. for 3 hours. The hydrolyzate was subjected to analysis by the high performance liquid chromatography method (Yokota, A and Hasegawa, T: J. General and Applied Microbiology 34:445–449, 1988). As the result, presence of glucosamine, madulose, mannose, arabinose, xylose and glucose was observed as the composition of constituent sugars of the whole cell body, while, in the cell wall of cell body, no sugar was detected.
c) Analysis of menaquinone (Tamaoka, J. et al.: J. Applied Bacteriology 54:31–36, 1983)
 Dry cell bodies were subjected to extraction with a mixture of chloroform and methanol (2:1 v/v) at room temperature for 18 hours. The extract was concentrated, which was subjected to analysis by the high performance liquid chromatography method (Tamaoka, J. et al.: J. Applied Microbiology 54:31–36, 1983). As the result, MK-9($H_2$) and MK-9($H_6$) were confirmed as the composition of menaquinone, the former being prevalent.

From the above results, the properties of the present strain were revealed as follows: aerial mycelia are formed at relatively late stage (after about 4 weeks); while at the top of the aerial mycelia globular sporangium was formed, no motility is observed in the spore; and diaminopimelic acid of the cell wall is meso-type, glycine is not detected, cell wall type is III, madulose is present and menaquinone is of MK-9($H_2$) prevalent; thus it is clear that the present strain belongs to the genus Streptosporangium, and, hence, the strain is named Streptosporangium sp. AL-23456.

AL-23456 strain has been deposited under the accession number of IFO 15365 at the Institute for Fermentation, Osaka (IFO) since Aug. 27, 1992. Also this strain has been deposited at Fermentation Research Institute, Agent of Industrial Science and Technology, Ministry of International Trade and Industry (FRI) under the Budapest Treaty bearing the accession number of FERM BP-4086.

TAN-1511A-, B- or C-producing strains belonging to the genus Streptosporangium are, like any other strains of Actinomycetes, susceptible to variation by means of, for example, irradiation of ultraviolet- or X-ray, single cell separation, various variation processes, or any other means. These variants thus obtained or those of spontaneous mutation are far from being determined as belonging to a substantially different species when comparing them with AL-23456 in their taxonomical properties, and all of those capable of producing said compounds can be employed in the practice of this invention.

While the culture medium to be employed for cultivation of TAN-1511A-, B- or C- producing strains may be a liquid or solid one, so long as it contains nutrient sources utilizable by these strains, a liquid culture medium is preferable when the cultivation is conducted on a large scale. In the medium, there may be incorporated, as required, carbon sources, nitrogen sources, inorganic substances and trace nutrients. As carbon sources, use is made of, for example, glucose, lactose, sucrose, maltose, dextrin, starch, glycerol, mannitol, sorbitol, fats & oils (e.g. soybean oil, lard oil, chiken oil, etc.), n-paraffin, etc. As nitrogen sources, use is made of, for example, meat extract, yeast extract, dried yeast, soybean flour, corn steep liquor, peptone, cotton seed powder, blackstrap molasses, urea, ammonium salts (e.g. ammonium sulfate, ammonium chloride, ammonium nitrate, ammonium acetate, etc.), among others. Further, salts of sodium potassium, calcium, magnesium, iron, manganese, zinc, cobalt, nickel or the like; salts of phosphoric acid, boric acid or the like; salts of organic acids such as acetic acid, propionic acid or the like are suitably employed. The medium may further be incorporated with amino acids (e.g. glutamic acid, aspartic acid, alanine, lysine, methionine, proline, etc.), peptides (e.g. dipeptide, tripeptide, etc.), vitamins (e.g. $B_1$, $B_2$, nicotinic acid, $B_{12}$, C etc.), nucleic acids, (e.g. purine, pyridine, their derivatives, etc.). Needless to state, for the purpose of adjusting pH of the medium, an inorganic or organic acid or alkali, or a buffering agent may be added, or, as an antifoaming agent, an adequate amount of fats & oils, a surfactant or the like may be supplemented. In the case of liquid culture, pH of the medium is preferably neutral, especially from 5.5 to 8. Culture temperature ranges preferably from about 24° C. to 30° C. Preferable culture period ranges from 48 to 168 hours.

Methods of recovering the desired compound TAN1511A, B or C from the culture broth are described below. Since TAN-1511A, B or C is an acidic fat-soluble substance, a conventional method utilizing this property can be employed, for example. As these compounds are contained in the filtrate, such a refining procedure as follows is employed, for example. To start with, a filter aid or the like is added to the culture broth, which is subjected to filtration. The pH of the filtrate is adjusted to a range of 1.0 to 5.0, preferably 1.5 to 4. Then, TAN-1511A, B or C is extracted with a water-immiscible organic solvent, for example, a halogenated hydrocarbon such as dichloromethane, chloroform or the like, esters such as ethyl acetate, butyl acetate or the like, methyl isobutyl ketone or butanol, among others. The organic solvent layer is subjected to extraction with a dilute alkaline aqueous solution to have TAN-1511A, B or C transferred into the aqueous layer. The aqueous layer was again adjusted to acidic, which is subjected to 10 extraction with the aforementioned organic solvent to have TAN-1511A, B or C transferred into the organic solvent layer. The organic solvent layer was washed with water, which is then concentrated to give crude products containing TAN-1511A, B or C, respectively. For obtaining pure TAN-1511A, B or C by refining these crude products, various chromatographic means are advantageously employed. As the carriers, use is made of silica-gel, crystalline cellulose, an adsorptive resin such as Diaion HP-20 or SP-207 (Mitsubishi Kasei Co., Ltd., Japan), Amberlite XAD-I or II (Rohm & Haas Co., U.S.A) or a carrier for gel-filtration such as Sephadex LH-20 (Pharmacia, Sweden), Toyopal HW-40 (Tosoh Co., Ltd., Japan), and these carriers are used in conventional column chromatographic means. For eluting active substances from the column, use is made of a suitable organic solvent, for example, hydrocarbons such as n-hexane, toluene or the like, halogenated hydrocarbons such as chloroform, dichloromethane, dichloroethane or the like, ketones such as ketone or the like, esters such as ethyl acetate or the like, alcohols such as methanol, ethanol or the like, organic acids such as acetic acid, formic acid or the like, among others. The organic solvent may be used singly or a mixture of two or more of them. Further, a mixed solvent at an appropriate ratio, for example, a water-miscible organic solvent (e.g. methanol, ethanol, acetone, acetonitrile, etc.) and water, a dilute alkaline (e.g. sodium hydroxide, potassium hydroxide, sodium hydrogencarbonate, etc.) water, a dilute acidic (e.g. acetic acid, formic acid, phopshoric acid, etc.) water, or a buffer solution (e.g. acetic acid buffer solution, phosphate buffer solution or the like), is used, among others.

And, in some cases, TAN-1511A, B or C can be purified also by means of a high performance liquid chromatography (HPLC) for separation. As the carriers, use is advantageously made of octadecyl silane (ODS) type, aminopropyl silane type, polyamine type and silica gel type ones. In the case of employing ODS for example, a mixture of methanol or acetonitrile and an aqueous solution containing salts.

The eluate containing the active substances eluted with an organic solvent is concentrated, or, in the case where the eluate contains an aqueous solution, it is subjected to extraction with a suitable one of the afore-mentioned water-immiscible organic solvents, then the extract is concentrated, and the concentrate is pulverized, or dissolving the concentrated in a suitable crystallization solvent, for example, hydrocarbons such as petroleum benzin, petroleum ether, n-hexane or the like, ethers such as diethyl ether, diisopropyl ether or the like, halogenated hydrocarbons such as chloroform, dichloroethane or the like, esters such as ethyl acetate or the like, alcohols such as methanol, ethanol or the like, among others, singly or a suitable mixture of them, then leaving the solution standing at a cool place, to thereby afford crystals.

Physico-chemical properties of TAN-1511A, B and C thus obtained as above are shown below.

In the present specification, $^1$H-NMR spectrum is recorded on a Bruker AM500 (500 MHz) type spectrometer or Varian Gemini 200 (200 MHz) type spectrometer using tetramethyl silane as the internal standard, expressing all the δ values in ppm.

Symbols used in the present specification are of the following meaning.

s; singlet, d: doublet, t: triplet, q: quartet, dd: double doublet, dt: double triplet, m: multiplet, br: broad Common properties of TAN-1511A, B and C 1) Thin-layer chromatography (TLC):

Carrier: silica gel 60 $F_{254}$ (0.25 mm, E. Merck AG, Germany)

Developing solvent: chloroform:methanol:water (6:3:0.5)
Rf: A, 0.32, B, 0.28, C, 0.48

Developing solvent: ethyl acetate:isopropyl alcohol:water (10:5:2.5)
Rf: A, 0.27, B, 0.23, C, 0.34

2) High performance liquid chromatography (HPLC):

Column: YMC-Pack A-602 $NH_2$ (Yamamura Chemical Laboratories, Japan)

Mobile phase: 85% methanol/0.02M phosphate buffer (pH 4.8)

Flow rate: 1.0 ml/min.

Detecting method: UV, 214 nm

Retention time [$t_R$(min.)]: A, 14.6, B, 15.8, C, 15.4

3) Solubility:

Soluble; dimethyl sulfoxide, isobutyl alcohol

Hardly soluble; methanol, ethyl acetate

Insoluble; water, hexane

4) Color reaction:

Positive; phosphorus molybdate, iodine, 50% sulfuric acid

Negative; Greig-Leaback, Sakaguchi and Dragendorff
5) Acidic, neutral or basic:
acidic Respective properties of TAN-1511A, B and C are given below.

Figure 2:
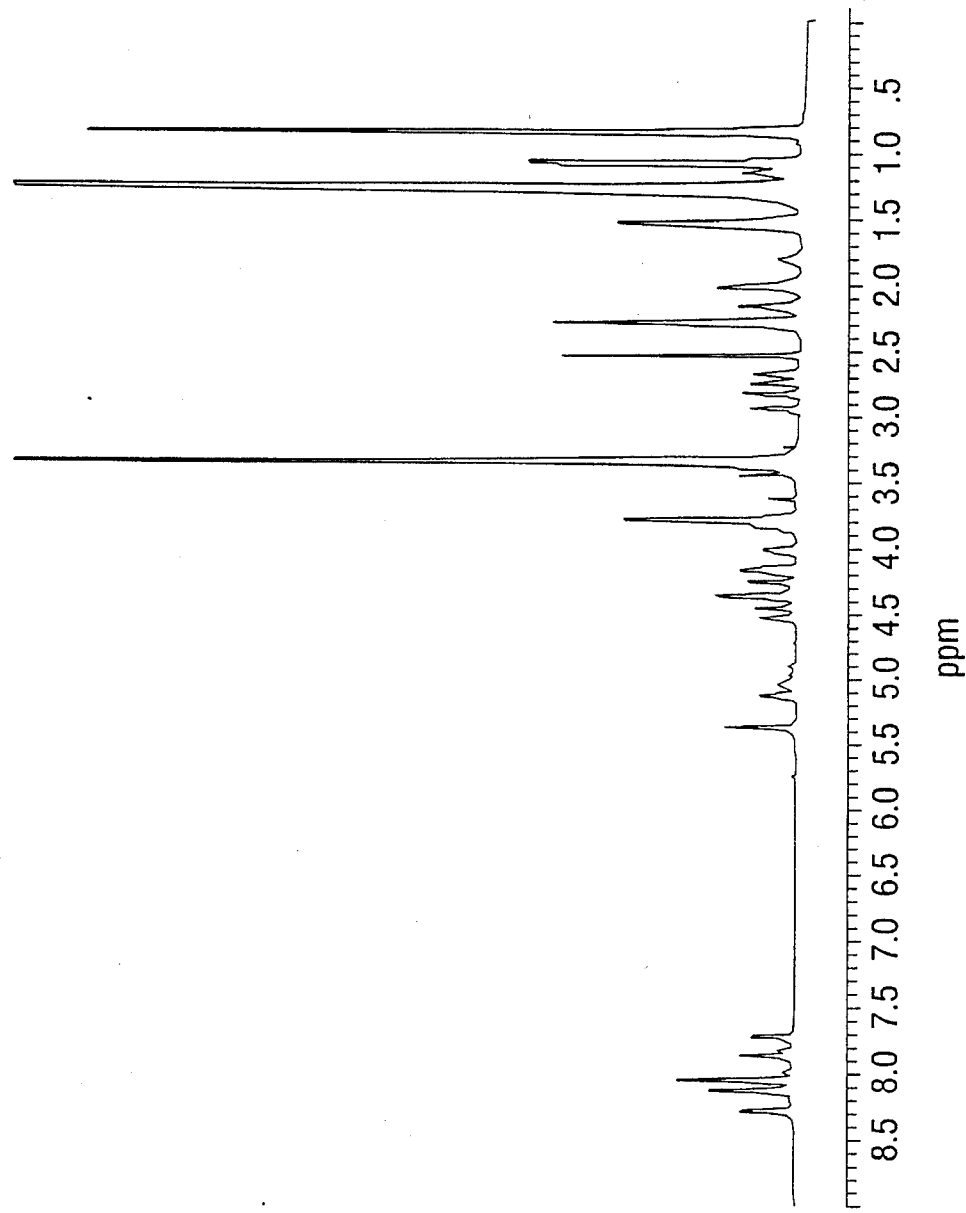
FIG. 2 is a $^1$H-NMR spectrum of TAN-1511 A.
Figure 3:
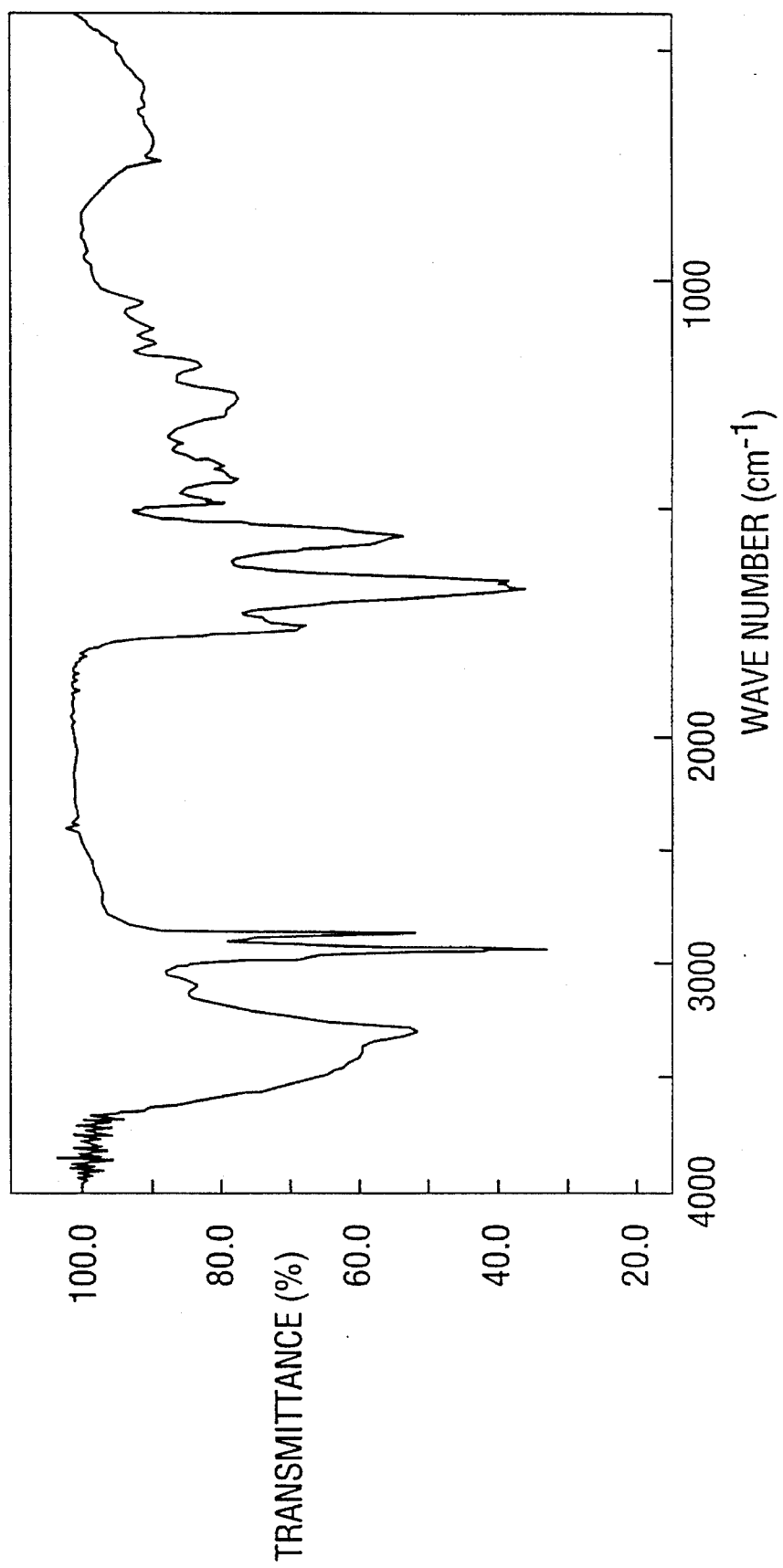
FIG. 3 is an IR spectrum of TAN-1511 B.
Figure 4:
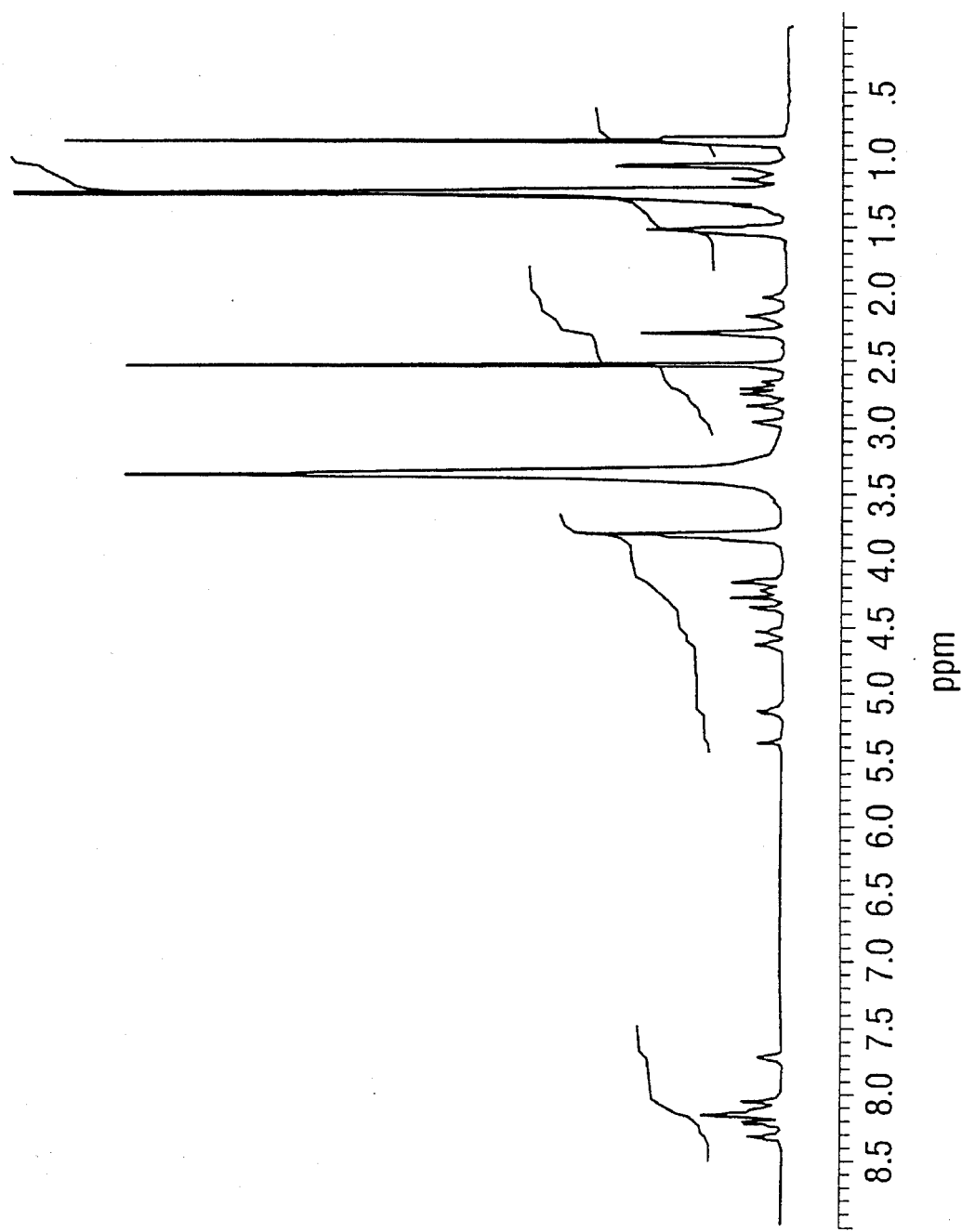
FIG. 4 is a $^1$H-NMR spectrum of TAN-1511 B.
Figure 5:
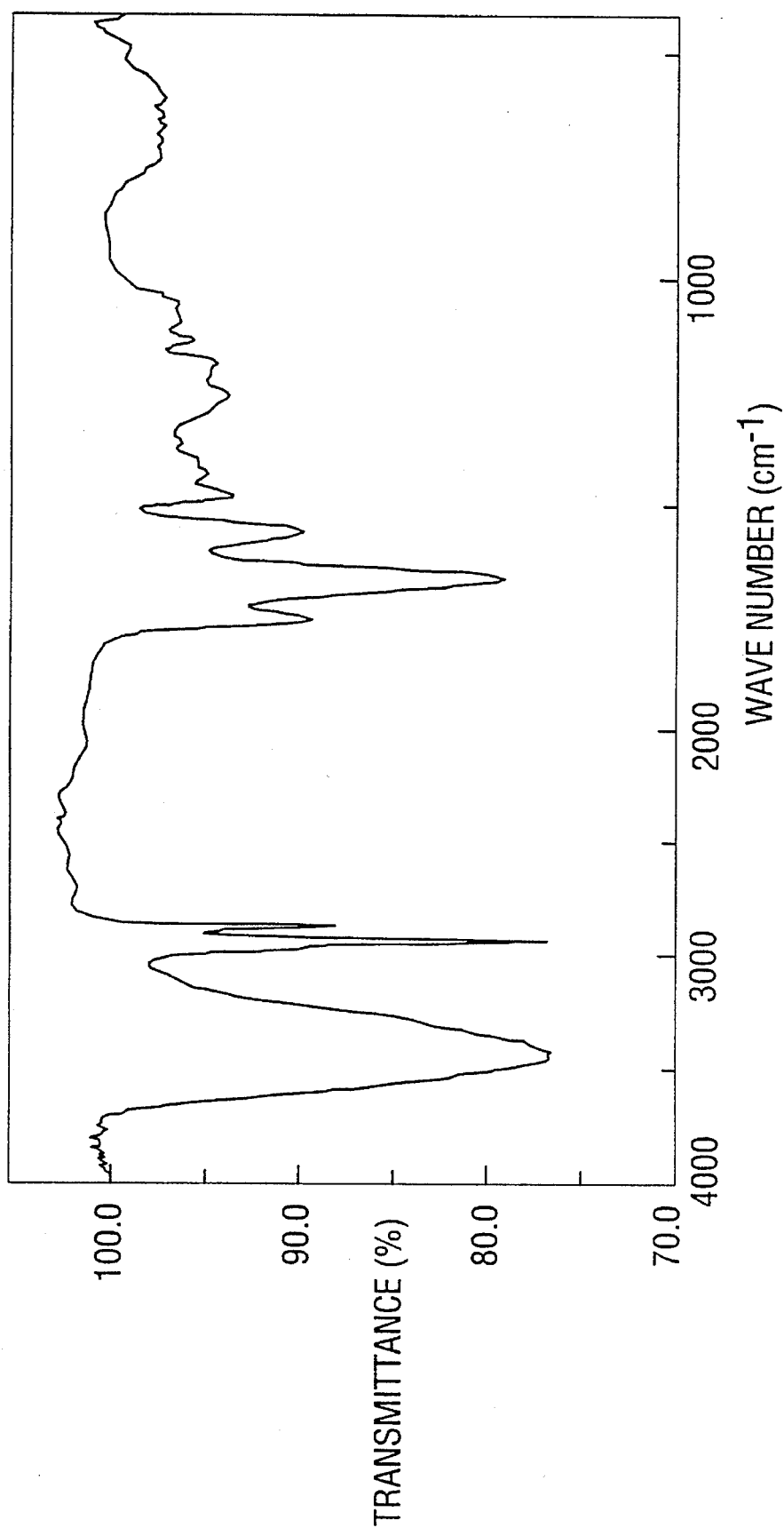
FIG. 5 is a $^1$H-NMR spectrum of TAN-1511 C.

TAN-1511A
1) Appearance: White powder
2) UV spectrum (in methanol): End absorption (<200 nm)
3) IR spectrum (in KBr): Main absorption wavenumbers are shown (cm$^{-1}$), [FIG. 1]. 3310, 2955, 2925, 2850, 1740, 1655, 1540, 1465, 1405, 1385, 1245, 1165, 1115, 1030
4) FAB-MS spectrum: Main (M+Na) peaks are shown (m/z). 1449, 1447, 1435, 1433, 1421, 1419, 1407, 1405
5) $^1$H NMR spectrum (500 MHz, in DMSO-d$_6$): δppm, [FIG. 2] 0.87(ca.12H,m), 1.08(3H,d), 1.11(3H,d), 1.16(ca.2H,m), 1.26(ca.60H,br), 1.52(6H,m), 1.78(1H,m), 1.95(1H,m), 2.00(ca.2H,m), 2.15(2H,m), 2.28(6H,m), 2.66(1H,dd), 2.73(1H,dd), 2.83(1H,dd), 2.94(1H,dd), 3.70–3.86(6H,m), 3.99(1H,m), 4.12(1H,dd), 4.16(1H,m), 4.22(1H,dd), 4.31(1H,br d), 4.34(1H,dd), 4.42(1H,dt), 4.50(1H,dt), 5.11(1H,m), 5.34(ca.1H,t), 7.72(1H,d), 7.86(1H,d), 8.04(1H,d), 8.06(1H,d), 8.11(1H,t), 8.13(1H,t), 8.29(1H,t)
6) Amino acid analysis (6N HCl, 105° C., 14 hours): L-threonine (2 mol.). L-glutamic acid (1 mol.), glycine (3 mol.)
7) C-terminal analysis (hydrazinolysis method): threonine TAN-1511B
1) Appearance: White powder
2) UV spectrum (in methanol): End absorption (<200 nm)
3) UV spectrum (in KBr): Main absorption wavenumbers are shown (cm$^{-1}$), [FIG. 3] 3310, 2955, 2920, 2850, 1735, 1655, 1540, 1470, 1415, 1385, 1250, 1170
4) FAB-MS spectrum: Main (M+Na) peaks are shown (m/z). 1462, 1460, 1448, 1446, 1434, 1432, 1420, 1418
5) $^1$H NMR spectrum 500 MHz, in DMSO-d$_6$): δppm [FIG. 4] 0.87(ca.12H,m), 1.06(3H,d), 1.16(ca.2H,m), 1.26(ca.65H,br), 1.52(6H,m), 2.00(ca.1H,m), 2.15(2H,m), 2.29(4H,m), 2.53(1H, overlapped with solvent signal), 2.67(1H,dd), 2.72(1H,dd), 2.73(1H,dd), 2.83(1H,dd), 2.95(1H,dd), 3.70–3.85 (8H,m), 4.12(2H,m), 4.18(1H,br d), 4.23(1H,m), 4.31(1H,dd), 4.50(1H,dt), 4.60(1H,m), 5.11(1H,m), 5.34(ca.0.5H,t), 7.71(1H,d), 8.05(1H,d), 8.10(1H,d), 8.15(3H,m), 8.21(1H,d), 8.31(1H,t)
6) Amino acid analysis (6N HCl, 105° C., 12.5 hours): L-aspartic acid (1 mol.), L-threonine (1 mol.), glycine (4 mol.), L-alanine (1 mol.)
7) C-terminal analysis (hydrazinolysis method): threonine TAN-1511C
1) Appearance: White powder
2) UV spectrum (in methanol): End absorption (<200 nm)
3) IR spectrum (in KBr): Main absorption wavenumbers are shown (cm$^{-1}$), [FIG. 5]. 3430, 2925, 2855, 1740, 1650, 1540, 1460, 1410, 1240, 1165, 1115
4) FAB-MS spectrum: Main (M+Na) peaks are shown (m/z). 1443, 1441, 1429, 1427, 1415, 1413, 1401, 1399
5) Amino acid analysis (6N HCl, 105° C., 13.5 hours): L-aspartic acid (1 mol.), L-proline (1 mol.), glycine (3 mol.), L-leucine (1 mol.)
6) C-terminal analysis (hydrazinolysis method): leucine The TAN-1511 complex obtained by Working Example 2 described later was subjected to mild alkali decomposition to have the ester portion hydrolyzed to obtain a mixture of fatty acids. The mixture was subjected to identification by means of HPLC to detect pentadecanoic acid, isopalmitic acid, palmitic acid, oleic acid and heptadecanoic acid. Further, this deesterified compound was subjected to hydrolysis with hydrochloric acid. Then, the resulting mixture of fatty acids was subjected to analysis to detect lauric acid, tridecanoic acid isomyristic acid and myristic acid.

From the foregoing data and other spectrum data, the structural formulae of TAN-1511A, B and C were estimated as follows.

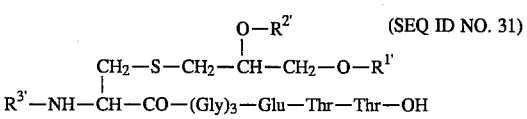

(SEQ ID NO. 31)

wherein R$^{1'}$, R$^{2'}$ and R$^{3'}$ each stand for a mixed higher fatty acid residue.

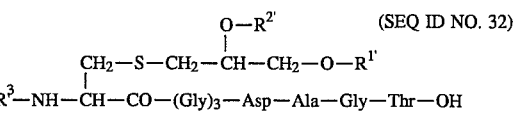

(SEQ ID NO. 32)

wherein R$^{1'}$, R$^{2'}$ and R$^{3+}$ each stand for a mixed higher fatty acid residue.

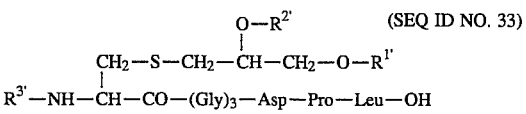

(SEQ ID NO. 33)

wherein R$^{1'}$, R$^{2'}$ and R$^{3'}$ each stand for a mixed higher fatty acid residue.

The compound represented by the formula (I) or a salt thereof can be produced by, for example, subjecting a compound represented by the formula (V) or a salt thereof to N-acylation, then by subjecting the resultant, when desired, to deprotecting reaction.

The N-acylation can be conducted by allowing a starting compound having a free amino group to react with an acylating agent containing an aliphatic acyl group shown by R$^3$, for example, a reactive derivative of carboxylic acid.

As the reactive derivative of carboxylic acid, use is made of, for example, acid halide, acid anhydride, a mixed acid anhydride, amido compound, active ester and active thioester. Practical examples of the reactive derivatives are as follows.

1) Acid halides

As the acid halide, use is herein made of, for example, acid chloride, acid bromide or the like.

2) Acid anhydrides, mixed acid anhydrides

As the acid anhydride, use is herein made of, for example, a mixed acid anhydride of monoalkyl carbonates, a mixed acid anhydride consisting of fatty acid carboxylic acid (e.g. acetic acid, valeric acid, hexanoic acid, lauric acid, myristic acid, palimitic acid, etc.), a mixed acid anhydride consisting of aromatic carboxylic acid (e.g. benzoic acid), symmetrical acid anhydrides, among others.

3) Amide compounds

As the amide compound, use is herein made of a compound in which acyl group is bonded to the nitrogen in the ring, for example, pyrazole, imidazole, 4-substituted imidazole, dimethyl pyrazole, benzotriazole or the like.

4) Active esters

As the active ester, use is herein made of, for example, besides esters such as methyl ester, ethyl ester, methoxymethyl ester, propargyl ester, 4-nitrophenyl ester, 2,4-dinitrophenyl ester, trichlorophenyl ester, pentachlorophenyl ester, mesyl phenyl ester or the like, esters with 1-hydroxy-1H-2-pyridone, N-hydroxysuccinimide, N-hydroxyphthalimide, 1-hydroxybenzotriazole (HOBT) or the like.

5) Reaction derivatives produced by the reaction of carboxylic acid with carbodiimide As the carbodiimide, use is herein made of a condensing agent such as N,N'-dicyclohexyl carbodiimide (DDC), 1-ethyl-3-(3-dimethylaminopropyl)-carbodiimide hydrochloride (WSC), N,N'-diisopropyl carbodiimide (DIC), or the like.

Various reactive derivatives mentioned as above are adequately selected depending on the kinds of carboxylic acid.

While these reactive derivatives are sometimes isolated, they may, depending on cases, be subjected to the reaction, without isolation, with amino group in the reaction vessel.

The above-mentioned N-acylation may be conducted in the presence of a base. As the base, use is made of, for example, aliphatic tertiary amine (e.g. trimethylamine, triethylamine (TEA), tripropylamine, N,N'-diisopropylethylamine, etc.), tertiary amine such as N-methyl piperidine, N-methyl pyrrolidine, cyclohexyl dimethyl amine, N-methyl morpholine, etc., dialkyl amine such as di-n-butyl amine, dicyclohexyl amine, etc., aromatic amine such as pyridine, collidine, etc., hydroxide or carbonate with alkali metal such as lithium, sodium, potassium or the like or with alkaline earth metal such as calcium, magnesium or the like, among others. Among these bases, those in liquid state can be used to serve dual purposes of the base and solvent.

In N-acylation, a reaction derivative of carboxylic acid is employed usually in an amount of one mole relative to one mole of the starting compound, but it may be used in excess amount unless giving adverse effects on the reaction. While the amount of the base to be employed varies with kinds of the starting compound and the reactive derivative of carboxylic acid or with other reaction conditions, it ranges usually from about 1 mole to 5 moles, preferably from about 1 to 3 moles relative to one mole the compound.

N-acylation is conducted usually in a solvent. Examples of the solvent include ethers such as dioxane, tetrahydrofuran (THF), diethyl ether, diisopropyl ether, propylene oxide or butylene oxide, esters such as ethyl acetate or ethyl formate, halogenated hydrocarbons such as chloroform, dichloromethane (DCM), 1,2-dichloroethane or 1,1,1-trichloroethane, hydrocarbons such as benzene, toluene or n-hexane, amides such as N,N-dimethylformamide (DMF) or dimethyl acetamide, and nitrile such as acetonitrile. These solvents are used singly or as a mixture of a suitable ratio.

While the reaction temperatures are not especially restricted so long as the reaction proceeds, the reaction is conducted usually in a range from −50° C. to 150° C., preferably from −30° C. to 80° C. While the reaction time varies with the starting materials, bases, reaction temperatures and kinds of solvents then employed, it ranges usually from several ten minutes to several ten hours. Depending on cases, the reaction requires several ten days.

The above-mentioned deprotection reaction is conducted by a per se known method, for example, the conventional method in the field of peptide chemistry. [cf. Synthetic Chemistry Series, Peptide Synthesis, authors: IZUMIYA Nobuo, UNO Motonori, KATO Tetsuo & AOYAGI Haruhiko; Published by Maruzen Co. Ltd. 1975 in Japan].

Deprotection reaction on the amino group protected with a urethane-type protecting group is conducted by bringing the amino group into contact with an acid in the absence of solvent or in a solvent which gives no adverse influence on the reaction. As the solvent, use is made of halogenated hydrocarbons (e.g. dichloromethane, chloroform, 1,2-dichloroethane, etc.), alcohols (e.g. methanol, ethanol, etc.), water and a mixture of them in an appropriate ratio. This reaction is conducted by bringing the compound or a salt thereof into contact with an acid. As the acid, use is made of, for example, haloacetic acid (e.g. trifluoroacetic acid, etc.), hydrohalogenic acid (e.g. hydrochloric acid, hydrobromic acid, etc.), among others. It is advantageous that N-benzyloxycarbonyl group and N-4-methoxybenzyloxycarbonyl group are removed by catalytic hydrogenation by using, for example, palladium catalyst (e.g. palladium carbon, palladium-barium sulfate, palladium black, etc.) or rhodium catalyst. In this case, a known solvent, for example, cyclic ether (e.g. tetrahydrofuran, etc.), alcohols (e.g. methanol, ethanol, etc.) etc., or, depending on cases, a mixture of cyclic ether and other inert solvents [e.g. lower aliphatic acid amide (e.g. dimethylformamide, etc.) etc.] is used.

N-9-Fluorenylmethyloxycarbonyl group is removed advantageously by using an organic amine, for example, diethylamine, piperidine, morpholine, 4-dimethylaminopyridine or dicyclohexylamine. The reaction is conducted in a solvent which gives no adverse reaction on the reaction. As the solvent, use is made of, for example, amides (e.g. dimethylformamide, acetamide, etc.), alcohols (e.g. methanol, ethanol, etc.), halogenated hydrocarbons (e.g. chloroform, dichloromethane, etc.), etc., or a mixture of them in an appropriate ratio.

It is advantageous that, N-2,2,2-trichloroethyloxycarbonyl group is removed by using a metal (e.g. zinc, etc.) together with an organic carboxylic acid (e.g. acetic acid, propionic acid, etc.). The reaction is conducted in a solvent which gives no adverse influence on the reaction. As the solvent, use is made of the above-mentioned carboxylic acid, alcohols (e.g. methanol, ethanol, etc.) water or a mixture of them in an appropriate ratio.

For example, deacylation of the acylated hydroxyl group can be conducted by hydrolysis with an acid, for example, haloacetic acid (e.g. trifluoroacetic acid, etc.), hydrohalogenic acid (e.g. hydrochloric acid, hydrobromic acid, etc.) or the like in a suitable solvent.

Elimination of O-benzyl is performed advantageously by catalytic hydrogenation with, for example, a palladium catalyst such as palladium-carbon, palladium/barium sulfate and palladium black, or a rhodium catalyst, using, in this case, a known solvent, for example, cyclic ether (e.g. tetrahydrofuran, etc.) as a mixture with other inactive solvents [e.g. lower aliphatic acid amide (dimethylformamide or the like) etc.].

Elimination of O-tetrahydropyranyl or O-tert-butyl group can be performed, like in the above-mentioned deacylation, by hydrolysis with an acid.

Elimination of a carboxyl-protecting group can be performed, like in the above-mentioned case, by hydrolysis with an acid. And, benzyl ester, for example, can be eliminated by catalytic hydrogenation like in the case of the above-mentioned elimination. The above-mentioned 2-(trimethylsilyl)-ethyl can be eliminated by the action of, for example, a salt of hydrofluoric acid, for example, especially a salt of base having quaternary nitrogen with hydrofluoric acid (e.g. tetraethyl ammonium fluoride, etc.) in a suitable solvent under neutral conditions.

The compound represented by the general formula (V) or a salt thereof can be produced by adequate application of, for example, the method described in JPA H5(1993)-181735.

The compound (I) or a salt thereof of the present invention can be produced also by subjecting a compound represented by the general formula (VI)

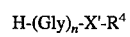    (VI)

wherein X', $R^4$ and n are of the same meaning as defined (SEQ ID Nos. 70–88) above, or a salt thereof and a compound represented by the general formula (VII)

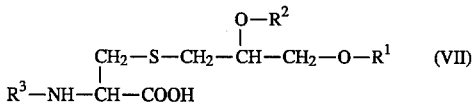

wherein $R^1$, $R^2$ and $R^3$ are of the same meaning as defined above, or a salt thereof to condensation, followed by, when desired, subjecting the condensate to the above-mentioned deprotection reaction.

The condensation can be conducted in the presence of a solvent. The solvent can be selected from those known as being employable for peptide condensation reaction. Examples of the solvent include amides such as anhydrous or water-containing formamide, dimethylformamide, N-methyl pyrrolidone, etc., sulfoxides such as dimethyl sulfoxide, etc., aromatic amines such as pyridine, etc., halogenated hydrocarbons such as chloroform, dichloromethane, etc., ethers such as tetrahydrofuran, dioxane, etc., nitriles such as acetonitrile, etc., esters such as ethyl acetate, ethyl formate, etc., or a mixture of them in an appropriate ratio.

The reaction temperatures can be adequately selected from the range known as being employable for peptide linkage forming reaction, specifically, for example, usually from about 20° C. to 40° C.

The reaction time can be adequately selected from the range known as being required for peptide linkage formation reaction, specifically, for example, from about several minutes to about 48 hours.

The compound (VI) or a salt thereof can be produced by adequately applying a per se known method for example the method described in JPA H5(1993)-181735.

The compound (VII) or a salt thereof can be produced by a per se known method, for example, the method described in Hoppe-Seyler's Zeitschrift für Physiologiche Chemie, Vol. 364, p. 593 (1983) or methods analogous thereto.

The compound (I) or a salt thereof thus produced can be recovered, after completion of the reaction, by means for separating peptide, for example, extraction, partition, reprecipitation, crystallization, various chromatographic processes, high performance liquid chromatography, etc.

The desirable examples of the compound of this invention include the compound of the formula (Ia)

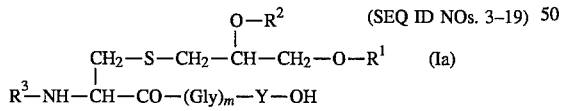

wherein $R^1$, $R^2$ and $R^3$ are the same meaning as defined above; m is an integer of 0 to 3; Y is an amino acid sequence consisting of 3 amino acid residues selected from the group consisting of glutamyl and glycyl, when m is 0; Y is L-glutamyl or glutamyl-glutamyl, when m is 1; Y is L-glutamyl, when m is 2; Y is an amino acid sequence consisting of 1 to 3 amino acid residues selected from the group consisting of an acidic amino acid residue and threonyl, the N-terminal of Y is an acidic amino acid residues, when m is 3; or a salt thereof.

In the formula (Ia), when m is 0, Y is desirably glutamyl-glycyl-glutamyl or glutamyl-glutamyl-glutamyl, more desirably Y is glutamyl-glycyl-glutamyl.

In the formula (Ia), when m is 3, Y is desirably an amino acid sequence consisting of 1 to 3 amino acid residues selected from the group consisting of glutamyl, aspartyl and threonyl, the N-terminal of Y is glutamyl or aspartyl, more desirably Y is an amino acid sequence consisting of 1 to 3 amino acid residues selected from the group consisting of glutamyl and threonyl, the N-terminal of Y is glutamyl.

In the formula (Ia), the acidic amino acid residue is the same meaning as defined above.

A salt of the compound (I) of this invention with a base, especially with a pharmaceutically acceptable base, can be obtained, by a per se known method, Examples of the base include an alkali metal such as sodium, potassium, etc., an alkaline earth metal such as calcium, magnesium, etc., an organic base such as triethylamine, pyridine, etc. and so on.

A salt of the compound (I) with an acid, especially a pharmaceutically acceptable acid can be obtained by a per Se known method. Examples of the acid include an acid addition salt, especially a pharmaceutically acceptable acid addition salt, for example, a salt with an inorganic acid (e.g. hydrochloric acid, sulfuric acid, phosphoric acid, etc.) or with an organic acid (e.g. acetic acid, propionic acid, citric acid, tartaric acid, mac acid, oxalic acid, etc.).

And, as salts of the Compound (Ia) to (VII), use is made of those substantially the same as salts of the compound (I).

Protecting groups and reagents frequently used in the following description are abbreviated as follows.

Fmoc: 9-fluorenylmethyloxycarbonyl
Z: benzyloxycarbonyl
Boc: t-butoxycarbonyl
'Bu: t-butyl
O'Bu: t-butoxy
TFA: trifluoroacetic acid
TEA: triethylamine
DMF: N,N-dimethylformamide
DCC: N,N'-dicyclohexylcarbodiimide
DIC: N,N'-diisopropylcarbodiimide
HONB: N-hydroxy-5-norbornene-2,3-dicarboxyimide
HOBT: 1-hydroxybenzotriazole
DEPC: diethyl phosphorocyanidate
DCM: dichloromethane
THF: tetrahydrofuran Further, in the present specification, S-[2,3-bis(hexadecanoyloxy)-( 2S)-propyl]-(R)-cysteine is sometimes abbreviated as Dhc(Pam)$_2$. Furthermore, said compound is named as (2R,6S)-2-amino-6,7-bis(hexadecanoyloxy)- 4-thiaheptanoic acid, which is sometimes written simply as (2R,6S)-2-amino-6,7-bis(PamO)- 4-THT-OH.

The compound forming the basic skeleton of the compounds in the present specification is 2-amino-6,7-dihydroxy- 4-thiaheptanoic acid shown by the following formula:

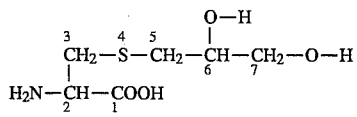

In the present specification, thiaheptanoyl is abbreviated as THT, and thiaheptanoic acid as THT-OH. And, n-hexadacanoyl, n-tetradecanoyl and n-hexadecanoyloxy are abbreviated as Pam, Myr and PamO, respectively.

Among the compounds obtained by the method described above, representative ones are shown as their structural formulae Table 2.

TABLE 2

| Compound No. | Example No. | Structural Formula |
|---|---|---|
| 1 | 8 | Pam—Dhc(Pam)$_2$—Gly—Gly—Gly—Glu—Thr—Thr—OH (SEQ. ID No: 89) |
| 2 | 9 | (2R,6S)-2-Myr-amino-6,7-bis(PamO)-4-THT—Gly—Gly—Gly—Glu—Thr—Thr—OH (SEQ. ID NO: 90) |
| 3 | 10 | (2R,6S)-2-isomyristoylamino-6,7-bis(PamO)-4-THT—Gly—Gly—Gly—Glu—Thr—Thr—OH (SEQ. ID NO: 91) |
| 4 | 11 | (2R,6S)-2-Myr-amino-6,7-bis(PamO)-4-THT—Gly—Gly—Gly—Glu—OH (SEQ. ID NO: 92) |
| 5 | 12 | (2R,6S)-2-Myr-amino-6,7-bis(PamO)-4-THT—Gly—Gly—Gly—D—Glu—OH |
| 6 | 13 | (2S,6R)-2-Myr-amino-6,7-bis(PamO)-4-THT—Gly—Gly—Gly—Glu—Thr—Thr—OH (SEQ. ID NO: 93) |
| 7 | 14 | (2S,6S)-2-Myr-amino-6,7-bis(PamO)-4-THT—Gly—Gly—Gly—Glu—Thr—Thr—OH (SEQ. ID NO: 94) |
| 8 | 15 | (2R,6R)-2-Pam-amino-6,7-bis(PamO)-4-THT—Gly—Gly—Gly—Glu—Thr—Thr—OH (SEQ. ID NO: 95) |
| 9 | 16 | (2R,6R)-2-Myr-amino-6,7-bis(PamO)-4-THT—Gly—Gly—Gly—Glu—Thr—Thr—OH (SEQ. ID NO: 96) |
| 10 | 17 | (2R,6R)-2-Myr-amino-6-hexanoyloxy-7-PamO-4-THT—Gly—Gly—Gly—Glu—OH (SEQ. ID NO: 97) |
| 11 | 18 | (2R,6R)-2-Myr-amino-6,7-bis(PamO)-4-THT—Gly—Gly—Gly—Glu—Thr—OH (SEQ. ID NO: 98) |
| 12 | 19 | (2R,6R)-2-Myr-amino-6,7-bis(PamO)-4-THT—Gly—Gly—Gly—Glu—OH (SEQ. ID NO: 99) |
| 13 | 20 | (2R,6R)-2-Myr-amino-6,7-bis(PamO)-4-THT—Gly—Gly—Gly—D—Glu—OH |
| 14 | 21 | (2R,6R)-2-Myr-amino-6,7-bis(PamO)-4-THT—Gly—Gly—Gly—Asp—OH (SEQ. ID NO: 100) |
| 15 | 22 | (2R,6R)-2-Myr-amino-6,7-bis(PamO)-4-THT—Gly—Gly—Gly—OH (SEQ. ID NO: 101) |
| 16 | 23 | (2R,6R)-2-Myr-amino-6,7-bis(PamO)-4-THT—Gly—Gly—Glu—OH (SEQ. ID NO: 102) |
| 17 | 24 | (2R,6R)-2-Myr-amino-6,7-bis(PamO)-4-THT—Gly—Gly—Gly—D—Glu—OH |
| 18 | 25 | (2R,6R)-2-Myr-amino-6,7-bis(PamO)-4-THT—Gly—Gly—OH |
| 19 | 26 | (2R,6R)-2-Myr-amino-6,7-bis(PamO)-4-THT—Gly—Glu—OH |
| 20 | 27 | (2R,6R)-2-Myr-amino-6,7-bis(PamO)-4-THT—Gly—D—Glu—OH |
| 21 | 28 | (2R,6R)-2-Myr-amino-6,7-bis(PamO)-4-THT—Glu—OH |
| 22 | 29 | (2R,6R)-2-Myr-amino-6,7-bis(PamO)-4-THT—D—Glu—OH |
| 23 | 30 | (2R,6R)-2-Myr-amino-6,7-bis(PamO)-4-THT—Asp—OH |
| 24 | 31 | (2R,6R)-2-Myr-amino-6,7-bis(PamO)-4-THT—D—Asp—OH |
| 25 | 32 | (2R,6R)-2-Myr-amino-6,7-bis(PamO)-4-THT—OH |
| 26 | 33 | (2R,6R)-2-Myr-amino-6,7-bis(PamO)-4-THT—Gly—Glu—Glu—OH (SEQ. ID NO: 103) |
| 27 | 34 | (2R,6R)-2-Myr-amino-6,7-bis(PamO)-4-THT—Gly—Glu—D—Glu—OH |
| 28 | 35 | (2R,6R)-2-Myr-amino-6,7-bis(PamO)-4-THT—Glu—Gly—Glu—OH (SEQ. ID NO: 104) |
| 29 | 36 | (2R,6R)-2-Myr-amino-6,7-bis(PamO)-4-THT—Glu—Gly—D—Glu—OH |
| 30 | 37 | (2R,6R)-2-Myr-amino-6,7-bis(PamO)-4-THT—Glu—Glu—OH |
| 31 | 38 | (2R,6R)-2-Myr-amino-6,7-bis(PamO)-4-THT—Glu—D—Glu—OH |
| 32 | 39 | (2R,6R)-2-Myr-amino-6,7-bis(PamO)-4-THT—Glu—Gly—Glu—Gly—D—Glu—OH |
| 33 | 40 | (2R,6R)-2-Myr-amino-6,7-bis(PamO)-4-THT—Glu—Glu—Glu—OH (SEQ. ID NO: 105) |
| 34 | 41 | (2R,6R)-2-Myr-amino-6,7-bis(PamO)-4-THT—Glu—Glu—D—Glu—OH |
| 29a | 42 | (2R,6R)-2-Myr-amino-6,7-bis(PamO)-4-THT—Glu(O$^t$Bu)—Gly—D—Glu(O$^t$Bu)—O$^t$Bu |
| 35 | 43 | (2R,6R)—N$^\delta$—(2-Pam-amino-6,7-bis(PamO)-4-THT)—Orn—Gly—Gly—Glu—OH (SEQ. ID NO: 106) hydrochloride |

Biological activities of compound (I) are described as follows.

EXPERIMENTAL EXAMPLE 1

Activities of the TAN-1511 complex and TAN-1511A obtained in Example 2, on enhancing proliferation of bone marrow cells of mice are shown in Table 3.

Table 3

Activities of TAN-1511 complex on enhancing proliferation of bone marrow cells of mice

| Test Compound | Concentration (ng/ml) | Degree of marrow cell proliferation |
|---|---|---|
| TAN-1511 complex | 10 | 3.05 |
| | 5 | 2.68 |
| | 2.5 | 2.45 |
| | 1.25 | 1.98 |
| | 0.625 | 1.71 |
| | 0.313 | 1.56 |
| TAN-1511A | 10 | 2.44 |
| | 5 | 2.04 |
| | 2.5 | 1.80 |
| | 1.25 | 1.69 |
| | 0.625 | 1.56 |
| | 0.313 | 1.38 |

[1] Proliferation in the group to which TAN-1511 is not added is shown as 1.

Method of determination:

To an RPMI 1640 culture medium [Bio-Wittaker Inc. (hereinafter abbreviated as BW), U.S.A] containing $2\times10^6$/ml of bone marrow cells of BALB/c mice, 2 mM of L-glutamine, 20 ug/ml of gentamicin (BW, USA), 10% fetal calf serum was added a test compound in an adequate concentration, which was incubated at 37° C. for 3 days in 5% carbon dioxide in air, followed by determination of proliferation of the bone marrow cells by the MTT reduction method [Tada et al., Journal of Immunological Methods, Vol.93, p.157, 1986].

EXPERIMENTAL EXAMPLE 2

Table 4 shows the action of TAN-1511 complex on enhancing the number of spleen cells and the number of peritoneal cavity cells of mice.

Table 4

Action of TAN-1511 complex on enhancing the number of spleen cells and the number of peritoneal cavity cells of mice

| Drug cavity | Number of spleen cells (%)[1] | Number of peritoneal cells (%)[1] |
|---|---|---|
| Cyclophosphamide singly | 11.8 | 27.7 |
| Cyclophosphamide + TAN-1511 complex | 42.6 | 83.3 |

[1] The number of cells when a physiological saline solution containing 2% gum arabic was injected to mice intraperitoneally is assumed as 100%.

Method of determination:

A BALB/c mouse was injected intraperitoneally with cyclophosphamide dissolved in physiological saline solution at a dose of 250 mg/kg. From the next day, the animal was administered intraperitoneally for 3 consecutive days with TAN-1511 complex suspended in physiological saline solution containing 2% gum arabic at a dose of 2 mg/kg/day. On the day following completion of the administration, number of trypan blue chromophobic cells of spleen and peritoneal cavity was counted.

EXPERIMENTAL EXAMPLE 3

Actions of the compounds (I) obtained in Examples 16, 19 and 26 on enhancing proliferation of bone marrow cells of mice are shown in Table 5.

Table 5

Action on enhancing proliferation of bone marrow cells in mice

| Test compounds | Minimum Effective Concentration (MEC, ng/ml)[1] |
|---|---|
| Compound 9 | 0.078 |
| Compound 12 | 0.313 |
| Compound 19 | 0.156 |

[1] Assuming that proliferation in the group to which no compound is added is assumed as 1, concentrations at which 1.3 or more times as much proliferation was observed were taken.

EXPERIMENTAL EXAMPLE 4

Table 6 shows the action of compound (I) on enhancing the number of spleen cells of mice.

TABLE 6

| Drug | Dosage (mg/kg/day) | Number of abdominal cavity cells (%)[1] |
|---|---|---|
| Cyclophosphamide singly | | 33.4 |
| Cyclophosphamide + compound 12 | 1.0 | 112 |

[1] Number of cells in the mouse administered intraperitoneally with physiological saline solution containing 2% gum arabic is assumed as 100%.

Method of Determination:

A BALB/c mouse was injected intraperitoneally with cyclophosphamide dissolved in physiological saline solution at a dose of 200 mg/kg. From the day after next, the animal was administered intraperitoneally for 4 consecutive days with the test compound suspended in physiological saline solution containing 2% gum arabic. On the day following completion of the administration, number of trypan blue chromophobic cells of spleen was counted.

EXPERIMENTAL EXAMPLE 5

Action of compound (I) on enhancing the number of leukocyte in mice is shown in Table 7.

Method of Determination:

Six week old female CDF1/Crj mice (5animals/group) were subjected to the experiment. Each animal was orally administered with cyclophosphamide dissolved in physiological saline solution at a dose of 150 mg/kg. From the next day, each animal was administered subcutaneously with the compound suspended in 5% glucose at the following dosages for five days once a day. On the next day after completion of the administration, about 100 μl of peripheral blood was collected from orbital vein using an EDTA-treated glass capillary. Then, the number of leukocytes was counted using a automatic cell analyzer (Sysmex K-2000, Toa Medical Electronics, Japan)

TABLE 7

| Action on enhancing the number of leukocytes | | |
|---|---|---|
| Test Compound | Dose(mg/kg/day) | Number of leukocytes (%)[1] |
| Compound 9 | 0.13 | 107 |
| Compound 16 | 0.13 | 98 |
| Compound 19 | 0.13 | 90 |

[1]The value is shown by percentage relative to the number of leukocytes (assumed as 100%) of the mouse orally administered with physiological saline solution, in place of cyclophosphamide, at a dose of 0.2 ml relative to 20 g of body weight, then subcutaneously administered, from the next day of the oral administration, with 5% glucose once a day for 5 days. Incidentally, the average value and standard deviation of leukocyte numbers of mice orally administered with cyclophosphamide at a dose of 150 mg/kg, then from the next day, subcutaneously administered with 0.2 ml of 5% glucose relative to 20 g of body weight once a day for 5 days were 41±11% throughout the experiment.

EXPERIMENTAL EXAMPLE 6

Toxicity test

No mouse administered intraperitoneally with Pam-Dhc-(Pam) $_2$-Gly-Gly-Gly-Glu-Thr-Thr-OH (Compound 1) (SEQ ID No. 89) at a dose of 400 mg/kg was found dead.

EXPERIMENTAL EXAMPLE 7

Acute toxicity test to mice

No mouse was killed by intraperitoneal administration of Compound 9 at a dose of 400 mg/kg.

Compound (I) or a salt thereof is low in toxicity and can be used safely.

As is clear from the foregoing Experimental Examples, Compound (I) or a salt thereof has an activity of remarkably improving hematopoiesis, which can be utilized as a therapeutic or prophylactic agent of leukocytopenia caused by radiotherapy or chemotherapy of cancers in mammals (e.g. dog, cat, cow, horse, monkey, man, etc.), as an hematopoietic-stimulating agent in the case of bone marrow transplantation, and, further, as an immunological enhancing agent having an action of increasing leukocytes.

In the case of administering Compound (I) or a salt thereof to, for example, man, it can be safely administered orally or non-orally alone or as a pharmaceutical composition by mixing with a suitable pharmaceutically acceptable carrier, excipient or diluent.

Examples of the above-mentioned pharmaceutical composition include injections, orally administrable compositions (e.g. powder, granules, capsules, tablets), topical compositions (e.g. transnasal agent, transdermal agent, etc.), and suppositories (e.g. rectal suppositories, vaginal suppositories).

These pharmaceutical compositions can be prepared by per se known methods generally employed in the processes of pharmaceutical preparation.

For example, the compound (I) or a salt thereof of this invention can be prepared into aqueous injections together with a dispersant (e.g. Tween 80 (manufactured by Atlas Powder Co., U.S.A.), HCO 60 (manufactured by Nikko Chemicals, Japan), polyethylene glycol, carboxymethyl cellulose, sodium alginate or the like), a preservative (e.g. methylparaben, propylparaben, benzyl alcohol, chlorobutanol or the like) and an isotonicating agent (e.g. sodium chloride, glycerin, sorbitol, glucose or the like), among others, or into oleagenous injections by dissolving, suspending or emulsifying in a vegetable oil such as olive oil, sesame oil, peanut oil, cotton seed oil, corn oil or the like, propylene glycol, among others.

For preparing the compound (I) or a salt thereof of this invention into compositions for oral administration, it is subjected to compression molding, in accordance with a per se known method, together with an excipient (e.g. lactose, sucrose, starch or the like), a disintegrator (e.g. starch, calcium carbonate or the like), a binding agent (e.g. starch, gum arabica, carboxymethyl cellulose, polyvinyl pyrrolidone, hydroxypropyl cellulose or the like) or a lubricant (e.g. talc, magnesium stearate, polyethylene glycol 6000), etc., followed by, upon necessity, masking the taste or coating by a per se known process for the purpose of enteric coating or of making the compositions to be of sustained-release. Examples of the coating agent include hydroxypropyl methyl cellulose, ethyl cellulose, hydroxymethyl cellulose, hdyroxypropyl cellulose, polyoxyethylene glycol, Tween 80, Brulonick F68, cellulose acetate phthalate, hdyroxypropyl methyl cellulose phthalate, hydroxymethyl cellulose acetate succinate, Eudragit (manufactured by Rohm, Germany, methacrylic acid.acrylic acid copolymer) and a pigment such as titanium oxide, red iron oxide, etc.

Subcoating layer may be provided between the enteric coating and the core according to per se known method.

For preparing the compound (I) or a salt thereof into, for example, solid, semi-solid or liquid compositions for topical use, a per se known method can be resorted to. For preparing solid compositions, for example, the compound (I) or a salt thereof is prepared into powdery compositions singly or in admixture with an excipient (e.g. glycol, mannitol, starch, microcrystalliine cellulose or the like), a thickening agent (e.g. natural rubbers, cellulose derivatives, acrylic acid polymers or the like). As the above-mentioned liquid composition, almost like in the case of injections, mention is made of oleaginous or aqueous suspensions. As the semi-solid composition, aqueous or oleagenous gel compositions or ointments are preferably counted. These compositions may be supplemented with a pH regulator (e.g. carbonic acid, phosphoric acid, citric acid, hydrochloric acid, sodium hydroxide, etc.), a preservative (e.g. para-hydroxybenzoic acid esters, chlorobutanol, benzalkonium chloride, etc.), among others.

In the case of preparing suppositories for example, the compound (I) or a salt thereof of the present invention can be prepared into oleagenous or water-soluble solid, semi-solid or liquid suppositories. As the oleagenous base for the above-mentioned compositions, any one which does not dissolve the compound (I) or a salt thereof can be employed, as exemplified by glyceride of higher fatty acid [e.g. cacao butter, Wittepsols (manufactured by Dynamite Nobel, Inc., Germany), etc.], middle class fatty acid [e.g. Migliols (manufactured by Dynamite Nobel, Inc.), etc.] or vegetable oil (e.g. sesame oil, soybean oil, cotton seed oil, etc.), among others. And, examples of the water-soluble base include polyethylene glycols and propylene glycols, and, examples of the water-soluble gel base include natural rubbers, cellulose derivatives, vinyl polymers, acrylic acid polymers, etc.

While the dosage of the compound (I) or a salt thereof when administered to man varies with diseases, administration routes, ages of the patients and states of diseases, it ranges usually from about 0.05 μg to 50 mg per day in terms of the active component, preferably from about 0.5 μg to 1 mg, more preferably about 2.5 μg to 0.25 mg, in the case of an adult patient of 50 kg body weight.

[Example]

The following examples describe the present invention in more detail, but are not intended to limit the invention. Incidentally, % in the culture medium means weight/volume, unless otherwise specified. The numerals showing the mixing ratio in mixed solvents mean the volume ratio of each solvent.

Reference Example 1

Production of $N^\alpha$-Boc-Orn-Gly-Gly-Glu(O$^t$Bu)-O$^t$Bu hydrochloride (SEQ ID No. 10)

a) $N^\delta$-Z-$N^\alpha$-Boc-ornithine (402 mg), H-Gly-Gly-Glu(O$^t$Bu)-O$^t$Bu hydrochloride 500 mg), DEPC (270 mg) and triethylamine (444 mg) were dissolved in DMF (6 ml) and then stirred at 20° C. for 4 hours. After the solvent was removed under reduced pressure, the residue was purified by means of a silica gel column chromatography (chloroform-:methanol=30:1) to give $N^\delta$-Z—$N^\alpha$-Boc-Orn-Gly-Gly-Glu-(O$^t$Bu)-O$^t$Bu (SEQ ID No. 10) (838 mg, 100%) as colorless wax.

$^1$H-NMR (CDCl$_3$) δ: 1.43 (18H,s), 1.46 (9H,s), 1.20–2.35 (8H,m), 3.10–3.40 (2H,m), 3.80–4.10 (4H,m), 4.18 (1H,m), 4.45 (1H,m), 5.09 (2H,s), 5.24 (1H,m), 5.40 (1H,d,J=7.4 Hz), 6.91 (1H,d,J=8.0 Hz), 7.10–7.25 (2H,m), 7.35 (5H,s).

b) $N^\delta$-Z—$N^\alpha$-Boc-Orn-Gly-Gly-Glu(O$^t$Bu)-O$^t$Bu (SEQ ID No. 10) (838 mg) obtained in a) was dissolved in methanol (10 ml). To this solution was added 10% (w/w, hereinafter in the same way) (Pd—C (525 mg) and the suspension was stirred at 20° C. for 15 hours in hydrogen stream. After removing the catalyst, the resulting solution was neutralized by adding a hydrogenchloride-methanol solution. The solvent was removed to give $N^\alpha$-Boc-Orn-Gly-Gly-Glu(O$^t$Bu)-O$^t$Bu hydrochloride (SEQ ID No. 10) (625 mg, 86%) as a white powder.

IR (KBr) ν: 3300, 2970, 1725, 1660, 1535, 1360, 1250, 1150 cm$^{-1}$ $^1$H-NMR (DMSO-d$_6$) δ: 1.40 (27H,s), 1.15–2.00 (6H,m), 2.26 (2H,t,J=7.6 Hz), 2.65–2.85 (2H,m), 3.50–4.00 (5H,m), 4.13 (1H,m), 7.00 (1H,d,J=7.8 Hz), 7.78 (3H,br s), 8.00–8.40 (3H,m)

Example 1

A seed culture medium (40 ml, pH 7.0) containing glucose 2%, soluble starch 3%, soybean meal 1%, corn steep liquor 0.3, peptone 0.5%, NaCl 0.3% and CaCO$_3$ 0.5% in an Erlenmeyer flask was inoculated with Streptosporangium sp. AL-23456 cultured on a yeast extract-malt extract agar slant, which was incubated on a rotary shaker at 28° C. for 48 hours. Five ml of this culture broth was transplanted into 500 ml of a seed culture medium placed in a Sakaguchi flask of 2000 ml capacity, and incubated on a reciprocating shaker at 28° C. for 48 hours. A seed culture medium (120 l, pH 7) in a stainless steel tank of 500 ml capacity was inoculated 500 ml of the culture broth obtained above, which was incubated for 2 days at 28° C. under aeration of 120 L/min., 150 r.p.m and inner pressure of 1 kg/cm$^2$ to give a seed culture broth. This seed culture broth (100 L) was transplanted on 3600 l of a main culture of raw soybean powder, 0.5% of yeast extract, 0.7% of CaCO$_3$ (pH unmodified) in stainless steel tank of 6000 L capacity, which was incubated for 6 days at 32° C. under aeration of 3600 L/min., while stirring of 140 rpm, and inner pressure of 1 kg/cm$^2$ to obtain a main culture broth.

Example 2

Production of TAN-1511A and B

The culture broth was subjected to filtration by using a filter aid (Radiolite 600, Showa Kagaku Kogyo Co., Ltd., Japan) to give a culture filtrate (3880 L). The filtrate was adjusted to pH 2.0, then subjected to extraction with ethyl acetate (1200 L). The ethyl acetate layer (900 L) was subjected to extraction with an aqueous solution of sodium hydrogencarbonate (300 L). The aqueous layer (330 L) was adjusted to pH 2.0 and subjected to extraction twice with ethyl acetate (160 L). The active component of the ethyl acetate layer (290 L) was extracted with a 2% (w/v) aqueous solution of sodium hydrogencarbonate (140 L), and then the aqueous layer (155 L) was concentrated.

The concentrate (100 L) was adjusted to pH 8.0, which was subjected to a chromatography on Diaion SP- 207 (40 L, Mitsubishi Kasei Corporation (Japan), followed by development with a 4% (w/v) aqueous solution of sodium hydrogencarbonate (40 L). Effluent and eluate were combined (145 L), whose pH was adjusted to 2.0, followed by extraction twice with ethyl acetate (72 L). The ethyl acetate layer (130 L) was washed with water and concentrated. The concentrate (3.5 L) was dried on anhydrous sodium sulfate, which was subjected to a silica gel (250 g, E. Merck AG, Germany) chromatography. The column was washed with ethyl acetate (1.5 L) and ethyl acetate-isopropyl alcohol (2:1, 1.5 L), followed by eluting the active substance with ethyl acetate-isopropyl alcohol-water (4:2:1, 1.5 L) and ethyl acetate-isopropyl alcohol-water (2:2:1, 1.5 L). Fractions of the eluate were combined and concentrated. To the concentrate was added 0.05N hydrochloric acid, which was subjected to extraction with ethyl acetate (250 ml×3). The extract solutions were combined (750 ml), washed with water and dried over anhydrous sodium sulfate, and concentrated to leave a crude powdery product (1.65 g). This crude powdery product was dissolved in methanol (50 ml), which was subjected to chromatography on Sephadex LH-20 (3.0 L, Pharmacia Labs. Inc. Sweden), developing with methanol. Fractions containing active component were combined and concentrated to give TAN-1511 complex as brown powdery product (383 mg).

This powdery product was subjected to a column of Toyopal HW-40F (200 ml, Tosoh Co., Ltd.), developing with ethyl acetate-isopropyl alcohol-water (10:5:2.5), and fractionated in 10 ml each. Fractions No. 19 through No. 27 were combined and concentrated. To the concentrate was added 0.02N Hydrochloric acid (10 ml), which was subjected to extraction three times with isobutyl alcohol (10 ml). The organic layers were combined, washed with water (15 ml) and concentrated to give a powdery product (60 mg) containing TAN-1511A. Likewise, fractions No. 28 through No. 35 were combined and processed to give a powdery product (45 mg) containing TAN-1511A and B. The powdery product (60 mg) containing the component A was suspended in a small volume of methanol. Insolubles were collected by filtration to obtain a powdery product (34 mg), which was subjected to preparative HPLC [column; YMC-Pack SH- 043, SIL (Yamamura Chemical Laboratories, Japan), mobile phase; chloroform-methanol-water (6:3:0.5); hereinafter simply called preparative HPLC I, flow rate; 2.5 ml/min.]. Fractions containing the component A were combined and concentrated. To the concentrate was added water (4 ml), whose pH was adjusted to 2.0, which was washed with ethyl acetate (4 ml), followed by extraction with isobutyl alcohol (20 ml). The organic layer was washed with water, which was then concentrated to give a white powdery product (16.7 mg). This powdery product was subjected, by four instalments, to preparative HPLC [column; YMC-Pack SH-643-15, $NH_2$, mobile phase; 85% (v/v) methanol-0.05M phosphate buffer (pH 5.2); hereinafter called preparative HPLC II; flow rate; 5 ml/min.]. Fractions containing solely the component A were combined and concentrated. To the concentrate was added water (10 ml), whose pH was adjusted to 2.0, which was subjected to extraction with isobutyl alcohol (30 ml). The organic layer was washed with water, which was then concentrated to afford TAN-1511A as a white powdery product (9.3 mg). From the powdery product (45 mg) containing A and B obtained previously as above, 10 mg portion was taken and subjected to chromatography on Toyopal HW-40S (40 ml), developing with isobutyl alcohol, fractionating in 4 ml each. Fractions from No. 11 through No. 37 were combined and concentrated. To the concentrate was added water (10 ml), whose pH was adjusted to 2, followed by extraction with isobutyl alcohol (20 ml). The organic layer was washed with water and then concentrated to afford a white powdery product (9.1 mg). This powdery product was subjected to preparative HPLC I (flow rate; 5 ml/min.). Fractions containing the component B were combined (24 ml) and concentrated. To the concentrate was added water (10 ml), whose pH was adjusted to 2, followed by extraction with isobutyl alcohol (15 ml). The organic layer was washed with water and concentrated to afford a white powdery product (2.1 mg, purity: about 70%). This powdery product and another powdery product (2.7 mg) of substantially the same purity were combined and subjected again to preparative HPLC (flow rate; 2.5 ml/min.) to collect fractions containing solely the component B, which were combined and concentrated. To the concentrate was added water (10 ml), whose pH was adjusted to 2, followed by extraction with isobutyl alcohol (15 ml). The organic layer was washed with water and concentrated to afford a white powdery product (4.3 mg). This powdery product was dissolved in a small volume of methanol, which was left standing in a refrigerator overnight. Resulting precipitates were collected to afford TAN-1511B as a while powdery product (3.0 mg).

Example 3

Production of TAN-1511 C

In substantially the same manner as in Example 1, a culture filtrate (3900 L) was obtained, which was processed in substantially the same manner as in Example 2 to give a TAN-1511 complex (405 mg). This complex was subjected to a column on Toyopal HW-40F (200 ml) in two instalments, developing with substantially the same solvent system as used for isolation of TAN-1511A and B in Example 2. The respective effluents were fractionated in 10 ml each. The respective fractions from No. 10 through No. 13 were combined and concentrated. To the concentrate was added 0.02N hydrochloric acid (10 ml), which was subjected to extraction with isobutyl alcohol (20 ml). The organic layer was washed with water, and then concentrated to give a yellow oily product (150 mg). This oily product was subjected to preparative HPLC I (flow rate; 2.5 ml/min.) in two instalments. Fractions containing the component C were combined and concentrated to afford a powdery product (29.8 mg). This powdery product was subjected to preparative HPLC II (flow rate; 2.5 ml/min.). Fractions containing solely the component C were combined and concentrated. To the concentrate was added water (20 ml), whose pH was adjusted to 2, followed by extraction with isobutyl alcohol (10 ml) twice. The organic layer were combined and washed with water, and then concentrated to afford TAN-1511C as a white powdery product (10.1 mg).

Example 4

Production of Z-Gly-Gly-Gly-Glu(O$^t$Bu)-Thr($^t$Bu)-Thr($^t$Bu)-O$^t$Bu (SEQ ID No. 81)

I) Z-Thr($^t$Bu)-O$^t$Bu

Z-Thr-OH (25.3 g, 0. 1 mol, Peptide Research Laboratories, Japan) was suspended in dichloromethane (250 ml), to which was added conc. sulfuric acid (1 ml). The mixture was cooled on a dry ice-acetone bath, to which was blown isobutene (the volume increased by 200 ml). The vessel was closed tightly, and the mixture was stirred for 2 days at 20° C. The vessel was opened, into which was blown $N_2$ at 20° C. to purge isobutene, followed by addition of water. The mixture was neutralized with a 10% (W/V) aqueous solution of sodium hydrogencarbonate, which was subjected to extraction twice with dichloromethane. The dichloromethane layer was dried over anhydrous sodium sulfate, then the solvent was distilled off. The residue was purified by means of a silica gel column chromatography (n-hexane:chloroform =1:2) to give an oily product. The yield was 26.6 g (72.7%). Rf: 0.21 (n-hexane:chloroform =1:2) FAB-MS (M+H$^+$)=366 (Theoretical value =366)

II) Z-Thr($^t$Bu)-Thr($^t$Bu)-O$^t$Bu (1) Z-Thr($^t$Bu)-OH.DCHA (12.0 g, 25 mmol, Kokusan Kagaku, Japan) was suspended in a mixture of ethyl acetate (200 ml) and water (200 ml). To the suspension was added, under ice-cooling, 1N sulfuric acid (27.5 ml), then the mixture was stirred. The ethyl acetate layer was separated, which was dried over anhydrous sodium sulfate, followed by distilling off the solvent. The residue was dissolved in acetonitrile (200 ml), to which were added, under ice-cooling, HONB (4.93 g, 27.5 mmol) and DCC (5.67 g, 27.5 mmol). The mixture was stirred for 2 hours, then insolubles were filtered off.

(2) Z-The($^t$Bu)-O$^t$Bu (11.0 g, 30 mmol) obtained in I) was dissolved in methanol (300 ml). To the solution was added 10% palladium-carbon, and the mixture was stirred for 2 hours in hydrogen streams at 20° C. under 1 atm. The catalyst was removed and the solvent was distilled off. To the residue was added acetonitrile (200 ml) to make a solution. To the solution was added, under ice-cooling, diisopropyl ethylamine (5.48 ml, 31.5 mmol). The mixture was stirred, to which was added the solution prepared in (1), and the mixture was stirred at 20° C. overnight. The solvent was distilled off. To the residue were added ethyl acetate and water, which was subjected to extraction with ethyl acetate. The ethyl acetate layer was washed with a 10% (W/V) aqueous solution of citric acid, water, a saturated aqueous solution of sodium hydrogencarbonate and water, which was then dried over anhydrous sodium sulfate, followed by distilling off the solvent. The residue was purified by means of a silica gel column chromatography (n-hexane:ethyl acetate =3:1) to afford an oily product. This product was crystallized by leaving standing at a cool place, then resulting crystals were washed with n-hexane. The yield was 12.7 g (97.2%). Rf: 0.74 (n-hexane:ethyl acetate =2:1), 0.13 (chloroform) m.p. 92.5°–93.5° C. $[\alpha]_D^{25}$+25.4° (c=1.02 in DMF)

Elemental Analysis for $C_{28}H_{46}N_2O_7$: Calcd.: C, 64.34; H, 8.87; N,5.36 Found: C, 64.26; H, 9.01; N, 5.33 FAB-MS (M+H$^+$)=523 (Theoretical value 523)

III) Z-Glu(O$^t$Bu)-Thr($^t$Bu)-Thr($^t$Bu)-$^{O^t}$Bu (1) Z-Glu(O$^t$Bu)-OH (6.17 g, 18.3 mmol, Peptide Research Laboratories, Japan) was dissolved in acetonitrile (200 ml). To the solution were added, under ice-cooling, HONB (3.60 g, 20.1 mmol) and DCC (4.15 g, 20.1 mmol). The mixture was stirred for 2 hours under ice-cooling, then insolubles were filtered off.

(2) Z-Thr(<sup>t</sup>Bu)-Thr(<sup>t</sup>Bu)-O<sup>t</sup>Bu obtained in II) (11.5 g, 22.0 mmol) was dissolved in methanol (300 ml). To the solution was added 10% palladium-carbon, and the mixture was stirred for 2 hours in hydrogen streams at 20° C. under 1 atm. The catalyst was filtered off, then the solvent was distilled off. To the residue was added acetonitrile (200 ml) to make a solution. To the solution was added, under ice-cooling, diisopropyl ethylamine (3.83 ml, 22.0 mmol), and the mixture was stirred, to which was added the solution prepared in (1) above, followed by stirring overnight. The solvent was distilled off. To the residue was added ethyl acetate and water. The mixture was subjected to extraction with ethyl acetate. The ethyl acetate layer was washed with a 10% (W/V) aqueous solution of citric acid, water, a saturated aqueous solution of sodium hydrogencarbonate and water, which was dried over anhydrous sodium sulfate, then the solvent was distilled off. The residue was purified by means of a silica gel column chromatography (n-hexane:ethyl acetate =3:1) to give an oily product. This product was left standing in a cool place, then resulting crystals were washed with n-hexane. The yield was 10.38 g (97.8%). Rf: 0.29 (n-hexane:ethyl acetate =3:1), 0.78 [5%(V/V) methanol-chloroform] m.p. 118.0°–119.5° C. $[\alpha]_D^{25}$+10.4° (c=1.00, in DMF)

Elemental Analysis for $C_{37}H_{61}N_3O_{10}$: Calcd.: C, 62.78; H, 8.69; N,5.94 Found: C, 62.88; H, 8.89; N,5.68 Amino acid analysis [6N HCl, 110° C., 24 hours hydrolysis; values in parentheses show theoretical ones]: Glu 1.00(1); Thr 1.81(2) FAB-MS (M+H<sup>+</sup>)=708 (theoretical value =708)

IV) Z-Gly-Gly-Gly-Glu(O<sup>t</sup>Bu)-Thr(<sup>t</sup>Bu)-Thr(<sup>t</sup>Bu)-O<sup>t</sup>Bu (SEQ ID No. 81)

(1) H-Gly-Gly-Gly-OH (10.0 g, 52.9 mmol, Peptide Research Laboratories, Japan) was dissolved in a 4N aqueous solution of sodium hydroxide (13.3 ml). To the solution were added, under ice-cooling, 4N aqueous solution of sodium hydroxide (15.9 ml) and benzyloxycarbonyl chloride (9.31 ml). The mixture was stirred overnight at 20° C. The reaction mixture was washed with ether. To the aqueous layer was added, under ice-cooling, 5N HCl to adjust to pH 3, which was left standing overnight in a cool place. Resulting crystals were collected by filtration, washed with cold water, then dried. The crystals thus obtained were used without purification. Yield 13.4 g (78.5%)

(2) Z-Gly-Gly-Gly-OH (3.04 g, 9.41 mmol) obtained in (1) was dissolved in DMF (200 ml). To the solution were added, under ice-cooling, HONB (1.86 g, 10.4 mmol) and DCC (2.14 g, 10.4 mmol). The mixture was stirred for 2 hours under ice-cooling. Insolubles were filtered off.

(3) Z-Glu(O<sup>t</sup>Bu)-Thr(<sup>t</sup>Bu)-Thr(<sup>t</sup>Bu)-O<sup>t</sup>Bu (6.66 g, 9.4 mmol) obtained in III) was dissolved in methanol (300 ml), to which was added 10% palladium-carbon. The mixture was stirred for 2 hours in hydrogen streams at 20° C. under 1 atm. The catalyst was removed, then the solvent was distilled off. To the residue was added DMF (150 ml) to make a solution. To the solution was added, under ice-cooling, diisopropyl ethylamine (1.80 ml, 10.4 mmol). The mixture was stirred, to which was added the solution prepared in (2), followed by stirring overnight at 20° C. The solvent was distilled off. To the residue were added chloroform and water. The mixture was subjected to extraction with chloroform. The chloroform layer was washed with a 10% (W/V) aqueous solution of citric acid, water, a saturated aqueous solution of sodium hydrogencarbonate, water, which was then dried over anhydrous sodium sulfate, followed by distilling off the solvent. The residue was purified by means of a silica gel column chromatography [5% (V/V) methanol-chloroform], which was recrystallized from ethyl acetate—acetonitrile to afford Z-Gly-Gly-Gly-Glu(O<sup>t</sup>Bu)-Thr(<sup>t</sup>Bu)-Thr(<sup>t</sup>Bu)-O<sup>t</sup>Bu (SEQ ID No. 81) as crystals. Yield 5.74 g (75.4) Rf: 0.20 [5% (V/V) methanol-chloroform] m.p. 167.5°–168.0° C. $[\alpha]_D^{25}$+7.28° (c=1.03, in DMF)

Elemental Analysis for $C_{43}H_{70}N_6O_{13}$: Calcd.: C, 58.75; H, 8.03; N, 9.56 Found: C, 58.52; H, 7.78; N, 9.35 Amino acid analysis [6N HCl, 110° C., 24 hours hydrolysis; Values in parentheses show theoretical ones.]: Glu 1.00(1); Thr 1.81(2); Gly 2.84(3) FAB-MS (M+H<sup>+</sup>)=879 (theoretical value =879)

Example 5

Production of Fmoc-Dhc(Pam)<sub>2</sub>-Gly-Gly-Gly-Glu(O<sup>t</sup>Bu)-Thr(<sup>t</sup>Bu)-Thr(<sup>t</sup>Bu)-O<sup>t</sup>Bu (SEQ ID No. 17)

(1) Z-Gly-Gly-Gly-Glu(O<sup>t</sup>Bu)-Thr(<sup>t</sup>Bu)-Thr(<sup>t</sup>Bu)-O<sup>t</sup>Bu (SEQ ID No. 12) (1.97 g, 2.24 mmol) obtained in Example 4-IV) was dissolved in methanol (60 ml). To the solution was added 10% palladium-carbon (120 mg), and the mixture was stirred for 2 hours in hydrogen streams at 20° C. under 1 atom. The catalyst was removed, then the solvent was distilled off to leave H-Gly-Gly-Gly-Glu(O <sup>t</sup>Bu)-Thr(<sup>t</sup>Bu)-Thr(<sup>t</sup>Bu)-O<sup>t</sup>Bu (SEQ ID No. 81) as a solid product.

(2) Fmoc-Dhc(Pam)<sub>2</sub>-OH (1.79 g) synthesized by the method of J. W. Metzger et al. described in Int. J. Peptide Protein Res., 38, pp. 545–554, 1991 was dissolved in DMF (20 ml). To the solution were added, under ice-cooling, HONB (394 mg), DIC (344 μl) and H-Gly-Gly-Gly-Glu-(O<sup>t</sup>Bu)-Thr(<sup>t</sup>Bu)-Thr(<sup>t</sup>Bu)-O<sup>t</sup>Bu (SEQ ID No. 61) (1.64 g) obtained in (1). The mixture was stirred for 24 hours at 20° C. The reaction mixture was concentrated, which was dissolved in chloroform. The solution was washed with a 10% (W/V) aqueous solution of citric acid, water, a saturated aqueous solution of sodium hydrogencarbonate and water, successively. The chloroform layer was dried over anhydrous sodium sulfate, which was then concentrated. To the concentrate was added acetonitrile, which was subjected to filtration to collect Fmoc-Dhc(Pam)<sub>2</sub>-Gly-Gly-Gly-Glu(O <sup>t</sup>Bu)-Thr(<sup>t</sup>Bu)-Thr(<sup>t</sup>Bu)-O<sup>t</sup>Bu (SEQ ID No. 17) as a white powdery product. The yield was 3.16 g (97%) $[\alpha]_D^{18}$+6.5° (c=0.54, in chloroform)

Elemental Analysis for $C_{88}H_{145}N_7O_{18}S$: Calcd.: C, 65.20; H, 9.02; N, 6.05; S, 1.98 Found: C, 64.90; H, 8.83; N, 5.86; S, 1.78 Amino acid analysis [6N HCl, 110° C., hydrolysis for 20 hours; Values in parentheses show theoretical ones.]: Glu 1.00(1); Thr 1.93(2); Gly 2.96(3) FAB-MS (M+Na)=1643 (theoretical value =1643)

Example 6

Production of H-Dhc(Pam)<sub>2</sub>-Gly-Gly-Gly-Glu(O<sup>t</sup>Bu)-Thr(<sup>t</sup>Bu)-Thr(<sup>t</sup>Bu)-O<sup>t</sup>Bu (Compound N-1) (SEQ ID No. 17)

Fmoc-Dhc(Pam)<sub>2</sub>-Gly-Gly-Gly-Glu(O<sup>t</sup>Bu)-Thr(<sup>t</sup>Bu)-Thr(<sup>t</sup>Bu)-O<sup>t</sup>Bu (SEQ ID No. 17) (2.70 g) obtained in Example 5 was dissolved in DMF (27 ml). To the solution was added piperidine (2.7 ml), and the mixture was stirred for one hour at 20° C. The reaction mixture was concentrated, which was subjected to a silica gel chromatography, eluting with chloroform-methanol (50:1, 20:1), successively. Fractions containing the object compound were combined and concentrated to give H-Dhc(Pam) <sub>2</sub>-Gly-Gly-Gly-Glu(O<sup>t</sup>Bu)-Thr(<sup>t</sup>Bu)-Thr(<sup>t</sup>Bu)-O<sup>t</sup>Bu (SEQ ID No. 17) (Compound N-1) as a white powdery product. The yield was 2.10 g (90%). $[\alpha]_D^{18}$+7.1° (c=0.49, in chloroform)

Elemental Analysis for $C_{73}H_{135}N_7O_{16}S$: Calcd.: C, 62.67; H, 9.73; N, 7.01; S, 2.29 Found: C, 62.55; H, 9.85; N, 6.95; S, 2.21 Amino acid analysis [6N HCl, 110° C., hydrolysis for 20 hours; Values in parentheses show theoretical ones.]: Glu 1.00(1); Thr 1.92(2); Gly 2.95(3) FAB-MS (M+H)=1399 (theoretical value =1399)

Example 7

Production of Pam-Dhc(Pam)$^2$-Gly-Gly-Gly-Glu(O$^t$Bu)-Thr($^t$Bu)-Thr($^t$Bu)-O$^t$Bu (SEQ ID No. 17)

In DMF (15 ml) was dissolved H-Dhc(Pam)$^2$-Gly-Gly-Gly-Glu(O$^t$Bu)-Thr($^t$Bu)-Thr($^t$Bu)-O$^t$Bu (Compound N-1) (SEQ ID No. 17) (1.50 g) obtained in Example 6. To the solution were added, under ice-cooling, a solution of hexadecanoyl chloride (353 mg) in DMF (10 ml) and N,N-diisopropyl ethylamine (223 μl). The reaction mixture was stirred for 7 hours at 20° C., which was concentrated. To the concentrate was added acetonitrile, then resulting powder was collected by filtration. The powder was dissolved in chloroform, which was washed with a 10% (W/V) aqueous solution of citric acid, then with water. The chloroform layer was dried over anhydrous sodium sulfate, which was concentrated. The concentrate was subjected to a silica gel chromatography, eluting with chloroform then with chloroform-methanol (30:1). Fractions containing the object compound were combined and concentrated. To the concentrate was added a mixture of ether and acetonitrile. Resulting powdery precipitates were collected by filtration to afford Pam-Dhc(Pam)$_2$-Gly-Gly-Gly-Glu(O$^t$Bu)-Thr($^t$Bu)-Thr($^t$Bu)-O$^t$Bu (SEQ ID No. 17) as a white powdery product. The yield was 1.22 g (70%). $[\alpha]_D^{18}$+3.8° (c=0.47, in chloroform)

Elemental Analysis for $C_{89}H_{165}N_7O_{17}S$: Calcd.: C, 65.29; H, 10.16; N, 5.99; S, 1.96 Found: C, 65.30; H, 10.27; N, 6.00; S, 2.02 Amino acid analysis [6N HCl, 110° C., hydrolysis for 20 hours; Values in parentheses show theoretical ones.]; Glu 1.00(1); Thr 1.92(2); Gly 2.93(3) FAB-MS (M+H)=1637 (theoretical value =1637)

Example 8

Production of Pam-Dhc(Pam)$_2$-Gly-Gly-Gly-Glu-Thr-Thr-OH (Compound 1)(SEQ ID No. 89)

In TFA (10 ml) was dissolved Pam-Dhc(Pam)$^2$-Gly-Gly-Gly-Glu(O$^t$Bu)-Thr($^t$Bu)-Thr($^t$Bu)-O$^t$Bu (SEQ ID No. 17) (1.17 g). The solution was left standing for 1.5 hour at 20° C. The reaction mixture was concentrated, to which was added a mixture of ether and acetonitrile. Resulting powdery precipitates were collected by filtration to afford Pam-Dhc(Pam)$_2$-Gly-Gly-Gly-Glu-Thr-Thr-OH (Compound 1) (SEQ ID No. 89) as a white powdery product. The yield was 966 mg (98%).

Elemental Analysis for $C_{73}H_{133}N_7O_{17}S\cdot1.5H_2O$: Calcd.: C, 60.89; H, 9.52; N, 6.81; S, 2.23 Found: C, 60.84; H, 9.42; N, 6.86; S, 2.45 Amino acid analysis [6N HCl, 110° C., hydrolysis for 20 hours; Values in parentheses show theoretical ones.]: Glu 1.00(1); Thr 1.92(2); Gly 2.93(3) FAB-MS (M+H) =1413 (theoretical value =1413)

Starting compounds employed in the following Examples are shown in Table 8. Methods for producing those compounds are described in Japanese Patent Application H5-181735, excepting Compound N-23. Incidentally, on the method for producing Compound N-23, Achiwa et al. reported in Peptide Chemistry, 361 (1991).

Table 8

(2R,6S)-2-amino-6,7-bis(PamO)-4-THT-Gly-Gly-Gly-Glu(O$^t$Bu)-Thr($^t$Bu)-Thr($^t$Bu)-O$^t$Bu (Compound N-1) (SEQ ID No. 17) (This compound is the same one as H-Dhc(Pam)$^2$-Gly-Gly-Gly-Glu(O$^t$Bu)-Thr($^t$Bu)-Thr($^t$Bu)-O$^t$Bu (SEQ ID No. 12) described in the above Example 6.)

(2R,6S)-2-amino-6,7-bis(PamO)-4-THT-Gly-Gly-Gly-Glu(O$^t$Bu)-O$^t$Bu (Compound N-2) (SEQ ID No. 15)

(2R,6S)-2-amino-6,7-bis(PamO)-4-THT-Gly-Gly-Gly-D-Glu(O$^t$Bu)-O$^t$Bu (Compound N-3) (SEQ ID No. 17)

(2S,6R)-2-amino-6,7-bis(PamO)-4-THT-Gly-Gly-Gly-Glu(O$^t$Bu)-Thr($^t$Bu)-Thr($^t$Bu)-O$^t$Bu (Compound N-4) (SEQ ID No. 17)

(2S,6R)-2-amino-6,7-bis(PamO)-4-THT-Gly-Gly-Gly-Glu(O$^t$Bu)-Thr($^t$Bu)-Thr($^t$Bu)-O$^t$Bu (Compound N-5) (SEQ ID No. 17)

(2R,6R)-2-amino-6,7-bis(PamO)-4-THT-Gly-Gly-Gly-Glu(O$^t$Bu)-Thr($^t$Bu)-Thr($^t$Bu)-O$^t$Bu (Compound N-6) (SEQ ID No. 17)

(2R,6R)-2-amino-6-hexanoyloxy-7-PamO-4-THT-Gly-Gly-Gly-Glu(O$^t$Bu)-O$^t$Bu (Compound N-7) (SEQ ID No. 15)

(2R,6R)-2-amino-6,7-bis(PamO)-4-THT-Glu(O$^t$Bu)-Gly-D-Glu(O$^t$Bu)-O$^t$Bu (Compound N-8)

(2R,6R)-2-amino-6,7-bis(PamO)-4-THT-Gly-Gly-Gly-Glu(O$^t$Bu)-Thr($^t$Bu)-O$^t$Bu (Compound N-9) (SEQ ID No. 16)

(2R,6R)-2-amino-6,7-bis(PamO)-4-THT-Gly-Gly-Gly-Glu(O$^t$Bu)-O$^t$Bu (Compound N-10) (SEQ ID No. 15)

(2R,6R)-2-amino-6,7-bis(PamO)-4-THT-Gly-Gly-Gly-D-Glu(O$^t$Bu)-O$^t$Bu (Compound N-11)

(2R,6R)-2-amino-6,7-bis(PamO)-4-THT-Gly-Gly-Gly-Asp(O$^t$Bu)-O$^t$Bu (Compound N-12) (SEQ ID No. 15)

(2R,6R)-2-amino-6,7-bis(PamO)-4-THT-Gly-Gly-Gly-O$^t$Bu (Compound N-13) (SEQ ID No. 10)

(2R,6R)-2-amino-6,7-bis(PamO)-4-THT-Gly-Gly-Gly-Glu(O$^t$Bu)-O$^t$Bu (Compound N-14) (SEQ ID No. 10)

(2R,6R)-2-amino-6,7-bis(PamO)-4-THT-Gly-Gly-D-Glu(O$^t$Bu)-O$^t$Bu (Compound N-15)

(2R,6R)-2-amino-6,7-bis(PamO)-4-THT-Gly-Gly-O$^t$Bu (Compound N-16)

(2R,6R)-2-amino-6,7-bis(PamO)-4-THT-Gly-Glu(O$^t$Bu)-O$^t$Bu (Compound N-17)

(2R,6R)-2-amino-6,7-bis(PamO)-4-THT-Gly-D-Glu(O$^t$Bu)-O$^t$Bu (Compound N-18)

(2R,6R)-2-amino-6,7-bis(PamO)-4-THT-Glu(O$^t$Bu)-O$^t$Bu (Compound N-19)

(2R,6R)-2-amino-6,7-bis(PamO)-4-THT-D-Glu(O$^t$Bu)-O$^t$Bu (Compound N-20)

(2R,6R)-2-amino-6,7-bis(PamO)-4-THT-Asp(O$^t$Bu)-O$^t$Bu (Compound N-21)

(2R,6R)-2-amino-6,7-bis(PamO)-4-THT-D-Asp(O$^t$Bu)-O$^t$Bu (Compound N-22)

(2R,6R)-2-amino-6,7-bis(PamO)-4-THT-O$^t$Bu (Compound N-23)

(2R,6R)-2-amino-6,7-bis(PamO)-4-THT-Gly-Glu(O$^t$Bu)-Glu(O$^t$Bu)-O$^t$Bu (Compound N-24) (SEQ ID No. 6)

(2R,6R)-2-amino-6,7-bis(PamO)-4-THT-Glu(O$^t$Bu)-D-Glu(O$^t$Bu)-O$^t$Bu (Compound N-25)

(2R,6R)-2-amino-6,7-bis(PamO)-4-THT-Glu(O$^t$Bu)-Gly-Glu(O$^t$Bu)-O$^t$Bu (Compound N-26) (SEQ ID No. 70)

(2R,6R)-2-amino-6,7-bis(PamO)-4-THT-Glu(O$^t$Bu)-Glu(O$^t$Bu)-O$^t$Bu (Compound N-27)

(2R,6R)-2-amino-6,7-bis(PamO)-4-THT-Glu(O$^t$Bu)-D-Glu(O$^t$Bu)-O$^t$Bu (Compound N-28)

(2R,6R)-2-amino-6,7-bis(PamO)-4-THT-Glu(O$^t$Bu)-Gly-Glu(O$^t$Bu)-Gly-D-Glu(O$^t$Bu)-O$^t$Bu (Compound N-29)

(2R,6R)-2-amino-6,7-bis(PamO)-4-THT-Glu(O$^t$Bu)-Glu(O$^t$Bu)-Glu(O$^t$Bu)-O$^t$Bu (Compound N-30) (SEQ ID No. 70)

(2R,6R)-2-amino-6,7-bis(PamO)-4-THT-Glu(O$^t$Bu)-Glu(O$^t$Bu)-D-Glu(O$^t$Bu)-O$^t$Bu (Compound N-31)

H-Glu(O$^t$Bu)-Gly-D-Glu(O$^t$Bu)-O$^t$Bu

Example 9

Production of (2R,6S)-Myr-amino-6,7-bis(PamO)-4-THT-Gly-Gly-Gly-Glu-Thr-Thr-OH (Compound 2) (SEQ ID No. 90)

Starting with (2R,6S)-2-amino-6,7-bis(PamO)-4-THT-Gly-Gly-Gly-Glu(O$^t$Bu)-Thr($^t$Bu)-Thr($^t$Bu)-O$^t$Bu N-1), (SEQ ID No. 17) Compound 2 was produced through (2R,6S)-2-Myr-amino-6,7-bis(PamO)-4-THT-Gly-Gly-Gly-Glu(O$^t$Bu)-Thr($^t$Bu)-Thr($^t$Bu)-O$^t$Bu (2a) (SEQ ID No. 17)

a) Compound N-1 (200 mg) and myristic acid (39 mg) were dissolved in DMF (2.0 ml). To the solution were added, under ice-cooling, HOBT (23 mg) and DIC (27 μl). The mixture was stirred for 40 hours at 20° C. The reaction mixture was concentrated, which was dissolved in chloroform (50 ml). This solution was washed with a 10% aqueous solution of citric acid, a saturated aqueous solution of sodium hydrogencarbonate and water, successively. The chloroform layer was dried over anhydrous sodium sulfate, which was then concentrated. The concentrate was subjected to a silica gel chromatography, developing with chloroform then with chloroform-methanol (50:1, 30:1). Fractions containing the object compound were collected and concentrated to give (2R,6S)-2-Myr-amino-6,7-bis(PamO)-4-THT-Gly-Gly-Gly-Glu(O$^t$Bu)-Thr($^t$Bu)-Thr($^t$Bu)-O$^t$Bu (2a) (SEQ ID. No. 17) as a white powdery product (205 mg, yield 89%). $[\alpha]_D^{23}$+3.6° (c=0.58, in chloroform)

Elemental analysis for $C_{87}H_{161}N_7O_{17}S$ Calcd.: C, 64.93; H, 10.08; N, 6.09; S, 1.99 Found: C, 64.75; H, 10.02; N, 6.38; S, 2.05 b) Compound 2a (155 mg) was dissolved in TFA (1.6 ml), which was left standing for 1.5 hour at 20° C. The reaction mixture was concentrated. The concentrate was suspended in acetonitrile, which was subjected to filtration to give (2R,6S)-2-Myr-amino-6,7-bis(PamO)-4-THT-Gly-Gly-Gly-Glu-Thr-Thr-OH (Compound 2) (SEQ ID No. 90) as a white powdery product (134 mg, yield 99%). $[\alpha]_D^{21}$−10.2° (c=0.55, in 5% TFA-chloroform)

Elemental Analysis for $C_{71}H_{129}N_7O_{17}S \cdot 1.5H_2O$ Calcd.: C, 60.40; H, 9.42; N, 6.94; S, 2.27 Found: C, 60.24; H, 9.17; N, 6.90; S, 2.23

Example 10

Production of (2R,6S)-2-isomyristoylamino-6,7-bis(PamO)-4-THT-Gly-Gly-Gly-Glu-Thr-Thr-OH (Compound 3) (SEQ ID No. 91)

In substantially the same manner as in Example 9, starting from (2R,6S)-2-amino-6,7-bis(PamO)-4-THT-Gly-Gly-Gly-Glu(O$^t$Bu)-Thr($^t$Bu)-Thr($^t$Bu)-O$^t$Bu (N-1) (SEQ ID No. 17) Compound 3 was produced via (2R,6S)-2-isomyristoylamino-6,7-bis(PamO)-4-THT-Gly-Gly-Gly-Glu(O$^t$Bu)-Thr($^t$Bu)-Thr($^t$Bu)-O$^t$Bu (3a) (SEQ ID No. 17).

| Starting compound (mg) | Reaction Conditions | | Product (mg) |
|---|---|---|---|
| a) N-1 (200) | isomyristic acid HOBT DIC DMF 20° C. silica gel chloroform, chloroform-methanol (50:1, 25:1) | 39 mg 23 mg 27 μl 2.0 ml 40 h | 3a (205) |
| b) 3a (150) | TFA 20° C. | 1.5 ml 1.5 h | 3 (126) |

Compound 3a: $[\alpha]_D^{23}$+3.4° (c=0.73, in chloroform)

Elemental Analysis for $C_{87}H_{161}N_7O_{17}S$: Calcd.: C, 64.93; H, 10.08; N, 6.09; S, 1.99 Found: C, 64.70; H, 9.95; N, 6.02; S, 1.72

Compound 3: $[\alpha]_D^{23}$−11.2° (c=0.54, in 5% TFA-chloroform)

Elemental Analysis for $C_{71}H_{129}N_7O_{17}S \cdot H_2O$: Calcd.: C, 60.79; H, 9.41; N, 7.00; S, 2.29 Found: C, 60.61; H, 9.35; N, 7.01; S, 2.20

Example 11

Production of (2R,6S)-2-Myr-amino-6,7-bis(PamO)-4-THT-Gly-Gly-Gly-Glu-OH (Compound 4) (SEQ ID No. 92).

In substantially the same manner as in Example 9, starting from (2R,6S)-2-amino-6,7-bis(PamO)-4-THT-Gly-Gly-Gly-Glu(O$^t$Bu)-O$^t$Bu (N-2) (SEQ ID No. 15) Compound 4 was produced via (2R,6S)-2-Myr-amino-6,7-bis(PamO)-4-THT-Gly-Gly-Gly-Glu(O$^t$Bu)-O$^t$Bu (4a) (SEQ ID No. 15).

| Starting compound (mg) | Reaction Conditions | | Product (mg) |
|---|---|---|---|
| a) N-2 (350) | myristic acid HOBT WSC DCM 20° C. | 74 mg 48 mg 68 mg 6.0 ml 20 h | 4a (372) |
| b) 4a (300) | TFA 20° C. | 3.0 ml 1.5 h | 4 (260) |

Compound 4a: $[\alpha]_D^{21}$−3.8° (c=0.60, in chloroform)

Elemental Analysis for $C_{71}H_{131}N_5O_{13}S \cdot 0.5H_2O$: Calcd.: C, 65.40; H, 10.20; N, 5.37; S, 2.46 Found: C, 65.27; H, 9.95; N, 5.41; S, 2.49

Compound 4: $[\alpha]_D^{21}$−4.7° (c=0.54, in 5% TFA-chloroform)

Elemental Analysis for $C_{63}H_{115}N_5O_{13}S \cdot 0.5H_2O$: Calcd.: C, 63.50; H, 9.81; N, 5.88; S, 2.69 Found: C, 63.53; H, 9.87; N, 5.88; S, 2.70

Example 12

Production of (2R,6S)-2-Myr-amino-6,7-bis(PamO)-4-THT-Gly-Gly-Gly-D-Glu-OH (Compound 5)

In substantially the same manner as in Example 9, starting from (2R,6S)-2-amino-6,7-bis(PamO)-4-THT-Gly-Gly-Gly-D-Glu(O$^t$Bu)-O$^t$Bu (N-3), Compound 5 was produced via (2R,6S)-2-Myr-amino-6,7-bis(PamO)-4-THT-Gly-Gly-Gly-D-Glu(O$^t$Bu)-O$^t$Bu (5a).

| Starting compound (mg) | Reaction Conditions | | Product (mg) |
|---|---|---|---|
| a) N-3 (350) | myristic acid HOBT WSC DCM 20° C. | 74 mg 48 mg 68 mg 6.0 ml 20 h | 5a (368) |
| b) 5a (300) | TFA 20° C. | 3.0 ml 1.5 h | 5 (263) |

Compound 5a: $[\alpha]_D^{21}$−3.9° (c=0.58, in chloroform)

Elemental Analysis for $C_{71}H_{131}N_5O_{13}S$: Calcd.: C, 65.86; H, 10.20; N, 5.41; S, 2.48 Found: C, 65.87; H, 9.98; N, 5.45; S, 2.50

Compound 5: $[\alpha]_D^{21}$−9.6° (c=0.53, in 5% TFA-chloroform)

Elemental Analysis for $C_{63}H_{115}N_5O_{13}S.0.5H_2O$: Calcd.: C, 63.50; H, 9.81; N, 5.88; S, 2.69 Found: C, 63.53; H, 9.57; N. 5.92; S, 2.67

Example 13

Production of (2S,6R)-2-Myr-amino-6,7-bis(PamO)-4-THT-Gly-Gly-Gly-Glu-Thr-Thr-OH (Compound 6) (SEQ ID No. 93)

In substantially the same manner as in Example 9, starting from (2S,6R)-2-amino-6,7-bis(PamO)-4-THT-Gly-Gly-Gly-Glu(O $^t$Bu)-Thr($^t$Bu)-Thr($^t$Bu)-O$^t$Bu (N-4) (SEQ ID No. 17), Compound 6 was produced via (2S,6R)-2-Myr-amino-6,7-bis(PamO)-4-THT-Gly-Gly-Gly-Glu(O $^t$Bu)-Thr($^t$Bu)-Thr($^t$Bu)-O$^t$Bu (6a) (SEQ ID No. 17)

| Starting compound (mg) | Reaction Conditions | | Product (mg) |
|---|---|---|---|
| a) N-4 (200) | myristic acid HOBT DIC DMF 20° C. silica gel chloroform-methanol (60:1, 30:1) | 39 mg 23 mg 27 μl 2.0 ml 40 h | 6a (205) |
| b) 6a (160) | TFA 20° C. | 1.6 ml 1.5 h | 6 (134) |

Compound 6a: $[\alpha]_D^{20}$+12.4° (c=0.53, in chloroform)
Elemental Analysis for $C_{87}H_{161}N_7O_{17}S$: Calcd.: C, 64.93; H, 10.08; N, 6.09; S, 1.99 Found: C, 64.73; H, 9.81; N, 6.18; S, 2.00

Compound 6: $[\alpha]_D^{21}$+3.0° (c=0.56, in 5% TFA-chloroform)
Elemental Analysis for $C_{71}H_{129}N_7O_{17}S.H_2O$: Calcd.: C, 60.79; H, 9.41; N, 6.99; S, 2.29 Found: C, 60.72; H, 9.32; N, 6.91; S, 2.32

Example 14

Production of (2S,6S)-2-Myr-amino-6,7-bis(PamO)-4-THT-Gly-Gly-Gly-Glu-Thr-Thr-OH (Compound 7) (SEQ ID No. 94)

In substantially the same manner as in Example 9, starting from (2S,6S)-2-amino-6,7-bis(PamO)-4-THT-Gly-Gly-Gly-Glu(O $^t$Bu)-Thr($^t$Bu)-Thr($^t$Bu)-O$^t$Bu (N-5) (SEQ ID No. 17), Compound 7 was produced via (2S,6S)-2-Myr-amino-6,7-(PamO)-4-THT-Gly-Gly-Gly-Glu(O $^t$Bu)-Thr($^t$Bu)-Thr($^t$Bu)-O$^t$Bu (7a) (SEQ ID No. 17).

| Starting compound (mg) | Reaction Conditions | | Product (mg) |
|---|---|---|---|
| a) N-5 (200) | myristic acid HOBT DIC DMF 20° C. silica gel Chloroform-methanol (60:1, 30:1) | 39 mg 23 mg 27 μl 2.0 ml 40 h | 7a (211) |
| b) 7a (160) | TFA 20° C. | 1.6 ml 1.5 h | 7 (131) |

Compound 7a: $[\alpha]_D^{20}$+13.8° (c=0.72, in chloroform)
Elemental Analysis for $C_{87}H_{161}N_7O_{17}S$: Calcd.: C, 64.93; H, 10.08; N, 6.09; S, 1.99 Found: C, 65.13; H, 9.91; N, 6.17; S, 2.01

Compound 7: $[\alpha]_D^{21}$+7.7° (c=0.52, in 5% TFA-chloroform)
Elemental Analysis for $C_{71}H_{129}N_7O_{17}S.H_2O$: Calcd.: C, 60.79; H, 9.41; N, 6.99; S, 2.29 Found: C, 60.80; H, 9.40; N, 6.87; S, 2.18

Example 15

Production of (2R,6R)-2-Pam-amino-6,7-bis(PamO)-4-THT-Gly-Gly-Gly-Glu-Thr-Thr-OH (Compound 8) (SEQ ID No. 95)

In substantially the same manner as in Example 9, starting from (2R,6R)-2-amino-6,7-bis(PamO)-4-THT-Gly-Gly-Gly-Glu(O $^t$Bu)-Thr($^t$Bu)-Thr($^t$Bu)-O$^t$Bu (N-6) (SEQ ID No. 17), Compound 8 was produced via (2R,6R)-2-Pam-amino-6,7-bis(PamO)-4-THT-Gly-Gly-Gly-Glu(O $^t$Bu)-Thr($^t$Bu)-Thr($^t$Bu)-O$^t$Bu (8a) (SEQ ID No. 17).

| Starting compound (mg) | Reaction Conditions | | Product (mg) |
|---|---|---|---|
| a) N-6 (180) | palmitic acid HOBT DIC DMF 20° C. silica gel chloroform-methanol (60:1, 30:1) | 40 mg 21 mg 24 μl 2.0 ml 40 h | 8a (189) |
| b) 8a (140) | TFA 20° C. | 1.4 ml 1.5 h | 8 (119) |

Compound 8a: $[\alpha]_D^{22}$–4.7° (c=0.57, in chloroform)
Elemental Analysis f or $C_{89}H_{165}N_7O_{17}S$: Calcd.: C, 65.29; H, 10.16; N, 5.99; S, 1.96 Found: C, 64.96; H, 10.07; N, 5.85; S, 1.82

Compound 8: $[E]_D^{22}$–16.0° (c=0.58, in 5% TFA-chloroform)
Elemental Analysis for $C_{73}H_{133}N_7O_{17}S.H_2O$: Calcd.: C, 61.27; H, 9.51; N, 6.85; S, 2.24 Found: C, 61.29; H, 9.15; N, 6.84; S, 2.08

Example 16

Production of (2R,6R)-2-Myr-amino-6,7-bis(PamO)-4-THT-Gly-Gly-Gly-Glu-Thr-Thr-OH (Compound 9) (SEQ ID No. 17)

In substantially the same manner as in Example 9, starting from (2R,6R)-2-amino-6,7-bis(PamO)-4-THT-Gly-Gly-Gly-Glu(O $^t$Bu)-Thr($^t$Bu)-Thr($^t$Bu)-O$^t$Bu (N-6), (SEQ ID No. 17) Compound 9 was produced via (2R,6R)-2-Myr-amino-6,7-bis(PamO)-4-THT-Gly-Gly-Gly-Glu(O $^t$Bu)-Thr($^t$Bu)-Thr($^t$Bu)-O$^t$Bu (9a).

| Starting compound (mg) | Reaction Conditions | | Product (mg) |
|---|---|---|---|
| a) N-6 (180) | myristic acid HOBT DIC DMF 20° C. silica gel chloroform, chloroform-methanol (50:1) | 36 mg 21 mg 24 μl 2.0 ml 40 h | 9a (193) |
| b) 9a (138) | TFA 20° C. | 1.4 ml 1.5 h | 9 (114) |

Compound 9a: $[\alpha]_D^{20}$ −5.4° (c=0.55, in chloroform)

Elemental Analysis for $C_{87}H_{161}N_7O_{17}S$: Calcd.: C, 64.93; H, 10.08; N, 6.09; S, 1.99 Found: C, 64.99; H, 9.64; N, 6.02; S, 1.89

Compound 9: $[\alpha]_D^{21}$ −13.7° (c=0.52, in 5% TFA-chloroform)

Elemental Analysis for $C_{71}H_{129}N_7O_{17}S \cdot 1.5H_2O$: Calcd.: C, 60.40; H, 9.42; N, 6.94; S, 2.27 Found: C, 60.20; H, 9.38; N, 6.89; S, 2.24

Example 17

Production of (2R,6R)-2-Myr-amino-6-hexanoyloxy-7-PamO-4-THT-Gly-Gly-Gly-Glu-OH (Compound 10) (SEQ ID No. 97)

In substantially the same manner as in Example 9, starting from (2R,6R)-2-amino-6-hexanoyloxy-7-PamO-4-THT-Gly-Gly-Gly-Glu(O $^t$Bu)-O$^t$Bu (N-7), (SEQ ID No. 15) Compound 10 was produced via (2R,6R)-2-Myr-amino-6-hexanoyloxy-7-PamO-4-THT-Gly-Gly-Gly-Glu(O$^t$Bu)-O$^t$Bu (10a) (SEQ ID No. 15).

| Starting compound (mg) | Reaction Conditions | | Product (mg) |
|---|---|---|---|
| a) N-7 (550) | myristic acid HOBT WSC DCM 20° C. | 146 mg 87 mg 123 mg 10.0 ml 15 h | 10a (606) |
| b) 10a (500) | TFA 20° C. | 5.0 ml 2.0 h | 10 (444) |

Compound 10a: $[\alpha]_D^{22}$ −8.0° (c=0.50, in chloroform)

Elemental Analysis for $C_{61}H_{111}N_5O_{13}S$: Calcd.: C, 63.46; H, 9.69; N, 6.07; S, 2.78 Found: C, 63.30; H, 9.68; N, 6.03; S, 2.74

Compound 10: $[\alpha]_D^{22}$ −11.1° (c=0.54, in 5% TFA-chloroform)

Elemental Analysis for $C_{53}H_{95}N_5O_{13}S \cdot 0.5H_2O$: Calcd.: C, 60.54; H, 9.20; N, 6.66; S, 3.05 Found: C, 60.36; H, 9.13; N, 6.78; S, 2.83

Example 18

Production of (2R,6R)-2-Myr-amino-6,7-bis(PamO)-4-THT-Gly-Gly-Gly-Glu-Thr-OH (Compound 11) (SEQ ID No. 98)

In substantially the same manner as in Example 9, starting from (2R,6R)-2-amino-6,7-bis(PamO)-4-THT-Gly-Gly-Gly-Glu(O $^t$Bu)-Thr($^t$Bu)-O$^t$Bu (N-9) (SEQ ID No. 16), Compound 11 was produced via (2R,6R)-2-Myr-amino-6,7-bis(PamO)-4-THT-Gly-Gly-Gly-Glu(O $^t$Bu)-Thr($^t$Bu)-O$^t$Bu (11a) (SEQ ID No. 16)

| Starting compound (mg) | Reaction Conditions | | Product (mg) |
|---|---|---|---|
| a) N-9 (441) | myristic acid HOBT WSC DCM 20° C. | 81 mg 53 mg 75 mg 7.4 ml 19 h | 11a (480) |
| b) 11a (422) | TFA 20° C. | 2.0 ml 2.0 h | 11 (378) |

Compound 11a: $[\alpha]_D^{23}$ −9.3° (c=0.46, in chloroform)

Elemental Analysis for $C_{79}H_{146}N_6O_{15}S$: Calcd.: C, 65.34; H, 10.13; N, 5.79; S, 2.21 Found: C, 65.25; H, 10.36; N, 6.04; S, 2.14

Compound 11: $[\alpha]_D^{23}$ −11.7° (c=0.55, in 5% TFA-chloroform)

Elemental Analysis for $C_{67}H_{122}N_6O_{15}S \cdot 2.5H_2O$: Calcd.: C, 60.56; H, 9.63; N, 6.32; S, 2.41 Found: C, 60.52; H, 9.28; N, 6.43; S, 2.38

Example 19

Production of (2R,6R)-2-Myr-amino-6,7-bis(PamO)-4-THT-Gly-Gly-Gly-Glu-OH (Compound 12) (SEQ ID No. 99)

In substantially the same manner as in Example 9, starting from (2R,6R)-2-amino-6,7-bis(PamO)-4-THT-Gly-Gly-Gly-Glu(O $^t$Bu)-O$^t$Bu (N-10) as starting material (SEQ ID No. 15), Compound 12 was produced via (2R,6R)-2-Myr-amino-6,7-bis(PamO)-4-THT-Gly-Gly-Gly-Glu(O$^t$Bu)-O$^t$Bu (12a) (SEQ ID No. 15).

| Starting compound (mg) | Reaction Conditions | | Product (mg) |
|---|---|---|---|
| a) N-10 (407) | myristic acid HOBT WSC DCM 20° C. | 86 mg 56 mg 79 mg 6.8 ml 21 h | 12a (417) |
| b) 12a (362) | TFA 20° C. | 2.0 ml 2.0 h | 12 (336) |

Compound 12a: $[\alpha]_D^{23}$ −8.6° (c=0.49, in chloroform)

Elemental Analysis for $C_{71}H_{131}N_5O_{13}S$: Calcd.: C, 65.86; H, 10.20; N, 5.41; S, 2.48 Found: C, 65.70; H, 10.11; N, 5.54; S, 2.45

Compound 12: $[\alpha]_D^{23}$ −8.9° (c=0.56, in 5% TFA-chloroform)

Elemental Analysis for $C_{63}H_{115}N_5O_{13}S \cdot 1.5H_2O$ Calcd.: C, 62.55; H, 9.83; N, 5.79; S, 2.65 Found: C, 62.74; H, 9.68; N, 5.91; S, 2.56

Example 20

Production of (2R,6R)-2-Myr-amino-6,7-bis(PamO)-4-THT-Gly-Gly-Gly-D-Glu-OH (Compound 13)

In the same manner as in Example 9, starting from (2R,6R)-2-amino-6,7-bis(PamO)-4-THT-Gly-Gly-Gly-D-Glu(O $^t$Bu)-O$^t$Bu (N-11), Compound 13 was produced via (2R,6R)-2-Myr-amino-6,7-bis(PamO)-4-THT-Gly-Gly-Gly-D-Glu(O $^t$Bu)-O$^t$Bu (13a).

| Starting compound (mg) | Reaction Conditions | | Product (mg) |
|---|---|---|---|
| a) N-11 (525) | myristic acid HOBT WSC DCM 20° C. | 111 mg 72 mg 102 mg 9.0 ml 19 h | 13a (575) |
| b) 13a (480) | TFA 20° C. | 2.0 ml 2.0 h | 13 (434) |

Compound 13a: $[\alpha]_D^{23}$ −7.6° (c=0.56, in chloroform)

Elemental Analysis for $C_{71}H_{131}N_5O_{13}S$: Calcd.: C, 65.86; H, 10.20; N, 5.41; S, 2.48 Found: C, 65.79; H, 10.02; N, 5.49; S, 2.53

Compound 13: $[\alpha]_D^{23}$ –15.9° (c=0.52, in 5% TFA-chloroform)

Elemental Analysis for $C_{63}H_{115}N_5O_{13}S\cdot1.5H_2O$ Calcd.: C, 62.55; H, 9.83; N, 5.79; S, 2.65 Found: C, 62.66; H, 9.68; N, 6.00; S, 2.67

Example 21

Production of (2R,6R)-2-Myr-amino-6,7-bis(PamO)-4-THT-Gly-Gly-Gly-Asp-OH (Compound 14) (SEQ ID No. 100)

In substantially the same manner as in Example 9, starting from (2R,6R)-2-amino-6,7-bis(PamO)-4-THT-Gly-Gly-Gly-Asp(O $^t$Bu)-O$^t$Bu (N-12) (SEQ ID No. 15), Compound 14 was produced via (2R,6R)-2-Myr-amino-6,7-bis(PamO)-4-THT-Gly-Gly-Gly-Asp(O $^t$Bu)-O$^t$Bu (14a) (SEQ ID No. 15).

| Starting compound (mg) | Reaction Conditions | | Product (mg) |
| --- | --- | --- | --- |
| a) N-12 (800) | myristic acid HOBT WSC DCM 20° C. | 187 mg 111 mg 158 mg 10.0 ml 21 h | 14a (856) |
| b) 14a (727) | TFA 20° C. | 8.0 ml 2.0 h | 14 (679) |

Compound 14a: $[\alpha]_D^{22}$ +1.0° (c=0.50, in chloroform)

Elemental Analysis for $C_{70}H_{129}N_5O_{13}S$: Calcd.: C, 65.64; H, 10.15; N, 5.47; S, 2.50 Found: C, 65.56; H, 10.25; N, 5.57; S, 2.26

Compound 14: $[\alpha]_D^{25}$ 0° (c=0.55, in 5% TFA-chloroform)

Elemental Analysis for $C_{62}H_{113}N_5O_{13}S\cdot1.5H_2O$: Calcd.: C, 62.28; H, 9.78; N, 5.86; S, 2.68 Found: C, 62.46; H, 9.77; N, 5.98; S, 2.62

Example 22

Production of (2R,6R)-2-Myr-amino-6,7-bis(PamO)-4-THT-Gly-Gly-Gly-OH (Compound 15) (SEQ ID No. 101)

In substantially the same manner as in Example 9, starting from (2R,6R)-2-amino-6,7-bis(PamO)-4-THT-Gly-Gly-Gly-O $^t$Bu (N-13) (SEQ ID No. 10), Compound 15 was produced via (2R,6R)-2-Myr-amino-6,7-bis(PamO)-4-THT-Gly-Gly-Gly-O $^t$Bu (15a) (SEQ ID No. 10).

| Starting compound (mg) | Reaction Conditions | | Product (mg) |
| --- | --- | --- | --- |
| a) N-13 (550) | myristic acid HOBT WSC DCM 20° C. | 153 mg 91 mg 129 mg 10.0 ml 24 h | 15a (605) |
| b) 15a (550) | TEA 20° C. | 5.0 ml 1.5 h | 15 (516) |

Compound 15a: $[\alpha]_D^{23}$ –14.3° (c=0.55, in chloroform)

Elemental Analysis for $C_{62}H_{116}N_4O_{10}S$: Calcd.: C, 67.11; H, 10.54; N, 5.05; S, 2.89 Found: C, 67.02; H, 10.45; N, 5.03; S, 2.90

Compound 15: $[\alpha]_D^{21}$ –14.8° (c=0.55, in 5% TFA-chloroform)

Elemental Analysis for $C_{58}H_{108}N_4O_{10}S\cdot0.5H_2O$: Calcd.: C, 65.56; H, 10.34; N, 5.27; S, 3.02 Found: C, 65.57; H, 10.17; N, 5.15; S, 2.90

Example 23

Production of (2R,6R)-2-Myr-amino-6,7-bis(PamO)-4-THT-Gly-Gly-Glu-OH (Compound 16) (SEQ ID No. 102)

In substantially the same manner as in Example 9, starting from (2R,6R)-2-amino-6,7-bis(PamO)-4-THT-Gly-Gly-Glu(O $^t$Bu)-O$^t$Bu (N-14) (SEQ ID No. 10), Compound 16 was produced via (2R,6R)-2-Myr-amino-6,7-bis(PamO)-4-THT-Gly-Gly-Glu(O $^t$Bu)-O$^t$Bu (16a) (SEQ ID No. 10).

| Starting compound (mg) | Reaction Conditions | | Product (mg) |
| --- | --- | --- | --- |
| a) N-14 (600) | myristic acid HOBT WSC DCM 20° C. | 134 mg 87 mg 123 mg 10.0 ml 24 h | 16a (646) |
| b) 16a (550) | TFA 20° C. | 5.0 ml 1.5 h | 16 (489) |

Compound 16a: $[\alpha]_D^{23}$ –8.8° (c=0.53, in chloroform)

Elemental Analysis for $C_{69}H_{128}N_4O_{12}S$: Calcd.: C, 66.95; H, 10.42; N, 4.53; S, 2.59 Found: C, 66.71; H, 10.43; N, 4.48; S, 2.45

Compound 16: $[\alpha]_D^{21}$ –11.5° (c=0.69, in 5% TFA-chloroform)

Elemental Analysis for $C_{61}H_{112}N_4O_{12}S\cdot0.5H_2O$: Calcd.: C, 64.57; H, 10.04; N, 4.94; S, 2.83 Found: C, 64.74; H, 9.97; N, 4.83; S, 2.76

Example 24

Production of (2R,6R)-2-Myr-amino-6,7-bis(PamO)-4-THT-Gly-Gly-D-Glu-OH (Compound 17)

In substantially the same manner as in Example 9, starting from (2R,6R)-2-amino-6,7-bis(PamO)-4-THT-Gly-Gly-D-Glu(O $^t$Bu)-O$^t$Bu (N-15), Compound 17 was produced via (2R,6R)-2-Myr-amino-6,7-bis(PamO)-4-THT-Gly-Gly-D-Glu(O $^t$Bu)-O$^t$Bu.

| Starting compound (mg) | Reaction Conditions | | Product (mg) |
| --- | --- | --- | --- |
| a) N-15 (400) | myristic acid HOBT WSC DCM 20° C. | 89 mg 58 mg 82 mg 6.7 ml 18 h | 17a (399) |
| b) 17a (300) | TFA 20° C. | 3.0 ml 3.0 h | 17 (259) |

Compound 17a: $[\alpha]_D^{24}$ –10.6° (c=0.53, in chloroform)

Elemental Analysis for $C_{69}H_{128}N_4O_{12}S\cdot0.5H_2O$: Calcd.: C, 66.47; H, 10.43; N, 4.49; S, 2.57 Found: C, 66.56; H, 10.44; N, 4.69; S, 2.61

Compound 17: $[\alpha]_D^{24}$ –17.7° (c=0.50, in 5% TFA-chloroform)

Elemental Analysis for $C_{61}H_{112}N_4O_{12}S$: Calcd.: C, 65.01; H, 10.03; N, 4.98; S, 2.85 Found: C, 64.97; H, 9.73; N, 5.09; S, 2.78

Example 25

Production of (2R,6R)-2-Myr-amino-6,7-bis(PamO)-4-THT-Gly-Gly-OH (Compound 18)

In substantially the same manner as in Example 9, starting from (2R,6R)-2-amino-6,7-bis(PamO)-4-THT-Gly-Gly-O'Bu (N-16), Compound 18 was produced via (2R,6R)-2-Myr-amino-6,7-bis(PamO)-4-THT-Gly-Gly-O'Bu (18a).

| Starting compound (mg) | Reaction Conditions | | Product (mg) |
| --- | --- | --- | --- |
| a) N-16 (700) | myristic acid HOBT WSC DCM 20° C. | 209 mg 124 mg 175 mg 10.0 ml 18 h | 18a (807) |
| b) 18a (600) | TFA 20° C. | 6.0 ml 1.0 h | 18 (527) |

Compound 18a: $[\alpha]_D^{24}$ −8.9° (c=0.50, in chloroform)

Elemental Analysis for $C_{60}H_{113}N_3O_9S$: Calcd.: C, 68.46; H, 10.82; N, 3.99; S, 3.05 Found: C, 68.49; H, 10.68; N, 3.96; S, 2.85

Compound 18: $[\alpha]_D^{25}$ −13.8° (c=0.55, in 5% TFA-chloroform)

Elemental Analysis for $C_{46}H_{87}N_3O_8S \cdot 0.5H_2O$: Calcd.: C, 64.90; H, 10.42; N, 4.94; S, 3.77 Found: C, 64.99; H, 10.45; N, 4.82; S, 3.49

Example 26

Production of (2R,6R)-2-Myr-amino-6,7-bis(PamO)-4-THT-Gly-Glu-OH (Compound 19)

In substantially the same manner as in Example 9, starting with (2R,6R)-2-amino-6,7-bis(PamO)-4-THT-Gly-Glu(O'Bu)-O'Bu (N-17), Compound 19 was produced via (2R,6R)-2-Myr-amino-6,7-bis(PamO)-4-THT-Gly-Glu(O'Bu)-O'Bu (19a).

| Starting compound (mg) | Reaction Conditions | | Product (mg) |
| --- | --- | --- | --- |
| a) N-17 (400) | myristic acid HOBT WSC DCM 20° C. | 94 mg 61 mg 87 mg 6.7 ml 20 h | 19a (379) |
| b) 19a (300) | TFA 20° C. | 3.0 ml 3.0 h | 19 (256) |

Compound 19a: $[\alpha]_D^{22}$ −1.8° (c=0.55, in chloroform)

Elemental Analysis for $C_{67}H_{125}N_3O_{11}S$: Calcd.: C, 68.15; H, 10.67; N, 3.56; S, 2.72 Found: C, 67.87; H, 10.72; N, 3.43; S, 2.67

Compound 19a: $[\alpha]_D^{21}$ −13.3° (c=0.51, in 5% TFA-chloroform]

Elemental Analysis for $C_{59}H_{109}N_3O_{11}S \cdot 0.5 H_2O$: Calcd.: C, 65.76; H, 10.29; N, 3.90; S, 2.98 Found: C, 65.84; H, 10.32; N, 3.92; S, 2.97

Example 27

Production of (2R,6R)-2-Myr-amino-6,7-bis(PamO)-4-THT-Gly-D-Glu-OH (Compound 20)

In substantially the same manner as in Example 9, starting from (2R,6R)-2-amino-6,7-bis(PamO)-4-THT-Gly-D-Glu(O'Bu)-O'Bu (N-18), Compound 20 was produced via (2R,6R)-2-Myr-amino-6,7-bis(PamO)-4-THT-Gly-D-Glu(O'Bu)-O'Bu (20a).

| Starting compound (mg) | Reaction Conditions | | Product (mg) |
| --- | --- | --- | --- |
| a) N-18 (600) | myristic acid HOBT WSC DCM 20° C. | 141 mg 92 mg 118 mg 10.0 ml 18 h | 20a (582) |
| b) 20a (500) | TFA 20° C. | 5.0 ml 3.0 h | 20 (439) |

Compound 20a: $[\alpha]_D^{24}$ −13.3° (c=0.52, in chloroform)

Elemental Analysis for $C_{67}H_{125}N_3O_{11}S$: Calcd.: C, 68.15; H, 10.67; N, 3.56; S, 2.72 Found: C, 67.97; H, 11.07; N, 3.49; S, 2.71

Compound 20: $[\alpha]_D^{24}$ −19.5° (c=0.51, in 5% TFA-chloroform)

Elemental Analysis for $C_{59}H_{109}N_3O_{11}S$: Calcd.: C, 66.32; H, 10.28; N, 3.93; S, 3.00 Found: C, 66.41; H, 10.19; N, 3.95; S, 2.91

Example 28

Production of (2R,6R)-2-Myr-amino-6,7-bis(PamO)-4-THT-Glu-OH (Compound 21)

In substantially the same manner as in Example 9, starting from (2R,6R)-2-amino-6,7-bis(PamO)-4-THT-Glu(O'Bu)-O'Bu (N-19), Compound 21 was produced via (2R,6R)-2-Myr-amino-6,7-bis(PamO)-4-THT-Glu(O'Bu)-O'Bu (21a).

| Starting compound (mg) | Reaction Conditions | | Product (mg) |
| --- | --- | --- | --- |
| a) N-19 (530) | myristic acid HOBT WSC DCM 20° C. | 145 mg 86 mg 122 mg 10.0 ml 24 h | 21a (586) |
| b) 21a (540) | TFA 20° C. | 5.0 ml 1.5 h | 21 (474) |

Compound 21a: $[\alpha]_D^{23}$ −4.9° (c=0.58, in chloroform)

Elemental Analysis for $C_{65}H_{122}N_2O_{10}S$: Calcd.: C, 69.47; H, 10.94; N, 2.49; S, 2.85 Found: C, 69.34; H, 10.83; N, 2.41; S, 2.77

Compound 21: $[\alpha]_D^{21}$ −13.4° (c=0.54, in 5% TFA-chloroform)

Elemental Analysis for $C_{57}H_{106}N_2O_{10}S$: Calcd.: C, 67.62; H, 10.56; N, 2.77; S, 3.17 Found: C, 67.50; H, 10.32; N, 2.72; S, 3.20

Example 29

Production of (2R,6R)-2-Myr-amino-6,7-bis(PamO)-4-THT-D-Glu-OH (Compound 22)

In substantially the same manner as in Example 9, starting from (2R,6R)-2-amino-6,7-bis(PamO)-4-THT-D-Glu(O ᵗBu)-OᵗBu (N-20), Compound 22 was produced via (2R, 6R)-2-Myr-amino-6,7-bis(PamO)-4-THT-D-Glu(OᵗBu)-O ᵗBu (22a).

| Starting compound (mg) | Reaction Conditions | | Product (mg) |
| --- | --- | --- | --- |
| a) N-20 (790) | myristic acid HOBT WSC DCM 20° C. | 217 mg 129 mg 183 mg 12.0 ml 15 h | 22a (801) |
| b) 22a (657) | TFA 20° C. | 7.0 ml 2.0 h | 22 (529) |

Compound 22a: $[\alpha]_D^{22}$ –7.1° (c=0.65, in chloroform)
Elemental Analysis for $C_{65}H_{122}N_2O_{10}S \cdot 0.5H_2O$: Calcd.: C, 68.92; H, 10.95; N, 2.47; S, 2.83 Found: C, 68.94; H, 10.93; N, 2.98; S, 2.53

Compound 22: $[\alpha]_D^{25}$ –19.1° (c=0.63, in 5% TFA-chloroform)
Elemental Analysis for $C_{57}H_{106}N_2O_{10}S \cdot 0.5H_2O$: Calcd.: C, 67.09; H, 10.57; N, 2.75; S, 3.14 Found: C, 66.96; H, 10.44; N, 2.76; S, 3.01

Example 30

Production of (2R,6R)-2-Myr-amino-6,7-bis(PamO)-4-THT-Asp-OH (Compound 23)

In substantially the same manner as in Example 9, starting from (2R,6R)-2-amino-6,7-bis(PamO)-4-THT-Asp(O ᵗBu)-OᵗBu (N-21), Compound 23 was produced via (2R,6R)-2-Myr-amino-6,7-bis(PamO)-4-THT-Asp(OᵗBu)-OᵗBu (23a).

| Starting compound (mg) | Reaction Conditions | | Product (mg) |
| --- | --- | --- | --- |
| a) N-21 (600) | myristic acid HOBT WSC DCM 20° C. | 168 mg 99 mg 141 mg 10.0 ml 15 h | 23a (725) |
| b) 23a (605) | TFA 20° C. | 6.0 ml 2.0 h | 23 (520) |

Compound 23a: $[\alpha]_D^{22}$ +6.0° (c=0.63, in chloroform)
Elemental Analysis for $C_{64}H_{120}N_2O_{10}S$: Calcd.: C, 69.27; H, 10.90; N, 2.52; S, 2.89 Found: C, 69.29; H, 10.98; N, 2.57; S, 2.72

Compound 23: $[\alpha]_D^{25}$ –4.7° (c=0.56, in 5% TFA-chloroform)
Elemental Analysis for $C_{56}H_{104}N_2O_{10}S \cdot 0.5H_2O$: Calcd.: C, 66.83; H, 10.52; N, 2.78; S, 3.19 Found: C, 66.90; H, 10.37; N, 2.79; S, 2.94

Example 31

Production of (2R,6R)-2-Myr-amino-6,7-bis(PamO)-4-THT-D-Asp-OH (Compound 24)

In substantially the same manner as in Example 9, starting from (2R,6R)-2-amino-6,7-bis(PamO)-4-THT-D-Asp(O ᵗBu)-OᵗBu (N-22), Compound 24 was produced via (2R, 6R)-2-Myr-amino-6,7-bis(PamO)-4-THT-D-Asp(OᵗBu)-O ᵗBu (24a).

| Starting compound (mg) | Reaction Conditions | | Product (mg) |
| --- | --- | --- | --- |
| a) N-22 (607) | myristic acid HOBT WSC DCM 20° C. | 170 mg 100 mg 142 mg 10.0 ml 15 h | 24a (653) |
| b) 24a (590) | TFA 20° C. | 6.0 ml 2.0 h | 24 (490) |

Compound 24a: $[\alpha]_D^{22}$ –13.1° (c=0.62, in chloroform)
Elemental Analysis for $C_{64}H_{120}N_2O_{10}S \cdot 0.5H_2O$: Calcd.: C, 68.71; H, 10.91; N, 2.50; S, 2.87 Found: C, 68.98; H, 10.71; N, 2.68; S, 2.66

Compound 24: $[\alpha]_D^{25}$ –22.5° (c=0.56, in 5% TFA-chloroform)
Elemental Analysis for $C_{56}H_{104}N_2O_{10}S \cdot 0.5H_2O$: Calcd.: C, 66.83; H, 10.52; N, 2.78; S, 3.19 Found: C, 66.55; H, 10.38; N, 2.76; S, 3.05

Example 32

Production of (2R,6R)-2-Myr-amino-6,7-bis(PamO)-4-THT-OH (Compound 25)

In substantially the same manner as in Example 9, starting from (2R,6R)-2-amino-6,7-bis(PamO)-4-THT-OᵗBu N-23), Compound 25 was produced via (2R,6R)-2-Myr-amino-6,7-bis(PamO)-4-THT-OᵗBu (25a).

| Starting compound (mg) | Reaction Conditions | | Product (mg) |
| --- | --- | --- | --- |
| a) N-23 (600) | myristic acid HOBT WSC DCM 20° C. | 207 mg 122 mg 174 mg 10.0 ml 20 h | 25a (722) |
| b) 25a (600) | TFA 20° C. | 6.0 ml 1.5 h | 25 (552) |

Compound 25a: $[\alpha]_D^{24}$ +7.0° (c=0.50, in chloroform)
Elemental Analysis for $C_{56}H_{107}NO_7S$: Calcd.: C, 71.67; H, 11.49; N, 1.49; S, 3.42 Found: C, 71.44; H, 11.43; N, 1.41; S, 3.37

Compound 25: $[\alpha]_D^{25}$ +4.2° (c=0.64, in 5% TFA-chloroform)
Elemental Analysis for $C_{52}H_{99}NO_7S$: Calcd.: C, 70.78; H, 11.31; N, 1.59; S, 3.63 Found: C, 70.83; H, 11.59; N, 1.65; S, 3.77

Example 33

Production of (2R,6R)-2-Myr-amino-6,7-bis(PamO)-4-Gly-Glu-Glu-OH (Compound 26) (SEQ ID No. 103)

In substantially the same manner as in Example 9, starting from (2R,6R)-2-amino-6,7-bis(PamO)-4-THT-Gly-Glu(O ᵗBu)-Glu(OᵗBu)-OᵗBu (N-24) (SEQ ID No. 6), Compound 26 was produced via (2R,6R)-2-Myr-amino-6,7-bis(PamO)-4-THT-Gly-Glu(O ᵗBu)-Glu(OᵗBu)-OᵗBu (26a) (SEQ ID No. 6).

| Starting compound (mg) | Reaction Conditions | | Product (mg) |
|---|---|---|---|
| a) N-24 (400) | myristic acid HOBT WSC DCM 20° C. | 79 mg 52 mg 73 mg 6.7 ml 16 h | 26a (360) |
| b) 26a (280) | TFA 20° C. | 6.0 ml 3.0 h | 26 (228) |

Compound 26a: $[\alpha]_D^{24}$ –7.0° (c=0.52, in chloroform)
Elemental Analysis for $C_{76}H_{140}N_4O_{14}S$: Calcd.: C, 66.82; H, 10.33; N, 4.10; S, 2.35 Found: C, 66.56; H, 10.29; N, 4.08; S, 2.13
Compound 26: $[\alpha]_D^{24}$ –19.1° (c=0.53, in 5% TFA-chloroform)
Elemental Analysis for $C_{64}H_{116}N_4O_{14}S \cdot 0.5H_2O$: Calcd.: C, 63.70; H, 9.77; N, 4.64; S, 2.66 Found: C, 63.80; H, 9.76; N, 4.76; S, 2.66

Example 34

Production of (2R,6R)-2-Myr-amino-6,7-bis(PamO)-4-Gly-Glu-D-Glu-OH (Compound 27)

In substantially the same manner as in Example 9, starting from (2R,6R)-2-amino-6,7-bis(PamO)-4-THT-Gly-Glu(O$^t$Bu)-D-Glu(O$^t$Bu)-O$^t$Bu (N-25), Compound 27 was produced via (2R,6R)-2-Myr-amino-6,7-bis(PamO)-4-THT-Gly-Glu(O$^t$Bu)-D-Glu(O$^t$Bu)-O$^t$Bu (27a)

| Starting compound (mg) | Reaction Conditions | | Product (mg) |
|---|---|---|---|
| a) N-25 (300) | myristic acid HOBT WSC DCM 20° C. | 59 mg 39 mg 55 mg 5.0 ml 15 h | 27a (275) |
| b) 27a (200) | TFA 20° C. | 2.0 ml 3.0 h | 27 (173) |

Compound 27a: $[\alpha]_D^{24}$ –13.0° (c=0.52, in chloroform)
Elemental Analysis for $C_{76}H_{140}N_4O_{14}S \cdot H_2O$: Calcd.: C, 65.95; H, 10.34; N, 4.05; S, 2.32 Found: C, 65.82; H, 10.26; N, 3.95; S, 2.29
Compound 27: $[\alpha]_D^{24}$ –20.8° (c=0.48, in 5% TFA-chloroform)
Elemental Analysis for $C_{64}H_{116}N_4O_{14}S \cdot 1.5H_2O$: Calcd.: C, 62.77; H, 9.79; N, 4.58; S, 2.62 Found: C, 62.55; H, 9.64; N, 4.69; S, 2.71

Example 35

Production of (2R,6R)-2-Myr-amino-6,7-bis(PamO)-4-THT-Glu-Gly-Glu-OH (Compound 28) (SEQ ID No. 104)

In substantially the same manner as in Example 9, starting from (2R,6R)-2-amino-6,7-bis(PamO)-4-THT-Glu(O $^t$Bu)-Gly-Glu(O$^t$Bu)-O$^t$Bu (N-26) (SEQ ID No. 3), Compound 28 was produced via (2R,6R)-2-Myr-amino-6,7-bis(PamO)-4-THT-Glu(O $^t$Bu)-Gly-Glu(O$^t$Bu)-O$^t$Bu (28a) (SEQ ID No. 3).

| Starting compound (mg) | Reaction Conditions | | Product (mg) |
|---|---|---|---|
| a) N-26 (550) | myristic acid HOBT WSC DCM 20° C. | 109 mg 71 mg 101 mg 9.2 ml 16 h | 28a (533) |
| b) 28a (450) | TFA 20° C. | 4.5 ml 3.0 h | 28 (379) |

Compound 28a: $[\alpha]_D^{24}$ –5.2° (c=0.53, in chloroform)
Elemental Analysis for $C_{76}H_{140}N_4O_{14}S$: Calcd.: C, 66.82; H, 10.33; N, 4.10; S, 2.35 Found: C, 66.66; H, 10.23; N, 4.09; S, 2.46
Compound 28: $[\alpha]_D^{24}$ –17.9° (c=0.51, in 5% TFA-chloroform)
Elemental Analysis for $C_{64}H_{116}N_6O_{14}S \cdot 0.5H_2O$: Calcd.: C, 63.70; H, 9.77; N, 4.64; S, 2.66 Found: C, 63.79; H, 9.61; N, 4.75; S, 2.65

Example 36

Production of (2R,6R)-2-Myr-amino-6,7-bis(PamO)-4-THT-Glu-Gly-D-Glu-OH (Compound 29)

In substantially the same manner as in Example 9, starting from (2R,6R)-2-amino-6,7-bis(PamO)-4-THT-Glu(O $^t$Bu)-Gly-D-Glu(O$^t$Bu)-O$^t$Bu (N-8), Compound 29 was produced via (2R,6R)-2-Myr-amino-6,7-bis(PamO)-4-THT-Glu(O $^t$Bu)-Gly-D-Glu(O$^t$Bu)-O$^t$Bu (29a).

| Starting compound (mg) | Reaction Conditions | | Product (mg) |
|---|---|---|---|
| a) N-8 (800) | myristic acid HOBT WSC DCM 20° C. | 152 mg 99 mg 141 mg 13 ml 20 h | 29a (732) |
| b) 29a (600) | TFA 20° C. | 6.0 ml 3.0 h | 29 (522) |

Compound 29a: $[\alpha]_D^{22}$ –7.7° (c=0.52, in chloroform)
Elemental Analysis for $C_{76}H_{140}N_4O_{14}S$: Calcd.: C, 66.82; H, 10.33; N, 4.10; S, 2.35 Found: C, 66.64; H, 10.41; N, 4.16; S, 2.34
Compound 29: $[\alpha]_D^{21}$ –18.9° (c=0.55, in 5% TFA-chloroform)
Elemental Analysis for $C_{64}H_{116}N_6O_{14}S$: Calcd.: C, 64.18; H, 9.76; N, 4.68; S, 2.68 Found: C, 64.14; H, 9.88; N, 4.58; S, 2.71

Example 37

Production of (2R,6R)-2-Myr-amino-6,7-bis(PamO)-4-THT-Glu-Glu-OH (Compound 30)

In substantially the same manner as in Example 9, starting from (2R,6R)-2-amino-6,7-bis(PamO)-4-THT-Glu(O $^t$Bu)-Glu(O$^t$Bu)-O$^t$Bu (N-27), Compound 30 was produced via (2R,6R)-2-Myr-amino-6,7-bis(PamO)-4-THT-Glu(O $^t$Bu)-Glu(O$^t$Bu)-O$^t$Bu (30a).

| Starting compound (mg) | Reaction Conditions | | Product (mg) |
|---|---|---|---|
| a) N-27 (550) | myristic acid HOBT WSC DCM 20° C. | 114 mg 75 mg 106 mg 9.2 ml 16 h | 30a (538) |
| b) 30a (450) | TFA 20° C. | 4.5 ml 3.0 h | 30 (377) |

Compound 30a: $[\alpha]_D^{25}$ –6.3° (c=0.54, in chloroform)
Elemental Analysis for $C_{74}H_{137}N_3O_{13}S$: Calcd.: C, 67.90; H, 10.55; N, 3.21; S, 2.45 Found: C, 67.86; H, 10.20; N, 2.93; S, 2.49

Compound 30: $[\alpha]_D^{24}$ –23.3° (c=0.51, in 5% TFA-chloroform)
Elemental Analysis for $C_{62}H_{113}N_3O_{13}S$: Calcd.: C, 65.29; H, 9.99; N, 3.68; S, 2.81 Found: C, 65.15; H, 10.11; N, 3.76; S, 2.60

Example 38

Production of (2R,6R)-2-Myr-amino-6,7(PamO)-4-THT-Glu-D-Glu-OH (Compound 31)

In substantially the same manner as in Example 9, starting from (2R,6R)-2-amino-6,7-bis(PamO)-4-THT-Glu(O $^t$Bu)-D-Glu(O$^t$Bu)-O$^t$Bu (N-28), Compound 31 was produced via (2R,6R)-2-Myr-amino-6,7-bis(PamO)-4-THT-Glu(O $^t$Bu)-D-Glu(O$^t$Bu)-O$^t$Bu (31a).

| Starting compound (mg) | Reaction Conditions | | Product (mg) |
|---|---|---|---|
| a) N-28 (450) | myristic acid HOBT WSC DCM 20° C. | 94 mg 61 mg 87 mg 7.5 ml 15 h | 31a (455) |
| b) 31a (350) | TFA 20° C. | 3.5 ml 3.0 h | 31 (300) |

Compound 31a: $[\alpha]_D^{24}$ –10.5° (c=0.53, in chloroform)
Elemental Analysis for $C_{74}H_{137}N_3O_{13}S$: Calcd.: C, 67.90; H, 10.55; N, 3.21; S, 2.45 Found: C, 67.74; H, 10.32; N, 3.43; S, 2.52

Compound 31: $[\alpha]_D^{24}$ –24.4° (c=0.50, in 5% TFA-chloroform)
Elemental Analysis for $C_{62}H_{113}N_3O_{13}S$: Calcd.: C, 65.29; H, 9.99; N, 3.68; S, 2.81 Found: C, 65.40; H, 9.72; N, 3.66; S, 2.66

Example 39

Production of (2R,6R)-2-Myr-amino-6,7-bis(PamO)-4-THT-Glu-Gly-Glu-Gly-D-Glu-OH (Compound 32)

In substantially the same manner as in Example 9, starting from (2R,6R)-2-amino-6,7-bis(PamO)-4-THT-Glu(O $^t$Bu)-Gly-Glu(O$^t$Bu)-Gly-D-Glu(O$^t$Bu)-O$^t$Bu (N-29), Compound 32 was produced via (2R,6R)-2-Myr-amino-6,7-bis(PamO)- 4-THT-Glu(O$^t$Bu)-Gly-Glu(O$^t$Bu)-Gly-D-Glu(O$^t$Bu)-O $^t$Bu (32a).

| Starting compound (mg) | Reaction Conditions | | Product (mg) |
|---|---|---|---|
| a) N-29 (250) | myristic acid HOBT WSC DCM 20° C. | 41 mg 27 mg 38 mg 4.2 ml 20 h | 32a (239) |
| b) 32a (180) | TFA 20° C. | 2.0 ml 3.0 h | 32 (149) |

Compound 32a: $[\alpha]_D^{22}$ +1.7° (c=0.58, in chloroform)
Elemental Analysis for $C_{87}H_{158}N_6O_{18}S$: Calcd.: C, 64.97; H, 9.90; N, 5.22; S, 1.99 Found: C, 64.67; H, 9.94; N, 5.18; S, 1.77

Compound 32: $[\alpha]_D^{21}$ –20.7° (c=0.56, in 5% TFA-chloroform)
Elemental Analysis for $C_{71}H_{126}N_6O_{18}S \cdot 0.5H_2O$: Calcd.: C, 61.22; H, 9.19; N, 6.03; S, 2.30 Found: C, 61.23; H, 9.22; N, 6.01; S, 2.32

Example 40

Production of (2R,6R)-2-Myr-amino-6,7-bis(PamO)-4-THT-Glu-Glu-Glu-OH (Compound 33) (SEQ ID No. 105)

In substantially the same manner as in Example 9, starting from (2R,6R)-2-amino-6,7-bis(PamO)-4-THT-Glu(O $^t$Bu)-Glu(O$^t$Bu)-Glu(O$^t$Bu)-O$^t$Bu (N-30) (SEQ ID No. 70), Compound 33 was produced via (2R,6R)-2-Myr-amino-6,7-bis-(PamO)-4-THT-Glu(O $^t$Bu)-Glu(O$^t$Bu)-Glu(O$^t$Bu)-O$^t$Bu (33a) (SEQ ID No. 70).

| Starting compound (mg) | Reaction Conditions | | Product (mg) |
|---|---|---|---|
| a) N-30 (500) | myristic acid HOBT WSC DCM 20° C. | 87 mg 57 mg 81 mg 8.3 ml 16 h | 33a (486) |
| b) 33a (400) | TFA 20° C. | 4.0 ml 3.0 h | 33 (325) |

Compound 33a: $[\alpha]_D^{24}$ –12.8° (c=0.52, in chloroform)
Elemental Analysis for $C_{83}H_{152}N_4O_{16}S$: Calcd.: C, 66.72; H, 10.25; N, 3.75; S, 2.15 Found: C, 66.47; H, 10.19; N, 3.73; S, 2.12

Compound 33: $[\alpha]_D^{24}$ –26.3° (c=0.51, in 5% TFA-chloroform)
Elemental Analysis for $C_{67}H_{120}N_4O_{16}S$: Calcd.: C, 63.38; H, 9.53; N, 4.41; S, 2.53 Found: C, 63.10; H, 9.70; N, 4.54; S, 2.56

Example 41

Production of (2R,6R)-2-Myr-amino-6,7-bis(PamO)-4-THT-Glu-Glu-D-Glu-OH (Compound 34)

In substantially the same manner as in Example 9, starting from (2R,6R)-2-amino-6,7-bis(PamO)-4-THT-Glu(O 'Bu)-Glu(O'Bu)-D-Glu(O'Bu)-O'Bu (N-31), Compound 34 was produced via (2R,6R)-2-Myr-amino-6,7-bis(PamO)-4-THT-Glu(O 'Bu)-Glu(O'Bu)-D-Glu('Bu)-O'Bu (34a).

| Starting compound (mg) | Reaction Conditions | | Product (mg) | |
|---|---|---|---|---|
| a) N-31 (400) | myristic acid HOBT WSC DCM 20° C. | 70 mg 46 mg 65 mg 6.7 mg 17 h | 34a (377) | |
| b) 34a (300) | TFA 20° C. | 3.0 ml 3.0 h | 34 (250) | |

Compound 34a: $[\alpha]_D^{24}$ –10.8° (c=0.53, in chloroform)

Elemental Analysis for $C_{83}H_{152}N_4O_{16}S$: Calcd.: C, 66.72; H, 10.25; N, 3.75; S, 2.15 Found: C, 66.60; H, 10.29; N, 3.63; S, 2.19

Compound 34: $[\alpha]_D^{24}$ –29.5° (c=0.52, in 5% TFA-chloroform)

Elemental Analysis for $C_{67}H_{120}N_4O_{16}S$: Calcd.: C, 63.38; H, 9.53; N, 4.41; S, 2.53 Found: C, 63.30; H, 9.36; N, 4.38; S, 2.39

Example 42

Production of (2R,6R)-2-Myr-amino-6,7-bis(PamO)-4-THT-Glu(O 'Bu)-Gly-D-Glu(O'Bu)-O'Bu (Compound 29a)

In DMF (2.0 ml) were dissolved (2R,6R)-2-Myr-amino-6,7-bis(PamO)-4-THT-OH (25) (200 mg) and H-Glu(O ,Bu)-Gly-D-Glu(O'Bu)-O'Bu (126 mg). To the solution were added, under ice-cooling, HONB (45 mg) and DIC (39 μl). The mixture was stirred for 16 hours at 20° C. The reaction mixture was concentrated and dissolved in chloroform. The solution was washed with a 10% aqueous solution of citric acid, a saturated aqueous solution of sodium hydrogencarbonate and water, successively. The chloroform layer was dried over anhydrous sodium sulfate, which was concentrated. The concentrate was suspended in acetonitrile, which was subjected to filtration to afford (2R,6R)-2-Myr-amino-6,7-bis(PamO)-4-THT-Glu(O'Bu)-Gly-D-Glu(O'Bu)-O'Bu (29a) as a white powdery product (288 mg, yield 93%).

Example 43

Synthesis of (2R,6R)-$N^\delta$-(2-Pam-amino-6,7-bis(PamO)-4-THT)-Orn-Gly-Gly-Glu-OH hydrochloride (Compound 35) (SEQ ID No. 106)

a) (2R,6R)-2-Pam-amino-6,7-bis(PamO)-4-thiaheptanoic acid (120 mg) which was synthesized according to the method of Hoppe-Seyler's Zeitschrift für Physiologische Chemie, Vol. 364, p. 593 (1983), $N^\alpha$-Boc-Orn-Gly-Gly-Glu(O 'Bu)-O'Bu hydrochloride (SEQ ID No. 10) (91 mg) obtained in Reference Example 1, DEPC (35 mg) and TEA (55 mg) were dissolved in DMF (6 ml)-DCM (0.5 ml) mixture. This solution was stirred at 20° C. for one hour. After removing the solvent under reduced pressure, the residue was purified by means of a silica gel column chromatography (chloroform:methanol =30:1) to give (2R,6R)-$N^\delta$-(2-Pam-amino-6,7-bis(PamO)-4-THT)-$N^\alpha$-Boc-Orn-Gly-Gly-Glu(O ,Bu)-O'Bu (35a) (SEQ ID No. 106) (127 mg, 65%) as a colorless wax.

IR (neat) v: 3300, 2920, 2850, 1735, 1640, 1530, 1465, 1390, 1365, 1245, 1160 cm$^{-1}$ $^1$H-NMR (CDCl$_3$) δ: 0.88 (9H,t,J=6.8 Hz), 1.26(72H,s), 1.42 (9H,s), 1.44 (9H,s), 1.47 (9H,s), 1.20–1.70 (10H,m), 1.85–2.20 (2H,m), 2.25–2.40 (8H,m), 2.65–3.00 (4H,m), 3.15 (1H,m), 3.47 (1H,m), 3.75–4.70 (9H,m), 5.20 (1H,m), 5.53 (1H,d,J=7.0 Hz), 6.94 (1H,d,J=8.0 Hz), 7.14 (1H,m), 7.27 (1H,m), 7.70 (1H,m)

b) Compound 35a (125 mg) was dissolved in 4N hydrochloric acid ethyl acetate solution (5 ml). This solution was stirred at 20° C. for 3 hours and then the solvent was removed under reduced pressure to give compound 35 (106 mg, 96%) as a white powder. m.p. 203°–205° C. $[\alpha]_D^{20}$+1.5° (c=0.305, in chloroform)

IR (KBr) v: 3295, 3066, 2920, 2852, 1733, 1653, 1538, 1463, 1241 cm$^{-1}$ $^1$H-NMR (CDCl$_3$-TFA) δ: 0.88 (9H,t,J=6.6 Hz), 1.25 (72H,s), 1.40–1.80 (10H,m), 1.85–3.10 (15H,m), 3.15– 3.50 (1H,m), 3.80–4.70 (9H,m), 5.21 (1H,m), 7.30–7.85 (5H,m)

Formulation Example 1

Using TAN-1511A produced in Example 2, all the ingredients shown by the following prescription were mixed and filled in gelatin capsules, so that capsules containing 30 mg of TAN-1511A per capsule were prepared.

| TAN-1511A | 30 mg |
|---|---|
| Lactose | 100 mg |
| Corn starch | 40 mg |
| Magnesium stearate | 10 mg |
| Total | 180 mg |

Formulation Example 2

TAN-1511A produced in Example 2 and magnesium stearate were granulated with an aqueous solution of soluble starch. The granules were dried, which was mixed with lactose and corn starch. The mixture was subjected to compression molding to prepare tablets shown by the following prescription.

| TAN-1511A | 30 mg |
|---|---|
| Lactose | 65 mg |
| Corn starch | 30 mg |
| Soluble starch | 35 mg |
| Magnesium stearate | 20 mg |
| Total | 180 mg |

Formulation Example 3

TAN-1511A produced in Example 2 was dissolved in a physiological saline solution containing 30% (W/V) polyethylene glycol 400 to prepare a 0.05% solution of TAN-1511A . The solution was subjected to filtration under sterilization, and 30 ml each of which was then distributed into one vial to prepare intravenous injection containing 15 mg of TAN-1511A per vial.

Formulation Example 4

The compound 16 (40 mg) obtained in Example 23 and mannitol (50 g) were dissolved in sterilized distilled water (1 liter) containing polyethylene glycol 400 (30% w/w). The solution was subjected to filtration under sterilization, and 1 ml each of which was then distributed in one ampoule to prepare intravenous injection containing 40 μg of the compound 16 per ampoule.

What is claimed is:

1. A compound of the formula:

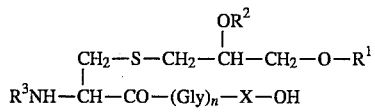

wherein each $R^1$ $R^2$ and $r^3$ is an aliphatic acyl group, X is an amino acid sequence consisting of 1 to 4 amino acid residues, the N-terminal amino acid residue of said sequence being an acidic amino acid residue, the remaining amino acid residues of said sequence being selected from the group consisting of glycyl, alanyl, prolyl, leucyl and threonyl, and n is 3, or a salt thereof.

2. The compound according to claim 1, wherein the aliphatic acyl group is $C_{7-23}$ aliphatic acyl group.

3. The compound according to claim 1, wherein the acidic amino acid residue has one amino group and two or more carboxyl groups.

4. The compound according to claim 1, wherein the compound is (2R,6R)-2-tetradecanoylamino-6,7-bis(hexadecanoyloxy)-4-thiaheptanoyl-glycyl-glycyl-glycyl-glutamyl-threonyl-threonine (SEQ ID No. 64.

5. The compound according to claim 1, wherein the compound is (2R,6R)-2-tetradecanoylamino-6,7-bis(hexadecanoyloxy)-4-thiaheptanoyl-glycyl-glycyl-glycyl-glutamyl acid (SEQ ID. No. 65).

6. An immuno-stimulating composition having a leukocyte-increasing action, which comprises a compound or its salt as claimed in claim 1 and a pharmaceutically acceptable carrier, excipient or diluent.

7. The compound according to claim 1, wherein X is an amino acid sequence consisting of 1 to 4 amino acid residues, the N-terminal amino acid residue of said sequence being glutamyl or aspartyl, and the remaining amino acid residues of said sequence being selected from the group consisting of glycyl, alanyl and threonyl.

\* \* \* \* \*

SEQUENCE LISTING ( 1 ) GENERAL INFORMATION:

( i i i ) NUMBER OF SEQUENCES: 106

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:1:

Xaa Ser Ser Asn Ala
1                 5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:2:

Xaa Asn Ser Gly Gly Ser
1                 5

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:3:

Xaa Glu Gly Xaa
1

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:4:

Xaa Glu Gly Xaa Xaa
1                   5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:5:

Xaa Glu Gly Xaa Xaa Xaa
1                   5

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:6:

Xaa Gly Xaa Xaa
1

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:7:

Xaa Gly Xaa Xaa Xaa
1                   5

( 2 ) INFORMATION FOR SEQ ID NO:8:

( i ) SEQUENCE CHARACTERISTICS:

(A) LENGTH: 6 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:8:

Xaa Gly Xaa Xaa Xaa Xaa
1               5

(2) INFORMATION FOR SEQ ID NO:9:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:9:

Xaa Gly Xaa Xaa Xaa Xaa Xaa
1               5

(2) INFORMATION FOR SEQ ID NO:10:

(i) SEQUENCE CHARACTERISTICS:
(A) LENGTH: 4 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:10:

Xaa Gly Gly Xaa
1

(2) INFORMATION FOR SEQ ID NO:11:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:11:

Xaa Gly Gly Xaa Xaa
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:12:

Xaa Gly Gly Xaa Xaa Xaa
1                 5

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:13:

Xaa Gly Gly Xaa Xaa Xaa Xaa
1                 5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:14:

Xaa Gly Gly Xaa Xaa Xaa Xaa Xaa
1                 5

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:15:

Xaa Gly Gly Gly Xaa
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
        described in specification"

( x i ) SEQUENCE DESCRIPTION: SEQ ID NO:16:

Xaa Gly Gly Gly Xaa Xaa
1               5

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
        described in specification"

( x i ) SEQUENCE DESCRIPTION: SEQ ID NO:17:

Xaa Gly Gly Gly Xaa Xaa Xaa
1               5

( 2 ) INFORMATION FOR SEQ ID NO:18:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
        described in specification"

( x i ) SEQUENCE DESCRIPTION: SEQ ID NO:18:

Xaa Gly Gly Gly Xaa Xaa Xaa Xaa
1               5

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:

( A ) NAME/KEY: modified site
( B ) LOCATION:
( C ) IDENTIFICATION METHOD:
( D ) OTHER INFORMATION: /note ="Xaa is modified amino acid as described in specification"

( x i ) SEQUENCE DESCRIPTION: SEQ ID NO:19:

Xaa Gly Gly Gly Xaa Xaa Xaa Xaa Xaa
1                   5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:20:

Xaa Gly Gly Gly Gly Xaa
1                   5

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:21:

Xaa Gly Gly Gly Gly Xaa Xaa
1                   5

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:22:

Xaa Gly Gly Gly Gly Xaa Xaa Xaa
1                   5

( 2 ) INFORMATION FOR SEQ ID NO:23:

( i ) SEQUENCE CHARACTERISTICS:
        ( A ) LENGTH: 9 amino acids (B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:23:

Xaa  Gly  Gly  Gly  Gly  Xaa  Xaa  Xaa  Xaa
 1                      5

(2) INFORMATION FOR SEQ ID NO:24:

(i) SEQUENCE CHARACTERISTICS:
(A) LENGTH: 10 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:24:

Xaa  Gly  Gly  Gly  Gly  Xaa  Xaa  Xaa  Xaa  Xaa
 1                      5                          10

(2) INFORMATION FOR SEQ ID NO:25:

(i) SEQUENCE CHARACTERISTICS:
(A) LENGTH: 7 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:25:

Xaa  Gly  Gly  Gly  Glu  Thr  Thr
 1                      5

(2) INFORMATION FOR SEQ ID NO:26:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:26:

Xaa  Gly  Gly  Gly  Glu
 1                      5

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(xi) SEQUENCE DESCRIPTION: SEQ ID NO:27:

Xaa Gly Gly Glu
1

(2) INFORMATION FOR SEQ ID NO:28:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(xi) SEQUENCE DESCRIPTION: SEQ ID NO:28:

Xaa Gly Glu Glu
1

(2) INFORMATION FOR SEQ ID NO:29:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(xi) SEQUENCE DESCRIPTION: SEQ ID NO:29:

Xaa Glu Gly Glu
1

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

( x i ) SEQUENCE DESCRIPTION: SEQ ID NO:30:

Xaa  Glu  Gly  Xaa
1

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:31:

Xaa  Gly  Gly  Gly  Glu  Thr  Thr
1                   5

( 2 ) INFORMATION FOR SEQ ID NO:32:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:32:

Xaa  Gly  Gly  Gly  Asp  Ala  Gly  Thr
1                   5

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:33:

Xaa  Gly  Gly  Gly  Asp  Pro  Leu
1                   5

( 2 ) INFORMATION FOR SEQ ID NO:34:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site (B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:34:

Xaa Glu Gly Xaa
1

(2) INFORMATION FOR SEQ ID NO:35:

(i) SEQUENCE CHARACTERISTICS:
(A) LENGTH: 5 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:35:

Xaa Glu Gly Xaa Xaa
1               5

(2) INFORMATION FOR SEQ ID NO:36:

(i) SEQUENCE CHARACTERISTICS:
(A) LENGTH: 6 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:36:

Xaa Glu Gly Xaa Xaa Xaa
1               5

(2) INFORMATION FOR SEQ ID NO:37:

(i) SEQUENCE CHARACTERISTICS:
(A) LENGTH: 4 amino acids
(B) TYPE: amino acid
(C) STRANDEDNESS: single
(D) TOPOLOGY: linear (ix) FEATURE:
(A) NAME/KEY: modified site
(B) LOCATION:
(C) IDENTIFICATION METHOD:
(D) OTHER INFORMATION: /note ="Xaa is modified amino acid as described in specification"

(xi) SEQUENCE DESCRIPTION: SEQ ID NO:37:

Xaa Gly Xaa Xaa
1

(2) INFORMATION FOR SEQ ID NO:38:

(i) SEQUENCE CHARACTERISTICS:
(A) LENGTH: 5 amino acids
(B) TYPE: amino acid (C) STRANDEDNESS: single
(D) TOPOLOGY: linear (ix) FEATURE:
    (A) NAME/KEY: modified site
    (B) LOCATION:
    (C) IDENTIFICATION METHOD:
    (D) OTHER INFORMATION: /note ="Xaa is modified amino acid as
        described in specification"

(xi) SEQUENCE DESCRIPTION: SEQ ID NO:38:

Xaa Gly Xaa Xaa Xaa
1               5

(2) INFORMATION FOR SEQ ID NO:39:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as
            described in specification"

(xi) SEQUENCE DESCRIPTION: SEQ ID NO:39:

Xaa Gly Xaa Xaa Xaa Xaa
1               5

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as
            described in specification"

(xi) SEQUENCE DESCRIPTION: SEQ ID NO:40:

Xaa Gly Xaa Xaa Xaa Xaa Xaa
1               5

(2) INFORMATION FOR SEQ ID NO:41:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as
            described in specification"

(xi) SEQUENCE DESCRIPTION: SEQ ID NO:41:

Xaa Gly Gly Xaa
1

( 2 ) INFORMATION FOR SEQ ID NO:42:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i x ) FEATURE:
      ( A ) NAME/KEY: modified site
      ( B ) LOCATION:
      ( C ) IDENTIFICATION METHOD:
      ( D ) OTHER INFORMATION: /note ="Xaa is modified amino acid as
            described in specification"

( x i ) SEQUENCE DESCRIPTION: SEQ ID NO:42:

Xaa  Gly  Gly  Xaa  Xaa
 1                   5

( 2 ) INFORMATION FOR SEQ ID NO:43:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i x ) FEATURE:
      ( A ) NAME/KEY: modified site
      ( B ) LOCATION:
      ( C ) IDENTIFICATION METHOD:
      ( D ) OTHER INFORMATION: /note ="Xaa is modified amino acid as
            described in specification"

( x i ) SEQUENCE DESCRIPTION: SEQ ID NO:43:

Xaa  Gly  Gly  Xaa  Xaa  Xaa
 1                   5

( 2 ) INFORMATION FOR SEQ ID NO:44:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i x ) FEATURE:
      ( A ) NAME/KEY: modified site
      ( B ) LOCATION:
      ( C ) IDENTIFICATION METHOD:
      ( D ) OTHER INFORMATION: /note ="Xaa is modified amino acid as
            described in specification"

( x i ) SEQUENCE DESCRIPTION: SEQ ID NO:44:

Xaa  Gly  Gly  Xaa  Xaa  Xaa  Xaa
 1                   5

( 2 ) INFORMATION FOR SEQ ID NO:45:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i x ) FEATURE:
      ( A ) NAME/KEY: modified site
      ( B ) LOCATION:
      ( C ) IDENTIFICATION METHOD:
      ( D ) OTHER INFORMATION: /note ="Xaa is modified amino acid as
            described in specification"

( x i ) SEQUENCE DESCRIPTION: SEQ ID NO:45:

```
Xaa Gly Gly Xaa Xaa Xaa Xaa Xaa
1               5
```

( 2 ) INFORMATION FOR SEQ ID NO:46:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:46:

```
Xaa Gly Gly Gly Xaa
1               5
```

( 2 ) INFORMATION FOR SEQ ID NO:47:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:47:

```
Xaa Gly Gly Gly Xaa Xaa
1               5
```

( 2 ) INFORMATION FOR SEQ ID NO:48:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:48:

```
Xaa Gly Gly Gly Xaa Xaa Xaa
1               5
```

( 2 ) INFORMATION FOR SEQ ID NO:49:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:

-continued ( C ) IDENTIFICATION METHOD:
                ( D ) OTHER INFORMATION: /note ="Xaa is modified amino acid as
                        described in specification"

( x i ) SEQUENCE DESCRIPTION: SEQ ID NO:49:

Xaa  Gly  Gly  Gly  Xaa  Xaa  Xaa  Xaa
1                       5

( 2 ) INFORMATION FOR SEQ ID NO:50:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i x ) FEATURE:
                ( A ) NAME/KEY: modified site
                ( B ) LOCATION:
                ( C ) IDENTIFICATION METHOD:
                ( D ) OTHER INFORMATION: /note ="Xaa is modified amino acid as
                        described in specification"

( x i ) SEQUENCE DESCRIPTION: SEQ ID NO:50:

Xaa  Gly  Gly  Gly  Xaa  Xaa  Xaa  Xaa  Xaa
1                       5

( 2 ) INFORMATION FOR SEQ ID NO:51:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i x ) FEATURE:
                ( A ) NAME/KEY: modified site
                ( B ) LOCATION:
                ( C ) IDENTIFICATION METHOD:
                ( D ) OTHER INFORMATION: /note ="Xaa is modified amino acid as
                        described in specification"

( x i ) SEQUENCE DESCRIPTION: SEQ ID NO:51:

Xaa  Gly  Gly  Gly  Gly  Xaa
1                       5

( 2 ) INFORMATION FOR SEQ ID NO:52:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i x ) FEATURE:
                ( A ) NAME/KEY: modified site
                ( B ) LOCATION:
                ( C ) IDENTIFICATION METHOD:
                ( D ) OTHER INFORMATION: /note ="Xaa is modified amino acid as
                        described in specification"

( x i ) SEQUENCE DESCRIPTION: SEQ ID NO:52:

Xaa  Gly  Gly  Gly  Gly  Xaa  Xaa
1                       5

( 2 ) INFORMATION FOR SEQ ID NO:53:

( i ) SEQUENCE CHARACTERISTICS:
                ( A ) LENGTH: 8 amino acids
                ( B ) TYPE: amino acid
                ( C ) STRANDEDNESS: single (D) TOPOLOGY: linear (ix) FEATURE:
    (A) NAME/KEY: modified site
    (B) LOCATION:
    (C) IDENTIFICATION METHOD:
    (D) OTHER INFORMATION: /note ="Xaa is modified amino acid as described in specification"

(xi) SEQUENCE DESCRIPTION: SEQ ID NO:53:

```
Xaa Gly Gly Gly Gly Xaa Xaa Xaa
1               5
```

(2) INFORMATION FOR SEQ ID NO:54:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(xi) SEQUENCE DESCRIPTION: SEQ ID NO:54:

```
Xaa Gly Gly Gly Gly Xaa Xaa Xaa Xaa
1               5
```

(2) INFORMATION FOR SEQ ID NO:55:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(xi) SEQUENCE DESCRIPTION: SEQ ID NO:55:

```
Xaa Gly Gly Gly Gly Xaa Xaa Xaa Xaa Xaa
1               5                   10
```

(2) INFORMATION FOR SEQ ID NO:56:

(i) SEQUENCE CHARACTERISTICS:
        (A) LENGTH: 3 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(xi) SEQUENCE DESCRIPTION: SEQ ID NO:56:

```
Xaa Gly Xaa
1
```

(2) INFORMATION FOR SEQ ID NO:57:

( i ) SEQUENCE CHARACTERISTICS:
    ( A ) LENGTH: 1 amino acid
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:57:

Xaa

1

( 2 ) INFORMATION FOR SEQ ID NO:58:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:58:

Xaa  Gly  Glu  Xaa

1

( 2 ) INFORMATION FOR SEQ ID NO:59:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:59:

Xaa  Glu  Glu

1

( 2 ) INFORMATION FOR SEQ ID NO:60:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:60:

Xaa Glu Xaa
1

( 2 ) INFORMATION FOR SEQ ID NO:61:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:61:

Xaa Glu Glu Glu
1

( 2 ) INFORMATION FOR SEQ ID NO:62:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:62:

Xaa Glu Glu Xaa
1

( 2 ) INFORMATION FOR SEQ ID NO:63:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:63:

Xaa Xaa Gly Gly Glu
1               5

( 2 ) INFORMATION FOR SEQ ID NO:64:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:

( C ) IDENTIFICATION METHOD:
( D ) OTHER INFORMATION: /note ="Xaa is modified amino acid as described in specification"

( x i ) SEQUENCE DESCRIPTION: SEQ ID NO:64:

Xaa Gly Gly Gly Glu Thr Thr
1               5

( 2 ) INFORMATION FOR SEQ ID NO:65:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:65:

Xaa Gly Gly Gly Glu
1               5

( 2 ) INFORMATION FOR SEQ ID NO:66:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:66:

Xaa Gly Gly Glu
1

( 2 ) INFORMATION FOR SEQ ID NO:67:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:67:

Xaa Gly Glu Glu
1

( 2 ) INFORMATION FOR SEQ ID NO:68:

( i ) SEQUENCE CHARACTERISTICS:
    ( A ) LENGTH: 4 amino acids
    ( B ) TYPE: amino acid
    ( C ) STRANDEDNESS: single (D) TOPOLOGY: linear (ix) FEATURE:
    (A) NAME/KEY: modified site
    (B) LOCATION:
    (C) IDENTIFICATION METHOD:
    (D) OTHER INFORMATION: /note ="Xaa is modified amino acid as described in specification"

(xi) SEQUENCE DESCRIPTION: SEQ ID NO:68:

```
Xaa  Glu  Gly  Glu
 1
```

(2) INFORMATION FOR SEQ ID NO:69:

(i) SEQUENCE CHARACTERISTICS:
    (A) LENGTH: 4 amino acids
    (B) TYPE: amino acid
    (C) STRANDEDNESS: single
    (D) TOPOLOGY: linear (ix) FEATURE:
    (A) NAME/KEY: modified site
    (B) LOCATION:
    (C) IDENTIFICATION METHOD:
    (D) OTHER INFORMATION: /note ="Xaa is modified amino acid as described in specification"

(xi) SEQUENCE DESCRIPTION: SEQ ID NO:69:

```
Xaa  Glu  Gly  Xaa
 1
```

(2) INFORMATION FOR SEQ ID NO:70:

(i) SEQUENCE CHARACTERISTICS:
    (A) LENGTH: 4 amino acids
    (B) TYPE: amino acid
    (C) STRANDEDNESS: single
    (D) TOPOLOGY: linear (ix) FEATURE:
    (A) NAME/KEY: modified site
    (B) LOCATION:
    (C) IDENTIFICATION METHOD:
    (D) OTHER INFORMATION: /note ="Xaa is modified amino acid as described in specification"

(xi) SEQUENCE DESCRIPTION: SEQ ID NO:70:

```
Xaa  Xaa  Xaa  Xaa
 1
```

(2) INFORMATION FOR SEQ ID NO:71:

(i) SEQUENCE CHARACTERISTICS:
    (A) LENGTH: 5 amino acids
    (B) TYPE: amino acid
    (C) STRANDEDNESS: single
    (D) TOPOLOGY: linear (ix) FEATURE:
    (A) NAME/KEY: modified site
    (B) LOCATION:
    (C) IDENTIFICATION METHOD:
    (D) OTHER INFORMATION: /note ="Xaa is modified amino acid as described in specification"

(xi) SEQUENCE DESCRIPTION: SEQ ID NO:71:

```
Xaa  Xaa  Xaa  Xaa  Xaa
 1                   5
```

(2) INFORMATION FOR SEQ ID NO:72:

( i ) SEQUENCE CHARACTERISTICS:
- ( A ) LENGTH: 4 amino acids
- ( B ) TYPE: amino acid
- ( C ) STRANDEDNESS: single
- ( D ) TOPOLOGY: linear ( i x ) FEATURE:
- ( A ) NAME/KEY: modified site
- ( B ) LOCATION:
- ( C ) IDENTIFICATION METHOD:
- ( D ) OTHER INFORMATION: /note ="Xaa is modified amino acid as described in specification"

( x i ) SEQUENCE DESCRIPTION: SEQ ID NO:72:

Gly Xaa Xaa Xaa
1

( 2 ) INFORMATION FOR SEQ ID NO:73:

( i ) SEQUENCE CHARACTERISTICS:
- ( A ) LENGTH: 5 amino acids
- ( B ) TYPE: amino acid
- ( C ) STRANDEDNESS: single
- ( D ) TOPOLOGY: linear ( i x ) FEATURE:
- ( A ) NAME/KEY: modified site
- ( B ) LOCATION:
- ( C ) IDENTIFICATION METHOD:
- ( D ) OTHER INFORMATION: /note ="Xaa is modified amino acid as described in specification"

( x i ) SEQUENCE DESCRIPTION: SEQ ID NO:73:

Gly Xaa Xaa Xaa Xaa
1                 5

( 2 ) INFORMATION FOR SEQ ID NO:74:

( i ) SEQUENCE CHARACTERISTICS:
- ( A ) LENGTH: 6 amino acids
- ( B ) TYPE: amino acid
- ( C ) STRANDEDNESS: single
- ( D ) TOPOLOGY: linear ( i x ) FEATURE:
- ( A ) NAME/KEY: modified site
- ( B ) LOCATION:
- ( C ) IDENTIFICATION METHOD:
- ( D ) OTHER INFORMATION: /note ="Xaa is modified amino acid as described in specification"

( x i ) SEQUENCE DESCRIPTION: SEQ ID NO:74:

Gly Xaa Xaa Xaa Xaa Xaa
1                 5

( 2 ) INFORMATION FOR SEQ ID NO:75:

( i ) SEQUENCE CHARACTERISTICS:
- ( A ) LENGTH: 4 amino acids
- ( B ) TYPE: amino acid
- ( C ) STRANDEDNESS: single
- ( D ) TOPOLOGY: linear ( i x ) FEATURE:
- ( A ) NAME/KEY: modified site
- ( B ) LOCATION:
- ( C ) IDENTIFICATION METHOD:
- ( D ) OTHER INFORMATION: /note ="Xaa is modified amino acid as described in specification"

( x i ) SEQUENCE DESCRIPTION: SEQ ID NO:75:

Gly Gly Xaa Xaa
1

(2) INFORMATION FOR SEQ ID NO:76:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as
            described in specification"

(xi) SEQUENCE DESCRIPTION: SEQ ID NO:76:

Gly Gly Xaa Xaa Xaa
1                5

(2) INFORMATION FOR SEQ ID NO:77:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as
            described in specification"

(xi) SEQUENCE DESCRIPTION: SEQ ID NO:77:

Gly Gly Xaa Xaa Xaa Xaa
1                5

(2) INFORMATION FOR SEQ ID NO:78:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:
        (D) OTHER INFORMATION: /note ="Xaa is modified amino acid as
            described in specification"

(xi) SEQUENCE DESCRIPTION: SEQ ID NO:78:

Gly Gly Xaa Xaa Xaa Xaa Xaa
1                5

(2) INFORMATION FOR SEQ ID NO:79:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: modified site
        (B) LOCATION:
        (C) IDENTIFICATION METHOD:

(D) OTHER INFORMATION: /note ="Xaa is modified amino acid as described in specification"

(x i) SEQUENCE DESCRIPTION: SEQ ID NO:79:

Gly Gly Gly Xaa
1

(2) INFORMATION FOR SEQ ID NO:80:

(i) SEQUENCE CHARACTERISTICS:
        (A) LENGTH: 5 amino acids
        (B) TYPE: amino acid
        (C) STRANDEDNESS: single
        (D) TOPOLOGY: linear (i x) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(x i) SEQUENCE DESCRIPTION: SEQ ID NO:80:

Gly Gly Gly Xaa Xaa
1                 5

(2) INFORMATION FOR SEQ ID NO:81:

(i) SEQUENCE CHARACTERISTICS:
        (A) LENGTH: 6 amino acids
        (B) TYPE: amino acid
        (C) STRANDEDNESS: single
        (D) TOPOLOGY: linear (i x) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(x i) SEQUENCE DESCRIPTION: SEQ ID NO:81:

Gly Gly Gly Xaa Xaa Xaa
1                 5

(2) INFORMATION FOR SEQ ID NO:82:

(i) SEQUENCE CHARACTERISTICS:
        (A) LENGTH: 7 amino acids
        (B) TYPE: amino acid
        (C) STRANDEDNESS: single
        (D) TOPOLOGY: linear (i x) FEATURE:
        (A) NAME/KEY: modified site
        (B) LOCATION:
        (C) IDENTIFICATION METHOD:
        (D) OTHER INFORMATION: /note ="Xaa is modified amino acid as described in specification"

(x i) SEQUENCE DESCRIPTION: SEQ ID NO:82:

Gly Gly Gly Xaa Xaa Xaa Xaa
1                 5

(2) INFORMATION FOR SEQ ID NO:83:

(i) SEQUENCE CHARACTERISTICS:
        (A) LENGTH: 8 amino acids
        (B) TYPE: amino acid
        (C) STRANDEDNESS: single
        (D) TOPOLOGY: linear ( i x ) FEATURE:
   ( A ) NAME/KEY: modified site
   ( B ) LOCATION:
   ( C ) IDENTIFICATION METHOD:
   ( D ) OTHER INFORMATION: /note ="Xaa is modified amino acid as described in specification"

( x i ) SEQUENCE DESCRIPTION: SEQ ID NO:83:

Gly Gly Gly Xaa Xaa Xaa Xaa Xaa
1        5

( 2 ) INFORMATION FOR SEQ ID NO:84:

( i ) SEQUENCE CHARACTERISTICS:
   ( A ) LENGTH: 5 amino acids
   ( B ) TYPE: amino acid
   ( C ) STRANDEDNESS: single
   ( D ) TOPOLOGY: linear ( i x ) FEATURE:
   ( A ) NAME/KEY: modified site
   ( B ) LOCATION:
   ( C ) IDENTIFICATION METHOD:
   ( D ) OTHER INFORMATION: /note ="Xaa is modified amino acid as described in specification"

( x i ) SEQUENCE DESCRIPTION: SEQ ID NO:84:

Gly Gly Gly Gly Xaa
1     5

( 2 ) INFORMATION FOR SEQ ID NO:85:

( i ) SEQUENCE CHARACTERISTICS:
   ( A ) LENGTH: 6 amino acids
   ( B ) TYPE: amino acid
   ( C ) STRANDEDNESS: single
   ( D ) TOPOLOGY: linear ( i x ) FEATURE:
   ( A ) NAME/KEY: modified site
   ( B ) LOCATION:
   ( C ) IDENTIFICATION METHOD:
   ( D ) OTHER INFORMATION: /note ="Xaa is modified amino acid as described in specification"

( x i ) SEQUENCE DESCRIPTION: SEQ ID NO:85:

Gly Gly Gly Gly Xaa Xaa
1     5

( 2 ) INFORMATION FOR SEQ ID NO:86:

( i ) SEQUENCE CHARACTERISTICS:
   ( A ) LENGTH: 7 amino acids
   ( B ) TYPE: amino acid
   ( C ) STRANDEDNESS: single
   ( D ) TOPOLOGY: linear ( i x ) FEATURE:
   ( A ) NAME/KEY: modified site
   ( B ) LOCATION:
   ( C ) IDENTIFICATION METHOD:
   ( D ) OTHER INFORMATION: /note ="Xaa is modified amino acid as described in specification"

( x i ) SEQUENCE DESCRIPTION: SEQ ID NO:86:

Gly Gly Gly Gly Xaa Xaa Xaa
1     5

( 2 ) INFORMATION FOR SEQ ID NO:87:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i x ) FEATURE:
  ( A ) NAME/KEY: modified site
  ( B ) LOCATION:
  ( C ) IDENTIFICATION METHOD:
  ( D ) OTHER INFORMATION: /note ="Xaa is modified amino acid as described in specification"

( x i ) SEQUENCE DESCRIPTION: SEQ ID NO:87:

Gly Gly Gly Gly Xaa Xaa Xaa Xaa
 1               5

( 2 ) INFORMATION FOR SEQ ID NO:88:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:88:

Gly Gly Gly Gly Xaa Xaa Xaa Xaa Xaa
 1               5

( 2 ) INFORMATION FOR SEQ ID NO:89:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:89:

Xaa Gly Gly Gly Glu Thr Thr
 1               5

( 2 ) INFORMATION FOR SEQ ID NO:90:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:90:

Xaa Gly Gly Gly Glu Thr Thr ( 2 ) INFORMATION FOR SEQ ID NO:91:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:91:

Xaa Gly Gly Gly Glu Thr Thr
1               5

( 2 ) INFORMATION FOR SEQ ID NO:92:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:92:

Xaa Gly Gly Gly Glu
1               5

( 2 ) INFORMATION FOR SEQ ID NO:93:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:93:

Xaa Gly Gly Gly Glu Thr Thr
1               5

( 2 ) INFORMATION FOR SEQ ID NO:94:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as -continued described in specification"

( x i ) SEQUENCE DESCRIPTION: SEQ ID NO:94:

Xaa Gly Gly Gly Glu Thr Thr
1               5

( 2 ) INFORMATION FOR SEQ ID NO:95:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: modified site
  ( B ) LOCATION:
  ( C ) IDENTIFICATION METHOD:
  ( D ) OTHER INFORMATION: /note ="Xaa is modified amino acid as described in specification"

( x i ) SEQUENCE DESCRIPTION: SEQ ID NO:95:

Xaa Gly Gly Gly Glu Thr Thr
1               5

( 2 ) INFORMATION FOR SEQ ID NO:96:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: modified site
  ( B ) LOCATION:
  ( C ) IDENTIFICATION METHOD:
  ( D ) OTHER INFORMATION: /note ="Xaa is modified amino acid as described in specification"

( x i ) SEQUENCE DESCRIPTION: SEQ ID NO:96:

Xaa Gly Gly Gly Glu Thr Thr
1               5

( 2 ) INFORMATION FOR SEQ ID NO:97:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: modified site
  ( B ) LOCATION:
  ( C ) IDENTIFICATION METHOD:
  ( D ) OTHER INFORMATION: /note ="Xaa is modified amino acid as described in specification"

( x i ) SEQUENCE DESCRIPTION: SEQ ID NO:97:

Xaa Gly Gly Gly Glu
1               5

( 2 ) INFORMATION FOR SEQ ID NO:98:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: linear ( i x ) FEATURE:
    ( A ) NAME/KEY: modified site
    ( B ) LOCATION:
    ( C ) IDENTIFICATION METHOD:
    ( D ) OTHER INFORMATION: /note ="Xaa is modified amino acid as described in specification"

( x i ) SEQUENCE DESCRIPTION: SEQ ID NO:98:

Xaa Gly Gly Gly Glu Thr
1                   5

( 2 ) INFORMATION FOR SEQ ID NO:99:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:99:

Xaa Gly Gly Gly Glu
2               5

( 2 ) INFORMATION FOR SEQ ID NO:100:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:100:

Xaa Gly Gly Gly Asp
1               5

( 2 ) INFORMATION FOR SEQ ID NO:101:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as described in specification"

( x i ) SEQUENCE DESCRIPTION: SEQ ID NO:101:

Xaa Gly Gly Gly
1

( 2 ) INFORMATION FOR SEQ ID NO:102:

( i ) SEQUENCE CHARACTERISTICS:

( A ) LENGTH: 4 amino acids
            ( B ) TYPE: amino acid
            ( C ) STRANDEDNESS: single
            ( D ) TOPOLOGY: linear ( i x ) FEATURE:
            ( A ) NAME/KEY: modified site
            ( B ) LOCATION:
            ( C ) IDENTIFICATION METHOD:
            ( D ) OTHER INFORMATION: /note ="Xaa is modified amino acid as
                described in specification"

( x i ) SEQUENCE DESCRIPTION: SEQ ID NO:102:

Xaa Gly Gly Glu
1

( 2 ) INFORMATION FOR SEQ ID NO:103:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i x ) FEATURE:
            ( A ) NAME/KEY: modified site
            ( B ) LOCATION:
            ( C ) IDENTIFICATION METHOD:
            ( D ) OTHER INFORMATION: /note ="Xaa is modified amino acid as
                described in specification"

( x i ) SEQUENCE DESCRIPTION: SEQ ID NO:103:

Xaa Gly Glu Glu
1

( 2 ) INFORMATION FOR SEQ ID NO:104:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i x ) FEATURE:
            ( A ) NAME/KEY: modified site
            ( B ) LOCATION:
            ( C ) IDENTIFICATION METHOD:
            ( D ) OTHER INFORMATION: /note ="Xaa is modified amino acid as
                described in specification"

( x i ) SEQUENCE DESCRIPTION: SEQ ID NO:104:

Xaa Glu Gly Glu
1

( 2 ) INFORMATION FOR SEQ ID NO:105:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i x ) FEATURE:
            ( A ) NAME/KEY: modified site
            ( B ) LOCATION:
            ( C ) IDENTIFICATION METHOD:
            ( D ) OTHER INFORMATION: /note ="Xaa is modified amino acid as
                described in specification"

( x i ) SEQUENCE DESCRIPTION: SEQ ID NO:105:

Xaa Glu Glu Glu
1

( 2 ) INFORMATION FOR SEQ ID NO:106:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: modified site
        ( B ) LOCATION:
        ( C ) IDENTIFICATION METHOD:
        ( D ) OTHER INFORMATION: /note ="Xaa is modified amino acid as
            described in specification"

( x i ) SEQUENCE DESCRIPTION: SEQ ID NO:106:

Xaa  Xaa  Gly  Gly  Glu
 1                        5